(12) United States Patent
Karn et al.

(10) Patent No.: US 6,573,045 B1
(45) Date of Patent: Jun. 3, 2003

(54) METHODS AND KITS FOR DISCOVERY OF RNA-BINDING COMPOUNDS

(75) Inventors: Jonathan Karn, Little Shelford (GB); Catherine Denise Prescott, Cambridge (GB)

(73) Assignee: Ribotargets, Ltd., Cambridge (GB)

( * ) Notice: Subject to any disclaimer, the term of this patent is extended or adjusted under 35 U.S.C. 154(b) by 0 days.

(21) Appl. No.: 09/325,601

(22) Filed: Jun. 3, 1999

Related U.S. Application Data

(60) Provisional application No. 60/088,241, filed on Jun. 5, 1998, and provisional application No. 60/122,439, filed on Mar. 2, 1999.

(51) Int. Cl.[7] .............................. C12Q 1/68; C12Q 1/70; C12P 19/34; C07H 21/04
(52) U.S. Cl. ............................. 435/6; 435/5; 435/91.1; 536/22.1
(58) Field of Search .......................... 435/6, 5; 536/22.1

(56) References Cited

U.S. PATENT DOCUMENTS 5,593,835 A    1/1997    Rando ........................... 435/6

FOREIGN PATENT DOCUMENTS

| WO | WO 92 02228 | | 2/1992 | | |
|----|----|----|----|----|----|
| WO | WO 94 29487 | | 12/1994 | | |
| WO | WO 96/35706 | * | 11/1996 | .................... | 435/6 |
| WO | WO 97 09342 | | 3/1997 | | |
| WO | WO98/39484 | | 3/1997 | ............ | C12Q/1/68 |
| WO | WO 97 43444 | | 11/1997 | | |
| WO | WO13338 A1 | | 9/1998 | .......... | G01N/33/68 |
| WO | WO 98 39484 | | 9/1998 | | |
| WO | WO 99 09056 | | 2/1999 | | |
| WO | WO 99 13338 | | 3/1999 | | |
| WO | WO99/64625 A2 | | 6/1999 | ............ | C12Q/1/68 |
| WO | WO97/09342 | | 9/1999 | ........... | C07H/21/02 |

OTHER PUBLICATIONS

Stratagene Catalog, p. 39, col. 1, 1988.*
Calnan et al., *Genes and Developement*, vol. 5, pp. 201–210 (1991).
Cardullo et al., *PNAS*, vol. 85, No. 23, pp. 8790–8794 (1988).
Churcher et al., *Journal of Molecular Biology*, vol. 230, pp. 90–110 (1993).
Mei et al., *Bioorganic & Medical Chemistry*, vol. 5, pp. 1173–1184 (1997).
Metzger et al., *Biochemical and Biophysical Research Communications*, vol. 241 (1997).
Wang et al., *Biochemistry*, vol. 36, pp. 768–779 (1997).
International Search Report.
Copy of International Search Report.

* cited by examiner

*Primary Examiner*—W. Gary Jones
*Assistant Examiner*—Arun Kr. Chakrabarti
(74) *Attorney, Agent, or Firm*—Palmer & Dodge, LLP; Kathleen M. Williams

(57) ABSTRACT

The invention relates to a solution-based assay for identifying RNA binding compounds, based on competition. The assay comprises a reporter molecule carrying a fluorescent or chromogenic group that can form a one-to-one complex with an RNA target molecule carrying a second fluorescent or chromogenic group in such a way that the two groups are in sufficient proximity for fluorescence resonance energy transfer and/or quenching to take place. Addition of a compound-to-be-tested prevents formation of the complex and thereby increases the fluorescence of the RNA target and/or reporter molecules relative to the signal obtained in the absence of the test compound. The invention also provides for quantitative screening methods and kits are also included.

25 Claims, 19 Drawing Sheets

Labelled ADP-1 Reporters

TAMRA-FTTKALGISYGRKKRRQRRRPPQGSGTHQVSLSKQ
FAM-FTTKALGISYGRKKRRQRRRPPQGSGTHQVSLSKQ
DABCYL-FTTKALGISYGRKKRRQRRRPPQGSGTHQVSLSKQ

FIG. 2A

Labelled TAR RNA Duplexes

5'-AGCCAGA U$^U$U GAGCAGC-3'
3'-UCGGUCU---CUCGUCG-FAM-5'

5'-AGCCAGA U$^U$U GAGCAGCG-3'
3'-UCGGUCU---CUCGUCGC-FAM-5'

FIG. 2B

Labelled TAR RNAs

5'-FAM-CCCAGA U$^C$U GAGC  C$^U$G
3'-----GGGUCU---CUCG$_A$G$_G$

5'-Cy3-CCCAGA U$^C$U GAGC  C$^U$G
3'-----GGGUCU---CUCG$_A$G$_G$

5'-CCCAGA U$^C$U GAGC  C$^U$G
3'-DABCYL-GGGUCU---CUCG$_A$G$_G$

FIG. 2C

Labelled Rev reporters

TAMRA-DTRQARRNRRRRWRERQR
FAM-DTRQARRNRRRRWRERQR

FIG. 3A

Labelled RRE-RNA

5'-Cy3-CGUGUG$^{G\ G}$ CGCAGCGUC$^{A}_{A}$
3'-GCACAC$_{A_UG}$ GCGUCGCAG$_U$

5'-FAM-CGUGUG$^{G\ G}$ CGCAGCGUC$^{A}_{A}$
3'-GCACAC$_{A_UG}$ GCGUCGCAG$_U$

5'-CGUGUG$^{G\ G}$ CGCAGCGUC$^{A}_{A}$
3'-DABCYL-GCACAC$_{A_UG}$ GCGUCGCAG$_U$

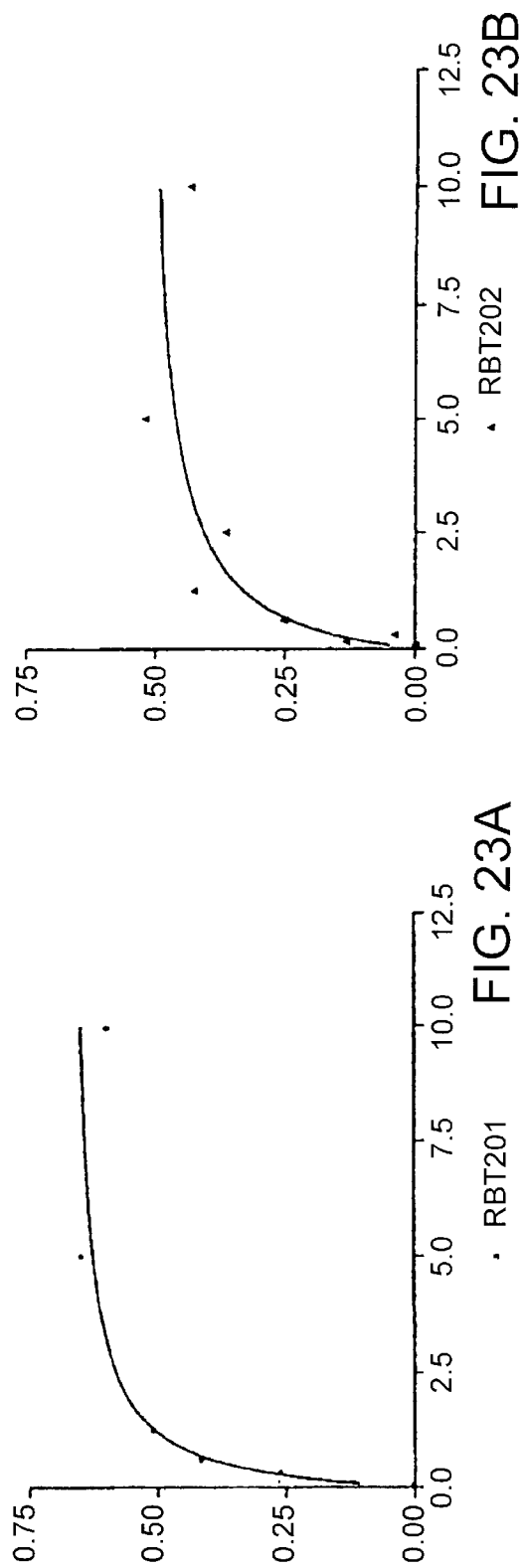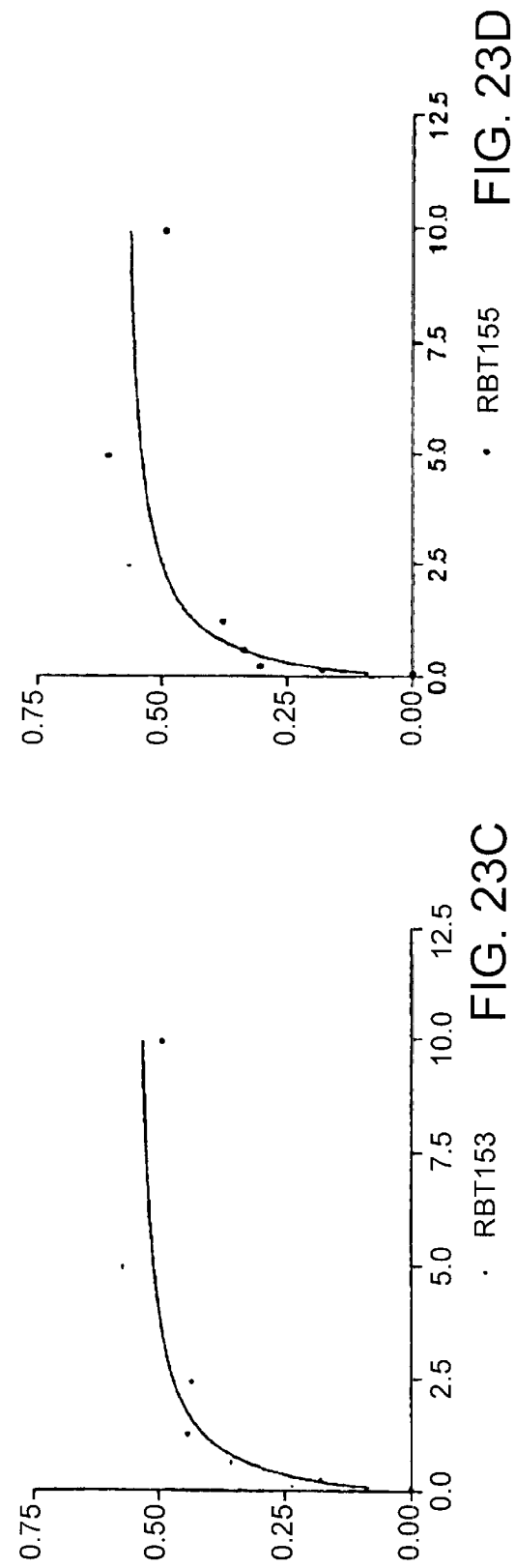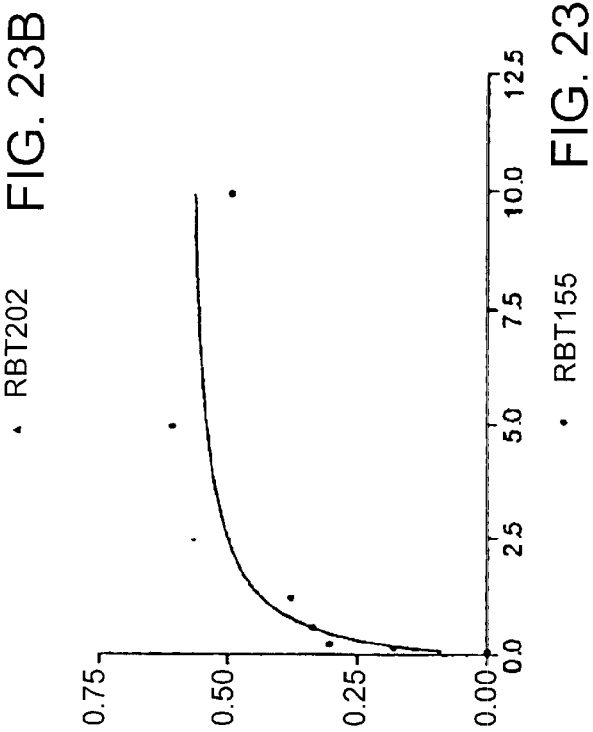

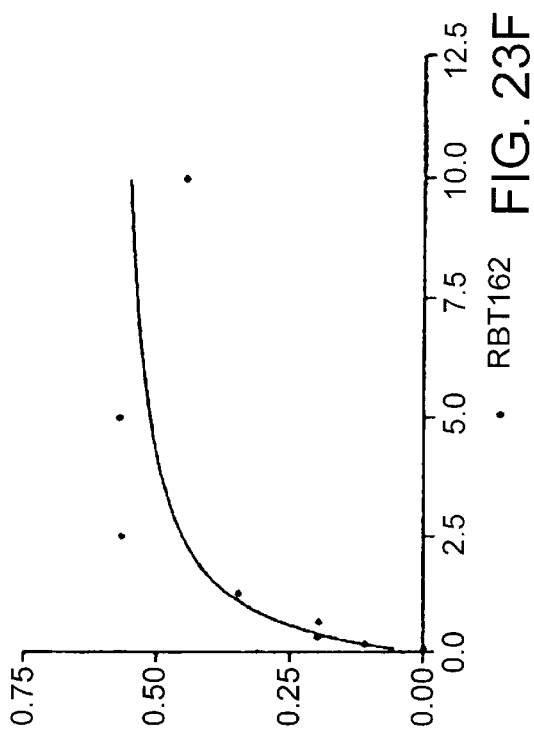
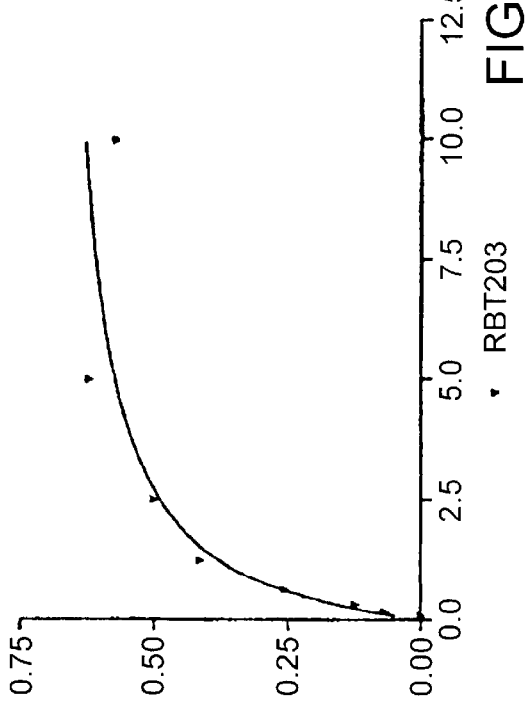
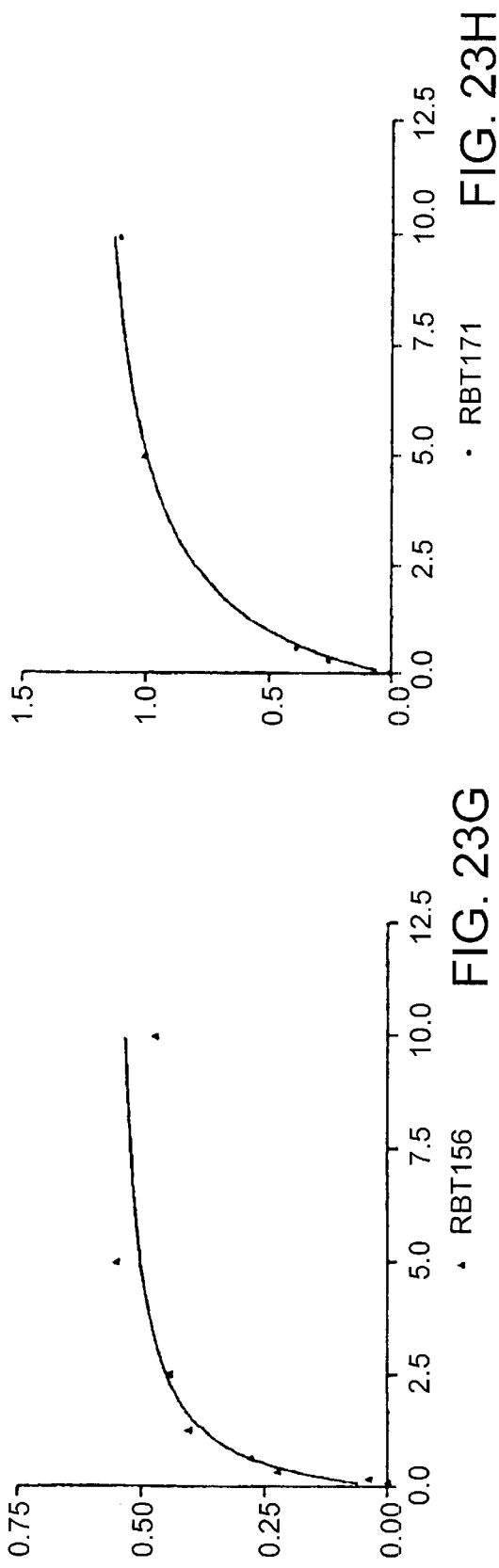

METHODS AND KITS FOR DISCOVERY OF RNA-BINDING COMPOUNDS

This application claims the benefit of provisional application Ser. No. 60/088,241, filed Jun. 5, 1998 and Ser. No. 60/122,439, filed Mar. 2, 1999.

FIELD OF THE INVENTION

The present invention relates to the specific interactions of low molecular weight compounds with RNA. More particularly, the present invention relates to compositions, methods and kits for identifying compounds that interfere with RNA-protein or RNA-ligand interactions and thereby interfere with RNA function.

BACKGROUND OF THE INVENTION

In most biological systems, the maturation, transport, stability and expression of RNA is closely regulated by the interactions between highly conserved regulatory RNA sequences and proteins. In many circumstances it is desirable to develop drugs that bind RNA at sites of regulatory protein binding and act as competitive inhibitors of the RNA-protein interaction. These types of drugs have potential applications in a wide range of diseases including viral, bacterial and fungal infections and chronic diseases such as cancer and autoimmune disease.

1. RNA Targets for Drug Discovery

Although RNA is often referred to as being single stranded and unstructured, most biologically active RNA molecules actually fold back on themselves to create a wide variety of structures. In RNA structures, the secondary structure is energetically the largest contributor to the overall three-dimensional fold. The main secondary structure element in large RNA molecules is the RNA double helix built by Watson-Crick base pairings between two regions of the RNA polynucleotide. The helical elements in RNA are typically interrupted by bulges and internal loops. In addition to disruptions of the helical structures, biologically active RNA molecules typically contain specialized loop sequences that create stable bends in RNA. Associations between single stranded regions and between single stranded regions and double helices lead to structural elements creating tertiary structures. Many tertiary structural elements in RNA form recurrent motifs, such as "pseudoknots" created by the interactions of pairs of loop structures. Additional tertiary structure elements such as base triples are also commonly found in large RNA structures.

Regulatory proteins seldom target fully-double stranded regions of RNA, which like A-form DNA forms a comparatively rigid structure in which most functional groups that distinguish between the bases are inaccessible. Instead, RNA-binding proteins generally target functional groups where bulges, loops and hairpins disrupt the regular RNA helix and open up the major groove for interaction with protein side chains. Regulatory proteins usually interact with these bulges, loops and hairpins that disrupt the regular RNA helix. These secondary structure elements provide the structural diversity needed for protein recognition as well as for drug development.

2. RNA Targets in HIV

A great deal of the present knowledge about the structure of RNA targets and their recognition by RNA binding proteins has come from studies of two human immunodeficiency virus (HIV) regulatory proteins Tat, the trans-activator protein and Rev, the regulator of virion expression. The two proteins play complementary roles in the virus life cycle. Tat stimulates transcription from the viral long terminal repeat (LTR), whereas Rev is required for the efficient export from the nucleus of the late mRNAs encoding the structural proteins of the virus.

Tat and Rev both exert their effects through specific cis-acting viral RNA regulatory sequences. Tat activity requires the trans-activation-responsive region (TAR), an RNA regulatory element of 59 nucleotides (nt) located immediately downstream of the initiation site for transcription (Cullen, 1990; Karn et al., 1995). Because of its position in the HIV genome, each viral mRNA carries a copy of TAR at its 5'-end.

TAR RNA forms a highly stable, nuclease-resistant, stem-loop structure. Point mutations, which disrupt base-pairing in the upper TAR RNA stem invariably, abolish Tat-activated transcription. In 1989 Dingwall et al. provided the first demonstration that recombinant Tat expressed in *Escherichia coli* could bind specifically to bases in the stem of the TAR RNA (Dingwall et al., 1989). The binding site for Tat includes a U-rich trinucleotide bulge found in the upper stem of TAR RNA.

Extensive mutagenesis, chemical probing and peptide binding studies have defined the key elements required for TAR recognition by Tat and have shown that the Tat binding site surrounds a UCU bulge located near the apex of TAR (Calnan et al., 1991a; Weeks & Crothers, 1991; Delling et al., 1992; Churcher et al., 1993; Hamy et al., 1993; WO92/02228). Tat interacts with the first uridine of the bulge, U23, while the other residues in the bulge act predominantly as spacers and may be replaced by other nucleotides, or even by non-nucleotide linkers (Churcher et al., 1993). Tat recognition requires two base-pairs in the stem above the U-rich bulge, G26·C39 and A27·U38 (Weeks & Crothers, 1991; Delling et al., 1992; Churcher et al., 1993). Two base pairs below the bulge, A22·U40 and G21·C41, also make significant contributions to Tat binding. Critical phosphate contacts involve phosphates P21, P22, and P40, which are located below the bulge on both strands (Calnan et al., 1991b; Hamy et al., 1993; Pritchard et al., 1994).

In addition to binding the Tat protein, TAR is able to form complexes with short peptides containing an arginine-rich sequence derived from residues 48 to 57 of Tat (Cordingley et al., 1990; Weeks et al., 1990; Calnan et al., 1991a; Weeks & Crothers, 1991; Churcher et al., 1993). However, compared to the Tat protein, short arginine-rich peptides bind with reduced affinity and, in certain cases, also have a significantly reduced binding specificity (Churcher et al., 1993). For example, short basic region peptides (such as the ADP-3 peptide, residues 48 to 72) show less than a 2-fold difference in affinity between wild-type TAR RNA and TAR sequences carrying the mutations U23→C and G26·C39→C·G mutations (Churcher et al., 1993). Similarly, some basic peptides display a high affinity for any duplex RNA sequences that carries one or more bulged residues. Monomeric complexes between peptides and TAR are only obtained when TAR is truncated and the competing binding sites normally present on the lower stem are removed (Weeks et al., 1990; Weeks & Crothers, 1991; Churcher et al., 1993). By contrast, peptides such as ADP-1 (residues 37 to 72, see FIG. 3) that contain residues from the conserved "core" region of lentivirus trans-activators, have a higher affinity for TAR RNA and are able to discriminate between TAR RNA mutants with a specificity which more closely resembled that of the Tat protein itself (Churcher et al., 1993).

Recent NMR studies of TAR RNA demonstrate that the accessibility of the critical functional groups recognized by Tat and basic peptides is enhanced by rearrangement of the bulge region (Puglisi et al., 1992; Aboul-ela et al., 1995; Aboul-ela et al., 1996). This refolding process involves one of the arginine side chains present in the basic binding domain of the Tat protein (Puglisi et al., 1992; Aboul-ela et al., 1995). In the presence of the arginine, the stacking of the bulged residues U23 on A22 and C24 on U23 is disrupted and A22 becomes juxtaposed to G26. This creates a binding pocket where the guanidinium and (—NH groups of the arginine are placed within hydrogen-bonding distance of G26-N7 and U23-04, respectively. The conformational change in TAR RNA also repositions the P22, P23 and P40 phosphates, which provide energetically important contacts with Tat (Pritchard et al., 1994).

The Tat-TAR interaction therefore provides a clear example of the 'indirect readout' of nucleic acid sequences through recognition of backbone phosphates. The importance of arginine binding pocket in TAR for Tat binding is confirmed by the observation that the mutations that produce the most severe reductions in TAR activity involve G26 and U23 and disrupt the intermolecular interactions that are responsible for the folding transition (Weeks & Crothers, 1991; Churcher et al., 1993).

Rev activity requires a second cis-acting sequence, called the Rev-response element (RRE) which is located within the env reading frame (Malim et al., 1989a). The RRE contains a series of stem loop structures protruding from a long central stem, Stem I (Malim et al., 1989b; Mann et al., 1994). Near the apex of Stem I is a high affinity binding site, which is recognized by a monomer of Rev protein with a Kd~nM (Bartel et al., 1991; Heaphy et al., 1991; Iwai et al., 1992; WO92/05195). The high affinity site is a purine-rich bubble stabilized by non-Watson-Crick G·A and G·G base pairs (Bartel et al., 1991; Iwai et al., 1992; Pritchard et al., 1994). The non-Watson-Crick base pairs, along with a bulged-out uridine nucleotide, open the major groove and permit the recognition of functional groups on the two base pairs either side of the bulged region (Iwai et al., 1992; Kjems et al., 1992; Pritchard et al., 1994). In addition to the base-specific contacts, phosphate contacts are made around the bubble and up to six nucleotides away from the bubble, towards the apex of the stem-loop (Iwai et al., 1992; Kjems et al., 1992; Pritchard et al., 1994).

Mutational analysis of the RRE has shown that the high affinity site is necessary, but not sufficient, for Rev activity in vivo (Malim et al., 1989b; Mann et al., 1994). The binding of a Rev monomer to the high affinity site nucleates the co-operative oligomerization of Rev protein along flanking RNA sites in Stem I (Heaphy et al., 1990; Heaphy et al., 1991; Malim & Cullen, 1991; Mann et al., 1994; Zemmel et al., 1996; WO97/39128). The simplest way to visualize this process is by gel mobility shift assays. These assays show that there is a progressive increase in the formation of the highest molecular complexes as the molar ratio of Rev to RRE RNA increases (Heaphy et al., 1990; Heaphy et al., 1991; Kjems et al., 1991; Malim & Cullen, 1991; Zemmel et al., 1996). Truncations of Stem I that do not affect the high affinity site, reduce Rev responses by removing secondary binding sites, with the longest truncations producing the greatest losses of activity (Mann et al., 1994). Similarly, mutations in the Rev protein that block oligomerization produce an inactive protein (Malim & Cullen, 1991). These observations suggest that the RRE acts as a 'molecular rheostat' designed to detect Rev levels during the early stages of the HIV growth cycle (Mann et al., 1994).

Short basic peptides are also able to bind to the RRE high affinity binding site (Kjems et al., 1992; Battiste et al., 1994; Battiste et al., 1996; Jain & Belasco, 1996). Gel mobility shift assays have shown that basic peptides containing residues that have a propensity to form alpha-helices bind the RRE with enhanced affinity (Tan et al., 1993). Rev suppressor mutations that alleviated the deleterious effects of mutations in the RRE high affinity binding site all map to a single arginine-deficient face of a Rev alpha-helix, providing genetic evidence for direct contacts between specific Rev amino acids and RNA nucleotides in the RNA complex of Rev (Jain & Belasco, 1996).

Frankel et al. (WO94/29487) have described compositions of peptide analogues that mimic the RNA-binding domain of the native Rev protein and are able to bind to the HIV RRE with nanomolar affinity. All of these peptides have a propensity to form alpha-helices.

The structural basis for Rev binding to the RRE high affinity site has recently been revealed by NMR studies (Battiste et al., 1996; Peterson & Feigon, 1996; Ye et al., 1996). These studies demonstrate that the RRE high affinity site contains a large open major groove, which is able to accommodate an alpha-helical peptide. The phosphate backbone adjacent to the G·G base pair undergoes a conformational rearrangement during peptide binding and adopts an unusual locally parallel-stranded orientation. This distortion results in an under twisting of the base pairs in the bulge region and an opening of the major groove by approximately 5 Å. The Rev alpha helix appears to penetrate much more deeply into the major groove than is typical of DNA binding proteins. Several arginine side chains from the peptide make base-specific contacts, and an asparagine residue contacts the G·A base pair.

3. RNA Mimics of Regulatory Protein Binding Sites

Small fragments of RNA are often able to fold into structures that mimic protein binding sites. Model RNAs that fold into the correct structures are able to bind regulatory proteins with similar affinity and specificity to the original RNA sequences and are commonly used as components in assays for RNA-protein interactions since their small size permits synthesis on a large scale either by chemical methods or by transcription from DNA templates.

Karn et al. (WO92/02228 and U.S. Pat. No. 5,821,046 (issued Oct. 13, 1998)) have described oligonucleotide stem-loop structures and duplexes that form analogues of the Tat binding site on TAR RNA. They have also disclosed an assay for identifying a compound that inhibits the binding of Tat protein to TAR RNA based on competition between the compound-to-be-tested and the Tat protein for binding to TAR RNA and its analogues.

The high affinity Rev binding site can also be mimicked by artificial stem-loop structures carrying fragments of the RRE (Bartel et al., 1991; Heaphy et al., 1991; Kjems et al., 1992; Pritchard et al., 1994). Karn et al. (WO92/05195 and U.S. Pat. No. 5,786,145 (issued Jul. 28, 1998)) have described compositions of oligonucleotides that, when folded, correspond to the high affinity site bound by the HIV Rev protein. Karn et al. (ibid.) also describe an assay for identifying compounds that inhibit Rev binding based on competition between the compound-to-be-tested and the Rev protein for binding to RRE RNA and its analogues.

A model RNA sequence for the aminoglycoside binding site on *Escherichia coli* 16S rRNA has been described by Purohit and Stern (1994, and U.S. Pat. No. 5,712,096 (issued Jan. 27, 1998). These RNA model sequences include a nucleic acid structure derived from the parental ribosomal RNA that is capable of binding to a ligand (such as the aminoglycoside) in the original RNA structure and a stabilizing sequence that provides the model RNA with a conformation that permits ligand binding that is substantially identical to the parental RNA ligand binding pattern.

4. Non-fluorescent Assays for RNA-protein Interactions

A critical step in the development of RNA-binding drugs is the development of simple and robust assays that are suitable for the high throughput screening of large compound libraries developed either by combinatorial synthesis traditional medicinal chemistry approaches, or from collections of natural products. The original assays for RNA-protein interactions involving the HIV regulatory proteins were based on filter binding (Churcher et al., 1993; Mei et al., 1997), gel retardation (Calnan et al., 1991a; Weeks & Crothers, 1991; Churcher et al., 1993; Hamy et al., 1993; Hamy et al., 1997; Mei et al., 1997), scintillation proximity (Mei et al., 1997) or electrospray mass spectroscopy (Sannes-Lowery et al., 1997). In all of these assays the free protein (or peptide mimic of the protein) or the free RNA is separated from the complex by physical means. For example, in the gel shift assay, the RNA is labeled by a radioactive or fluorescent group and the free RNA is separated from the complex by electrophoresis. In the filter binding assay, free RNA is separated from protein-bound RNA because of selective binding of the protein to nitrocellulose filter membranes, while in the scintillation proximity method, RNA is bound to the surface of a bead carrying scintillant and free peptide carrying a radioactive label is brought into contact with the bead because of its affinity for RNA. In the mass spectroscopy assay the peptide-RNA complex is ionized and separated by electrospray. Unfortunately none of these assays is ideal for high throughput screening, since they each require a large number of manipulations after the binding reactions have been set up.

5. Use of Fluorescent Probes to Measure Binding of Ligands to Nucleic Acids and Conformational Changes in Nucleic Acids There are many different types of assays that measure the binding of ligands to nucleic acids, or conformational changes in nucleic acids and utilize fluorescence resonance energy transfer (FRET) to generate a signal. FRET is caused by a change in the distance separating a fluorescent donor group from an interacting resonance energy acceptor, either another fluorophore, a chromophore, or a quencher. Combinations of donor and acceptor moieties are known as "FRET pairs". Efficient FRET interactions require that the absorption and emission spectra of the dye pairs have a high degree of overlap. FRET is also a distance-dependent interaction which is dependent on the inverse sixth power of the intermolecular separation, making it a sensitive measurement of molecular distances (Stryer, 1978 and Selvin, 1995).

One application of this technology is to measure incorporation of new bases for the purposes of genetic diagnostics. Chen & Kwok (1997) and Chen et al., (1997), demonstrated that a 5' fluorescein-labeled primer can be extended with a dye-labeled dNTP and modified Taq DNA polymerase. The doubly-labeled DNA oligonucleotide can then be detected by measuring changes in fluorescence intensity.

A variety of assays that utilize FRET to detect hybridization between nucleic acids carrying fluorescent dyes are known. Tyagi and Kramer have described a method of "molecular beacons" (WO95/133399; WO97/39008; and Tyagai and Kramer, 1996) in which a fluorescently labeled DNA reporter is constructed that carries a pair of fluorescent dyes on its 3' and 5' ends, a target recognition signal, and arms surrounding the target recognition signal that can hybridize and form a hairpin structure with the target sequence as the single stranded region. In this conformation, the FRET dye pair on the reporter are brought into close proximity and quenched by FRET. When the reporter molecule hybridizes to a second DNA molecule that is complementary to the target recognition sequence, the stem of the reporter is disrupted and a conformation change is induced that results in an increase in fluorescence and/or a decrease in quenching.

Another method to detect hybridization between two DNA molecule that is based on FRET is described by Cardullo et al. (1988). This method utilizes a probe comprising a pair of compentary oligodeoxynucleotides, one of which contains a fluorophore on its 5' end, and the other of which contains a complentary fluorophore on its 3' end. Hybridization of the two probes brings the fluorescent groups into proximity and results in FRET. A related method is described by Heller et al. (EP 0070685 and Heller and Jablonski, U.S. Pat. No. 4,996,143 (issued Feb. 26, 1991)). In this method, hybridization probes are designed to provide predetermined nucleotide base unit spacings between the donor and acceptor fluorophores. When the probes are hybridized to the target polynucleotide the fluorophores paired for non-radiative energy transfer are optimally separated by 2 to 7 nucleotide base units.

FRET has also been used extensively to measure conformational changes in RNA (for review see Yang & Millar, 1997) including studies of the overall geometry of four-way RNA junctions (Duckett et al., 1995), the hammerhead ribozyme (Tuschl et al., 1994; Bassi et al., 1997) and the kinking RNA helices by bulged nucleotides (Gohlke et al., 1994). These studies have taken advantage of the ability of FRET to measure changes in distances between two probes. In each of these applications the nucleic acid under study is assembled from several chains, two of which have been site-specifically labeled with fluorescent probes. Changes in the folding of the assembled nucleic acid complexes changes the distances between the fluorescent probes and alters the intensity of the fluorescent emission spectra.

Fluorescence energy transfer can also measure conformational changes in DNA induced by proteins. For example, (Bazemore et al., 1997) measured RecAcatalyzed pairing and strand exchange in solution by energy transfer between fluorescent dyes placed at the ends of DNA oligonucleotides. RecA induced pairing of a single-stranded DNA molecule with a DNA duplex increased the energy transfer, whereas strand displacement resulted in a decrease in energy transfer.

There have been comparatively few attempts to use fluorescence methods to measure the formation of protein-DNA complexes. Drees et al., (1996) developed a protein-DNA interaction assay based on the ability to label heat shock protein with fluorescein. Upon binding to DNA the heat shock protein forms a trimer and this is accompanied by an increase in fluorescence. To measure the stoichiometry of the heat shock protein-DNA complex, complexes were formed between the fluorescently labeled heat shock protein and thiazole orange thioazole blue heterodimer (TOTAB) labeled-DNA. The ratios of the protein and DNA determined by two-color fluorescence emission assay. Measurement of complex formation by FRET was not attempted in these experiments.

6. Use of Fluorescence to Measure Ligand Binding to RNA

An improvement in the technology for measuring the ability of small molecules to bind to RNA is to utilize fluorescent reporters. Current methods all rely on the labeling of either the nucleic acid or the ligand with a fluorescent tag and measuring changes in fluorescence emission spectrum after binding. For example, Royer (U.S. Pat. No.

5,445,935 (issued Aug. 29, 1995)) described the use of polarization of the fluorescence emission from a labeled macromolecule, such as a DNA or RNA oligonucleotide, to assess the binding of the labeled macromolecule to a second unlabeled macromolecule, such as a protein. Similarly, (Metzger et al. (1997) have measured binding of unlabeled peptides derived from Tat to TAR RNA by measuring quenching of the intrinsic fluorescence of the peptide after it is bound to RNA.

In another application of fluorescence polarization, Richardson and Schulman (U.S. Pat. No. 4,257,774 (issued Mar. 24, 1981)) reported a method for detecting compounds that interact with nucleic acids by inhibition of acridine orange binding to the nucleic acid which, results in a change in fluorescence polarization. This method is of limited practical use because the binding of acridine is through intercalation at a wide variety of sites on double-helical structures, with the consequent result that the specificity of the assay is limited.

Wang & Rando (U.S. Pat. No. 5,593,835 (issued Jan. 14, 1997) and Wang et al., 1997) have discovered that the attachment of certain fluorescent moieties to an aminoglycoside antibiotic enables the subsequent binding interaction of the antibiotic with an RNA molecule to be enhanced. They have used this property to develop quantitative screening methods and kits for RNA binding compounds. In their method the fluorescently-labeled antibiotic is bound to a pre-selected region of the target RNA, thereby forming a complex which is less fluorescent that the unbound fluorescent antibiotic because of quenching of the fluorescent moiety due to its interaction with the target RNA molecule. The complex is then mixed with a compound-to-be-tested, and the fluorescence of the antibiotic measured. The antibiotic becomes more fluorescent if the compound displaces the antibiotic in the complex and binds to the pre-selected region of the target RNA.

A limitation to the use of aminoglycosides as fluorescent reporters is that these compounds are known to interact with a wide range of cellular and viral RNAs with similar affinities. For example, aminoglycosides are able to inhibit the self-cleavage activity of the hepatitis delta virus (HDV) ribozyme (Rogers et al., 1996), as well as group I self-splicing introns and the so-called 'hammerhead' ribozyme (von Ahsen & Schroeder, 1991; Wank et al., 1994; Rogers et al., 1996). Furthermore, neomycin is able to inhibit HIV-1 Rev binding to its target RRE RNA (Zapp et al., 1993; Werstuck et al., 1996). Similarly, Wang et al., (1997) compared the binding of various aminoglycosides to RRE RNA and ribosomal RNA with the goal of quantitatively determining the nature of the binding interactions between aminoglycoside antibiotics and biologically relevant RNA targets. This study concluded that the specificity for natural RNA constructs in binding aminoglycosides is very limited; not only can aminoglycosides bind many RNA structures with similar affinity, but large families of aminoglycosides are generally active as antibiotics, suggesting that inherent specificity for a particular aminoglycoside is limited (Wang et al., 1997).

In certain circumstances a fluorescently-labeled peptide has been used in place of an antibiotic to bind RNA. Wang et al. (1997) have prepared a fluorescent analogue of Rev34-50 (Fl-Rev34-50) and showed by fluorescence anisotropy (polarization) measurements that this peptidic-compound can bind the HIV-1 RRE region. Binding of unlabeled aminoglycoside antibiotics to the RRE can be measured in competition to the binding of the Fl-Rev34-50. As in the previous assay using antibiotics, quenching of the fluorescent group is due to its binding to the RNA target itself.

A second, and more general, limitation to the use of a single fluorescent group on a reporter molecule is that this group has to interact directly with the RNA target in order to show alterations in its fluorescence emission spectrum. This severely limits the number of positions on the reporter that can be modified and also alters the nature of the binding of the reporter to RNA.

Laing et al., (WO98/39484) have developed a screening method for compound binding to RNA based on the measurement of conformation changes in the target RNA. The RNA conformational changes are detected by the binding a fluorescently labeled probe, typically a fluorescently-labeled oligonucleotide which is complementary to part of the target RNA sequence. In this method the target RNA is unlabeled and interactions between the probe and the target RNA sequence are detected by fluorescence anisotropy. Binding of a test compound is detected by inhibition of the interactions between the oligonucleotide probe and the target RNA sequence.

Arenas et al. (WO97/09342) have described high-throughput screening methods for compounds that bind RNA. The Arenas et al. method is based on measuring changes in the conformation of an RNA target in the presence of a pre-defined ligand and in the presence or absence of test compounds. The method is based on the ability of certain test ligands, typically oligonucleotides, to form complexes with partially unfolded RNA targets and alter their folded states (i.e. its native conformation as defined by its particular patterns of intramolecular base-pairing and higher order structures). In the Arenas et al. method, experimental conditions are chosen so that the target RNA is subjected to unfolding (i.e., disruption of Watson-Crick base pairs) in the presence of the ligand. If the test ligand binds to the unfolded form of the target RNA under these conditions, then the relative amount of folded RNA can be compared to the relative amount of the complex formed between the target RNA and the ligand. The compounds that bind to the native conformation of the target RNA can then be detected as an increase in the proportion of folded target RNA in the sample compared to the amount of unfolded RNA-ligand complex.

In certain embodiments of the Arenas et al. method, FRET is used to detect either the folded target RNA or the unfolded RNA-ligand complex. In one such embodiment, the ligand is a fluorescently labeled oligonucleotide which is complementary to the target RNA, and two fluorescent groups come into proximity after the unfolding of the target RNA and the formation of a complex between the unfolded RNA and the oligonucleotide ligand.

It is an object of the invention to apply FRET methodologies to measure the formation of a complex between a fluorescently-labeled reporter molecule and fluorescently-labeled RNA target. One reason why this approach has not been undertaken previously is that NMR studies have shown that of RNA-peptide complexes are in intermediate exchange, suggesting a high degree of conformational flexibility and dynamic exchange at the RNA-peptide interface (Puglisi et al., 1992; Aboul-ela et al., 1995; Brodsky & Williamson, 1997; Cai et al., 1998; De Guzman et al., 1998). These dynamic properties are, in theory, a severe hindrance to the development of FRET.

SUMMARY OF THE INVENTION

The invention provides a method for determining whether a test compound binds to a target RNA, the method comprising the steps of: (a) contacting the test compound with a pair of indicator molecules comprising a reporter labeled with a donor group or an acceptor group and the target RNA labeled with a complementary acceptor or donor group, the pair being capable of binding to each other in an orientation that permits the donor group to come into sufficient proximity to the acceptor group to permit fluorescent resonance energy transfer and/or quenching to take place; and (b) measuring the fluorescence of the target RNA and/or the reporter molecule in the presence of the test compound and comparing this value to the fluorescence of a standard.

In preferred embodiments, the standard comprises the indicator pair in the presence or absence of test compound, the fluorescently-labelled target RNA in the presence or absence of test compound, or fluorescently-labelled reporter molecule in the presence or absence of test compound. It will be appreciated that the fluorescence of the standard may have been determined before performing the method, or may be determined during or after the method has been performed. It may be an absolute standard.

The method may also be used in the identification of compounds that bind to the target RNA from within a plurality of test compounds, such as in screening methods. The method may, therefore, involve the initial step of providing a plurality of test compounds, which may include compounds not already known to bind to the target RNA sequence.

In a typical embodiment, therefore, the invention provides a method of screening for compounds that bind to a target RNA, comprising the steps of (a) contacting a test compound with an indicator complex, the indicator complex comprising a fluorescently-labeled reporter molecule bound to a fluorescently labeled target RNA in an orientation that permits the fluorescent groups present on each molecule to come into sufficient proximity to permit fluorescent resonance energy transfer to take place; and (b) measuring the fluorescence of the target RNA and the reporter molecule in the presence of the test compound and comparing this value to the fluorescence of a standard.

In preferred embodiments of the methods of the invention, the reporter molecule comprises a peptide, a protein, a lipid, a polysaccharide, or a small organic molecule. In other preferred embodiments, the reporter comprises a linear peptide or derivative thereof, a cyclic peptide or derivative thereof, a linear or cyclic peptoid or derivative thereof, or a peptidomimetic analogue. A reporter molecule also may comprise an oligonucleotide, or derivative thereof, that is able to form a complex with the target RNA under conditions where the RNA is not subject to unfolding (for example, it forms a complex with the target RNA by forming triple helices with the folded form of the target RNA).

Typically, the reporter binds the target RNA with a Kd of between $1\times10^{-12}$ and $1\times10^{-4}$ M, and the target RNA is between 5 and about 500 nucleotides in length.

In other embodiments, the target RNA is derived from fungal, viral, bacterial, or eukaryotic RNA, and may be chemically modified.

In a particularly preferred embodiment, the target RNA is a viral RNA from a region of the TAR of HIV.

In certain embodiments of the invention, the target RNA and reporter are selected from the following pairs:

| Target RNA | Reporter |
|---|---|
| SEQ IDs 1 & 2 | SEQ ID 5; |
| SEQ IDs 3 & 4 | SEQ ID 5; |
| SEQ ID 5 | SEQ ID 12; |
| SEQ ID 5 | SEQ ID 13; |

-continued

| Target RNA | Reporter |
|---|---|
| SEQ ID 6 | SEQ ID 11; |
| SEQ ID 6 | SEQ ID 13; |
| SEQ ID 7 | SEQ ID 11; |
| SEQ ID 7 | SEQ ID 12; |
| SEQ ID 5 | SEQ ID 15; |
| SEQ ID 6 | SEQ ID 14; |
| SEQ ID 7 | SEQ ID 14; and |
| SEQ ID 7 | SEQ ID 15. |

Preferably, the target RNA is a viral RNA from a region of the RRE of HIV.

In certain other embodiments, the target RNA and reporter are selected from the following pairs:

| Target RNA | Reporter |
|---|---|
| SEQ ID 8 | SEQ ID 14; |
| SBQ ID 8 | SEQ ID 15; |
| SEQ ID 9 | SEQ ID 15; and |
| SEQ ID 10 | SEQ ID 14. |

In other preferred embodiments, the target RNA and the reporter molecule are fluorescently labelled by covalent attachment of a fluorescent group. For instance, the target RNA may be fluorescently labelled at the 3' or 5' end of a strand within the target RNA, or within the chain of the target RNA.

It also may be preferred in some instances that the reporter molecule or the target RNA molecule is adhered to a solid support.

The invention also includes a method for determining the presence in a biological sample of a compound that binds to a target RNA molecule, comprising (a) contacting the sample with a pair of indicator molecules comprising a reporter labelled with a donor group or an acceptor group and the target RNA labelled with a complementary acceptor or donor group, the pair being capable of binding to each other in an orientation that permits the donor group to come into sufficient proximity to the acceptor group to permit fluorescent resonance energy transfer and/or quenching to take place; and (b) measuring the fluorescence of the target RNA and the reporter molecule as an indication of binding. Preferably in this method, said biological sample comprises a tissue or fluid from a mammal.

In the methods of the invention, it also is preferred that either (i) the donor is attached to the target RNA, and the acceptor is attached to the reporter molecule, or (ii) the donor is attached to the reporter molecule, and the acceptor is attached to the target RNA.

As used herein, the term "donor" refers to a fluorophore which absorbs at a first wavelength and emits at a second, longer wavelength. The term "acceptor" refers to a fluorophore, chromophore or quencher with an absorption spectrum which overlaps the donor's emission spectrum and is able to absorb some or most of the emitted energy from the donor when it is near the donor group (typically between 1–100 nm). If the acceptor is a fluorophore capable of exhibiting FRET, it then re-emits at a third, still longer wavelength; if it is a chromophore or quencher, then it releases the energy absorbed from the donor without emitting a photon. Although the acceptor's absorption spectrum overlaps the donor's emission spectrum when the two groups are in proximity, this need not be the case for the spectra of the molecules when free in solution. Acceptors thus include fluorophores, chromophores or quenchers that, following attachment to either the RNA target molecule or to the reporter molecule, show alterations in absorption spectrum which permit the group to exhibit either FRET or quenching when placed in proximity to the donor through the binding interactions of two molecules.

As used herein, references to "fluorescence" or "fluorescent groups" or "fluorophores" include luminescence and luminescent groups, respectively.

In other preferred embodiments, the acceptor is able to quench the fluorescence of the donor after binding of the target RNA and the reporter.

As used herein, the term "quenching" refers to the transfer of energy from donor to acceptor which is associated with a reduction of the intensity of the fluorescence exhibited by the donor. In certain preferred embodiments of the invention, only quenching of the donor due to the proximity of the acceptor in the reporter/RNA complex is measured. In certain embodiments of the invention, the target RNA carries a chromophore or fluorophore that quenches the fluorescence of the fluorescent group on the reporter after binding of the two molecules. In other embodiments of the invention, the reporter carries a chromophore or fluorophore that quenches the fluorescence of the fluorescent group on the target RNA after binding of the two molecules.

In some methods according to the invention, the target RNA, the reporter, and the test compound are mixed, and the fluorescence of the mixture is compared to standards. In other methods, the test compound is first mixed with the labelled RNA in order to form a complex in the absence of the labelled reporter, and the reporter is then added. Alternatively, a complex is pre-formed between the labelled RNA and the labelled reporter molecule before addition of the test compound.

The invention also encompasses a kit for determing whether a test compound binds to a target RNA, the kit comprising (a) a target RNA labelled with a donor group or an acceptor group and (b) a reporter labelled with a complementary acceptor or donor group, wherein the reporter and the target RNA are capable of binding to each other in an orientation that permits the donor group to come into sufficient proximity to the acceptor group to permit fluorescent resonance energy transfer and/or quenching.

Further features and advantages of the invention will become more fully apparent in the following description of the embodiments and drawings thereof, and from the claims.

BRIEF DESCRIPTION OF THE DRAWINGS

FIG. 2 shows the composition and sequence of fluorescently-labelled peptides derived from HIV Tat that are used as reporter molecules and the composition and sequence of the corresponding fluorescently-labelled TAR RNA target molecules that are used in the method to detect inhibitors of the Tat-TAR RNA interaction. The sequences depicted are: FIG. 2(a) Labelled ADP-1 Reporters (SEQ ID NO:7); FIG. 2(b) upper duplex: top strand (SEQ ID NO:1), lower strand (SEQ ID NO:2); lower duplex: top strand (SEQ ID NO.3), lower strand (SEQ ID NO.4); FIG. 2(c) TAR RNAs (SEQ ID NO:5).

FIG. 3 shows the composition and sequence of fluorescently-labelled peptides (SEQ ID NO:8) derived from HIV Rev that are used as reporter molecules and the composition and sequence of the corresponding fluorescently-labelled RRE RNA target molecules (SEQ ID NO:6) that are used in the method to detect inhibitors of the Rev-RRE RNA interaction.

FIG. 23 shows the quantitative data analysis for the samples shown in Table 4.

DESCRIPTION

Figure 1A:
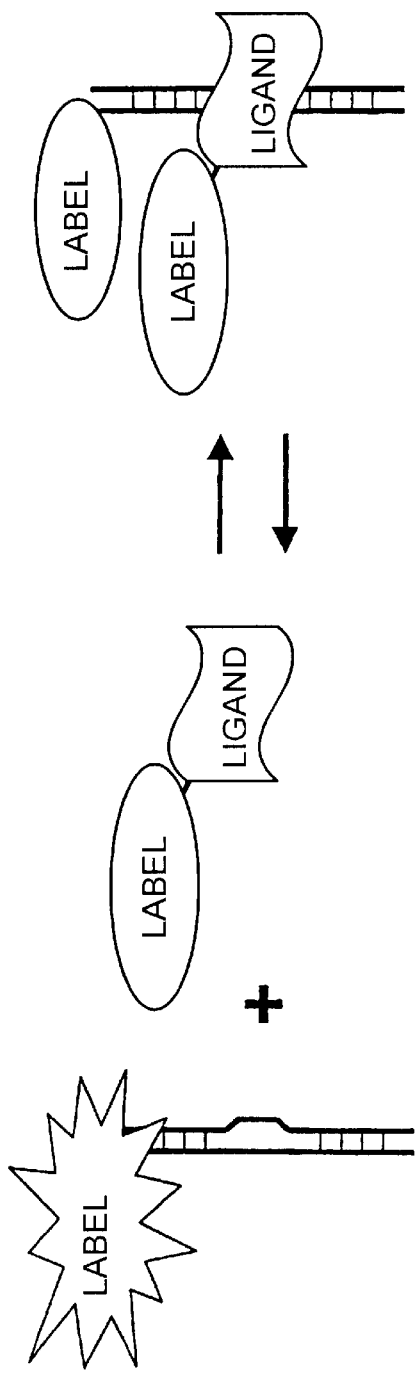
FIG. 1 is a schematic diagram depicting the method of the invention.
Figure 1B:
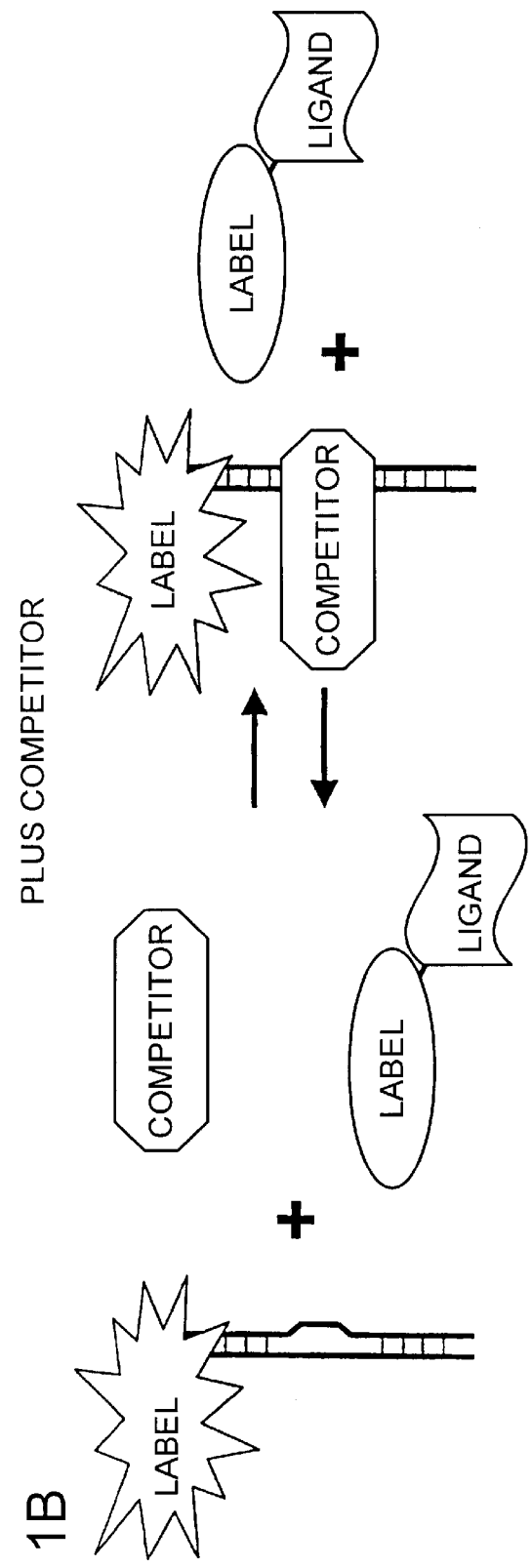

The invention pertains to a simple and robust solution-based assay designed to detect compounds that compete for RNA-binding with a reporter molecule. The invention is based on the unexpected finding that a labeled reporter molecule carrying a fluorescent or chromogenic group can form a stable one-to-one complex with a labeled RNA target molecule carrying a second fluorescent or chromogenic group to permit fluorescence resonance energy transfer (FRET) and/or quenching. Reporter molecules, such as peptides, can bind in fixed orientations with respect to the target RNA and, as outlined in FIG. 1, it is possible to obtain complexes of the reporter and target RNA with altered fluorescence properties.

The use of an appropriately positioned donor group on one molecule and acceptor group on a second molecule leads to significantly improved sensitivity and specificity in the assay and distinguishes this assay from previous approaches involving the use of only a single fluorescent group placed on either the target RNA or reporter molecule. These findings have been exploited to develop the present invention, which includes quantitative screening methods and kits for identifying RNA-binding compounds. The invention is described in detail below.

The Reporter Molecule

A "reporter molecule" useful according to the invention is capable of binding to the target RNA. It may bind at a particular site of interest, and preferably forms a one-to-one complex with the target RNA. Reporter molecules can thus be virtually any agent including, without limitation, peptides, peptoids, proteins, lipids, polysaccharides, and small organic molecules with molecular weights of more than 200 and less than about 2,500 daltons, preferably between 500 and 1,000 daltons. A reporter molecule useful according to the invention is not an oligonucleotide that has a sequence which is able to hybridize (i.e., is complementary via Watson-Crick base-pairing) under stringent conditions to an unfolded target RNA. The reporter molecule thus has a nucleotide sequence which prevents it from binding to the target RNA under conditions in which the target RNA is completely unfolded, but which permits it to bind to the target RNA under conditions in which the target RNA is folded (e.g., via triple helix formation). That is, the reporter may be an oligonucleotide or oligonucleotide derivative that is able to form a complex with the target RNA under conditions where the RNA is not subject to unfolding (for example, by forming triple helices). An oligonucleotide reporter molecule that binds to folded RNA target but not to the unfolded RNA target will not bind to an RNA target that has been subjected to heat denaturation at 90° C. for 2 minutes in binding buffer (50 mM Tris pH 7.5, 200 mM NaCl, and 10 mM $MgCl_2$) and chilled on ice for 2 minutes. In one aspect of the invention, the reporter molecule is not an oligonucleotide.

The reporter may bind the target RNA with a Kd of between $1\times10^{-12}$ and $1\times10^{-4}$ M. The reporter molecule may be a linear peptide or derivative thereof, a cyclic peptide or derivative thereof, a linear or cyclic peptoid or derivative thereof, or a peptidomimetic analogue. Linear peptides, or peptoids are between 2 and 100 residues in length, more advantageously between 4 and 40 residues in length, and even between 8 and 20 residues in length, and may comprise either D- or L-amino acids (or equivalents). Cyclic peptides, peptoids or their derivatives may be between 4 and 10 residues in length, for example, 4 to 7 residues in length, and may comprise either D- or L-amino acids (or equivalents). Peptoids are isomers of peptides which have side chains carried by backbone nitrogens (N-substituted glycines) (e.g. Bartlett, et al. WO91/19735, Zuckermann, et al. WO94/06451 and Simon et al., 1992). Peptoids are more flexible than peptides since intramolecular CO—HN hydrogen bonds are removed and the steric interactions that induce secondary structure are different.

The Target RNA

A "target RNA" useful according to the invention includes an RNA of interest which can be appropriately labeled (i.e., as described herein so as to provide FRET as fluoresence or quenching) and to which a suitable reporter can be bound. The target RNA may, for example, be derived from fungal, viral, bacterial, or eukaryotic RNA. RNAs useful according to the invention include sequences from the rRNAs and mRNAs of bacteria (Gram-negative or Gram-positive), mRNAs of viruses (such as HIV, influenza, rhinoviruses, hepatitis C, etc.), rRNAs and mRNAs derived from fungi (such as *Candida albicans, Pneumocystis carinii, Aspergilus fumigatis*/flavus) and rRNAs and mRNAs derived from humans and other mammals. The target RNA also may be a bacterial (eg. a ribosomal RNA) or viral RNA, or a region of an RNA from HIV, such as the TAR or the RRE, or suitable fragments thereof. A ribozyme is also suitable as a target RNA.

Target RNA sequences for use in the present invention are typically between 5 and about 500 nucleotides in length, preferably between about 20 and about 100 nt, and most preferably between about 20 and 50 nts. For example, the target RNA may comprise a chemically-synthesized oligonucleotide of between 20 and 100 nucleotides in length that is capable of folding to form a secondary structure present in the original RNA target. Alternatively, the target RNA structure may be created by the annealing of two or more oligonucleotides of between 10 and 100 nucleotides in length that are capable of creating a folded structure present in the original RNA structure. Examples of the use of pairs of oligonucleotides which, after annealing, are able to mimic a folded RNA target structure are given in Karn et al. (WO92/02228 and U.S. Pat. No. 5,821,046 (issued Oct. 13, 1998), describing mimics of the Tat binding site on TAR RNA) and Karn et al. (WO92/05195 and U.S. Pat. No. 5,786,145 (issued Jul. 28, 1998), describing mimics of the Rev binding site on RRE RNA). A synthetic analogue of a ribozyme formed by the annealing of a pair of oligonucleotides is described in Slim et al., (1991) and Grasby et al., (1993). An example of the use of three oligonucleotides, which after annealing, are able to mimic a folded RNA target structure is the TWJ6 mimic of the Rev binding site on RRE RNA (Iwai et al., 1992; WO92/05195).

The target RNA may be a natural or synthetic RNA.

Since oligoribonucleotides are sensitive to cleavage by cellular ribonucleases, as well as to alkaline or acid conditions, it may be preferable to use as the RNA target molecule a chemically modified molecule that mimics the action of the RNA binding sequence but is more stable. Other modifications may also be desirable to provide groups for immobilizing the RNA target oligonucleotide on solid supports by covalent or non-covalent attachments. The RNA target oligonucleotide may be a naturally occurring oligonucleotide, or may be a structurally related variant of such an oligonucleotide having modified bases and/or sugars and/or linkages. The terms "RNA target" or "RNA target oligonucleotides" or "RNA oligonucleotides" as used herein are intended to cover all such variants.

Modifications, which may be made either into the binding site per se or to a part of the RNA target oligonucleotide that does not inhibit binding of the reporter molecule, may include, but are not limited to the following types:
a) Backbone modifications:
   (i) phosphorothioates (single S substituents or any combination of two or more with the remainder as O (Stein et al., 1988; Cosstick, 1990 #28; Caruthers, 1989 #27);
   (ii) methylphosphonates (Miller et al., 1980);
   (iii) phosphoramidates (Agrawal et al., 1988; Mag & Engels, 1988);
   (iv) phosphotriesters (Miller et al., 1982); and
   (v) phosphorus-free linkages (e.g. carbamate, acetamidate, acetate), (Gait et al., 1974);
b) Sugar modifications:
   (i) 2'-deoxynucleosides (R=H);
   (ii) 2'-O-methylated nucleosides (R=OMe; (Sproat et al., 1989));
   (iii) 2'-fluoro-2'-deoxynucleosides (R=F; (Schmidt et al., 1992)); and
   (iv) 2'-O-alkylated nucleosides (Sproat et al., 1991);
c) Base modifications (for a review see Gait et al., 1998):
   (i) pyrimidine derivatives substituted in the 5-position (e.g. methyl, bromo, fluoro etc. or replacing a carbonyl group by an amino group, (Piccirilli et al., 1990); and
   (ii) purine derivatives lacking specific nitrogen atoms (e.g. 7-deaza-adenine, hypoxanthine, or functionalised in the 8-position (e.g. 8-azido adenine, 8-bromo adenine), or additional functionalities (e.g. 2,6-diaminopurine (Lanim et al., 1991));
d) Oligonucleotides covalently linked to reactive functional groups (e.g. psoralens, (Lee et al., 1988); phenanthrolines, (Sun et al., 1988); mustards, (Vlassov et al., 1988));
e) irreversible cross-linking agents with or without the need for co-reagents)
   (i) acridine (intercalating agents, (Hélene et al., 1985));
   (ii) thiol derivatives (reversible disulphide formation with proteins, (Connolly & Newman, 1989));
   (iii) aldehydes (Schiff's base formation);
   (iv) azido, bromo groups (UV cross-linking); and
   (v) ellipticenes (photolytic cross-linking, (Perrouault et al., 1990);
f) oligonucleotides containing haptens or other binding groups;
g) fluorescent moieties or other non-radioactive labels (Tuschl et al., 1994); and h) combination of two or more modifications selected from a to g Regions of the target RNA selected for binding to the reporter include, but are not limited to, sequences bound by an RNA-binding protein and sequences with specific secondary structures formed by bulges, internal loops and junctions etc.

Particular representative target RNA oligonucleotides derived from the HIV TAR sequence and known to be bound by suitable reporter molecules are set out in the Sequence listing as SEQ ID NOS: 1 and 2 (annealed); SEQ ID NOS: 3 and 4 (annealed); SEQ ID NO: 5 (labelled with Cy3, FAM or DABCYL); and shown in FIG. 2. Particular representative reporter molecules that can bind the HIV TAR sequence are set out in the Sequence listings as SEQ ID NO: 7 (labelled with TAMRA, FAM or DABCYL) and shown in FIG. 2.

As used herein, a sequence that has been labelled is referred to by the label followed by the sequence ID NO., for example, SEQ ID FAM-2 refers to a FAM labelled version of SEQ ID NO. 2, SEQ ID Cy3–5 refers to a Cy3-labelled version of SEQ ID NO. 5, SEQ ID DABCYL-7 refers to a DABCYL labelled version of SEQ ID NO. 7 and SEQ ID TAMRA-7 refers to a TAMRA labelled version of SEQ ID NO. 7.

Particular representative RNA oligonucleotides derived from the HIV RRE sequence and known to be bound by suitable reporter molecules are set out in the sequence listings as SEQ ID NO: 6 (labelled with DABCYL, Cy3, FAM) and shown in FIG. 2. Particular representative reporter molecules that can bind the HIV RRE sequence are set out in the sequence listings as SEQ ID NO: 8 (labelled with TAMRA or FAM) and shown in FIG. 3.

Fluorescent Labeling

The target RNA and the reporter molecule may be fluorescently labeled for use according to the invention by any suitable method, preferably by covalent attachment of a fluorescent group. The labels may be any fluorescent label or fluorophore that does not interfere with the ability of the reporter to interact with the target RNA and is able to show quenching and/or fluorescence resonance energy transfer with the corresponding label on the target RNA.

The target RNA may be fluorescently labeled at any suitable position. For instance, the fluorescent group or quenching group is placed on or adjacent to the 5' end of the target RNA. Alternatively, the fluorescent or quenching group is placed on or adjacent to the 5' end of one of a pair of oligonucleotides forming an RNA duplex, or the 5' end of one of the component oligonucleotides in RNA structure created by the annealing of three or more RNA oligonucleotides. In other instances, the fluorescent group may be placed on or adjacent to the 3' end of one of the synthetic RNA molecules.

The fluorescent group also may be placed within the chain of the synthetic RNA molecules, for instance by incorporation of a fluorescent nucleotide derivative, modification of a nucleotide or substitution of a nucleotide by a fluorescent molecule. For example, tetramethylrhodamine (TAMRA) can be introduced into synthetic RNA by incorporating the modified deoxy-uridine phosphoraridite (5'-Dimethoxytrityloxy-5-[N-((tetramethyl-odaminyl)-aminohexyl)-3-acryimido]-2'-deoxy-uridine-3'-[(2-cyanoethyl)-(N,N-diisopropyl)]-phosphoramidite). Fluorescein may be incorporated in an analogous way with: 5'-Dimethoxytrityloxy-5-[N-((3',6'-dipivaloylfluoresceinyl)-aminohexyl)-3-acryimido]-2'- deoxy-uridine-3'-[(2-cyanoethyl)-(N,N-diisopropyl)]-phosphoramidite. The DABCYL group may also be incorporated using 5'-Dimethoxytrityloxy-5-[N-((4-(dimethylamino)azobenzene)-aminohexyl)-3-acryimido]-2'-deoxy-uridine-3'-[(2-cyanoethyl)-(N,N-diisopropyl)]-phosphoramidite. More generally, a free amino group may be reacted with the active ester of any dye; such an amino group may be introduced by the inclusion of the modified uridine 5'-Dimethoxytrityl-5-[N-(trifluoroacetylaminohexyl)-3-acrylimido]-2'-deoxy-uridine,3'-[(2-cyanoethyl)-(N,N-diisopropyl)]-phosphoramidite. The incorporation of a single deoxy-uridine often does not significantly perturb RNA structure and the modification at the 5 position of the base allows for normal base-pairing.

It is also possible to include more than one fluorescent label on a synthetic RNA target molecule without departing from the scope the invention. For instance, a target RNA molecule is labelled with 2 fluorescent groups, with one group placed adjacent to the 5' end of the target RNA sequence and a second fluorescent group placed adjacent to the 3' end of the target RNA sequence. In other embodiments, two or more fluorescent groups are placed adjacent to the 5' and/or 3' ends of the target RNA molecule and/or at internal sites in the RNA target sequences. Multiply labelled target RNAs can be used to increase the intensity of the signals detected in the assay.

In some instances, a target RNA labelled at 2 or more positions may be used to detect interactions with two or more reporter molecules. The reporter molecules can either be used individually or simultaneously. Alternatively, an RNA molecule labelled at two or more positions is used to detect binding of reporters (and inhibition of binding by test molecules) to distinct and specific regions on the target RNA. In other instances, the binding of more than one reporter to a single site on the target RNA, or to two or more overlapping sites on the target RNA may be detected.

The reporter molecule may also be labelled at any suitable position. When peptides or peptoids are used as reporter molecules, the fluorescent group may, for instance, be placed at either the carboxyl or amino terminus of the molecule. In other instances, using peptides or peptoids the fluorescent group may be placed on a side chain within the peptide or peptoid sequence.

It is also possible to include more than one fluorescent label on the reporter molecule without departing from the scope the invention. Multiply labelled reporter molecules can be used to enhance signal intensity and/or selectivity. These can be used in conjunction with singly-labelled target RNAs or with the multiply-labelled target RNA molecules described above.

Useful fluorophores (in addition to those listed in Tables 1 and 2) include, but are not limited to: Texas Red™ (TR), Lissamine™ rhodamine B, Oregon Green™ 488 (2',7'-difluorofluorescein), carboxyrhodol and carboxyrhodamine, Oregon Green™ 500, 6-JOE (6-carboxy-4',5'-dichloro-2',7'-dimethyoxyfluorescein), eosin F3S (6-carobxymethylthio-2',4',5',7'-tetrabromo-trifluorofluorescein), cascade blue™ (CB), aminomethylcoumarin (AMC), pyrenes, dansyl chloride (5-dimethylaminonaphthalene-1-sulfonyl chloride) and other napththalenes, PyMPO, ITC (1-(3-isothiocyanatophenyl)-4-(5-(4-methoxyphenyl)oxazol-2-yl) pyridinium bromide).

Donor/acceptor Pairing

Contact between the pair of indicator molecules may occur in solution (e.g., a test tube, dish or well of a microtitre plate) or, alternatively, either the reporter molecule or the target RNA molecule may be adhered to a solid support (eg. an affinity gel, matrix, or column) by covalent or non-covalent linkages using methods known in the art. The support bound target or reporter molecule is then mixed with a solution containing the other compound of the indicator pair.

When the reporter and RNA target are mixed, they can form a complex which brings the donor and acceptor groups into proximity. The "fluorescence" of, or light emitted from, the complex formed between the reporter molecule and the target RNA is altered by fluorescence resonance energy transfer (FRET). "FRET" is a distance-dependent interaction between the electronic exited states of two dye molecules in which excitation is transferred from a donor molecule to an acceptor molecule. FRET is dependent on the inverse sixth power of the intermolecular separation, making it useful over distances comparable to the dimensions of biological macromolecules and obtainable in the complexes formed between the reporter molecules and target RNA molecules in the method of this invention. In most embodiments, the donor and acceptor dyes for FRET are different, in which case FRET can be detected by the appearance of sensitized fluorescence of the acceptor and/or by quenching of donor fluorescence. When the donor and acceptor are the same, FRET is detected by the resulting fluorescence depolarization.

The donor group may be attached to either the target RNA or to the reporter molecule. When the donor is attached to the target RNA, the complementary acceptor is attached to the reporter molecule; conversely, when the donor is attached to the reporter molecule, the complementary acceptor is attached to the target RNA.

The donor and acceptor groups may independently be selected from suitable fluorescent groups, chromophores and quenching groups. Donors and acceptors useful according to the invention include but are not limited to: 5-FAM (also called 5-carboxyfluorescein; also called Spiro (isobenzofuran-1(3H), 9'-(9H)xanthene)-5-carboxylic acid, 3',6'-dihydroxy-3-oxo-6-carboxyfluorescein); 5-Hexachloro-Fluorescein ([4,7,2',4',5',7'-hexachloro-(3',6'-dipivaloyl-fluoresceinyl)-6-carboxylic acid]); 6-Hexachloro-Fluorescein ([4,7,2',4',5',7'-hexachloro-(3',6'-dipivaloylfluoresceinyl)-5-carboxylic acid]); 5-Tetrachloro-Fluorescein ([4,7,2',7'-tetra-chloro-(3',6'-dipivaloylfluoresceinyl)-5-carboxylic acid]); 6-Tetrachloro-Fluorescein ([4,7,2',7'-tetrachloro-(3',6'-dipivaloylfluoresceinyl)-6-carboxylic acid]); 5-TAMRA (5-carboxytetramethylrhodamine; Xanthylium, 9-(2,4-dicarboxyphenyl)-3,6-bis(dimethyl-amino); 6-TAMRA (6-carboxytetramethylrhodamine; Xanthylium, 9-(2,5-dicarboxyphenyl)-3,6-bis(dimethylamino); EDANS (5-((2-aminoethyl) amino)naphthalene-1-sulfonic acid); 1,5-IAEDANS (5-((((2-iodoacetyl)amino)ethyl)amino) naphthalene-1-sulfonic acid); DABCYL (4-((4-(dimethylamino)phenyl)azo)benzoic acid) Cy5 (Indodicarbocyanine-5) Cy3 (Indo-dicarbocyanine-3); and BODIPY FL (2,6-dibromo-4,4-difluoro-5,7-dimethyl-4-bora-3a,4a-diaza-s-indacene-3-proprionic acid), as well as suitable derivatives thereof.

According to some methods of the invention, the RNA target molecule has been specifically labelled by a donor/acceptor that is different from the acceptor/donor that is present on the reporter molecule. Preferred combinations of donors and acceptors are listed as, but not limited to, the donor/acceptor pairs shown in Tables 1 and 2 (which includes values for $R_0$-the distance at which 50% of excited donors are deactivated by FRET).

Reference herein to "fluorescence" or "fluorescent groups" or "fluorophores" include luminescence, luminescent groups and suitable chromophores, respectively. In the present invention, the target RNA and reporter molecule may be labelled with luminescent labels and luminescence resonance energy transfer is indicative of complex formation. Suitable luminescent probes include, but are not limited to, the luminescent ions of europium and terbium introduced as lanthium chelates (Heyduk & Heyduk, 1997). The lanthanide ions are also good donors for energy transfer to fluorescent groups (Selvin 1995). Luminescent groups containing lanthanide ions can be incorporated into nucleic acids utilizing an 'open cage' chelator phosphoramidite. Table 2 gives some preferred luminescent groups.

In certain embodiments of the invention, the target RNA and reporter molecule may also be labelled with two chromophores, and a change in the absorption spectra of the label pair is used as a detection signal, as an alternative to measuring a change in fluorescence.

Measurable Changes

In the method of the present invention, the labelled reporter is capable of binding to the labelled target RNA, thereby forming a complex in which the donor present on one molecule comes into proximity with the acceptor on the other molecule. This results in reduced fluorescence of the complex compared to the uncomplexed fluorescence exhibited by the reporter molecule and/or target RNA when free in solution.

In the method of the invention, fluorescence intensity of the reporter molecule, the fluorescence intensity of the RNA target and the fluorescence intensity of the complex is measured at one or more wavelengths with a fluorescence spectrophotometer or microtitre plate reader. It is generally preferred that the reporter molecule and RNA target form a one-to-one complex and equimolar concentrations of reporter molecule and RNA target are present in the binding reaction. However, an excess of one reagent may be used without departing from the scope of the invention.

In some embodiments, a fraction of the reporter molecules and RNA target molecules in the binding reaction can be replaced by unlabelled analogues. The optimal proportions of labelled and unlabelled reporter and RNA target molecules can be determined by titration of the different components and measuring the optimal concentrations required in order to obtain maximal FRET or fluorescent quenching.

The labelled RNA and labelled reporter molecules are then mixed with a test compound and the fluorescence in the mixture is measured. If the test compound is able to bind to the region of the target RNA that binds to the reporter molecule, then a fraction of the reporter molecule will be prevented from binding to the RNA target. The proportions of the free reporter, free test RNA and complex can be quantitatively determined by comparing the spectral properties of the complex, partially dissociated complex and the uncomplexed target RNA and reporter molecules. The amount of reporter displacement will be a function of the relative affinity of the test compound for the target RNA compared to the reporter molecule and the relative concentrations of the two molecules in the sample. Preferably, a variety of different concentrations of the molecule to-be-tested are compared to generate a binding curve. Saturation of the target RNA is reached when the fluorescence emission of the reporter or RNA target molecule is restored to the levels obtained from the free molecules.

The concentration of compounds binding to RNA targets can be determined with a fluorescence standard curve depicting the fluorescence of the labelled reporter and target RNAs with varying known concentrations of competing unlabelled test compound.

In some embodiments of the invention, fluorescence resonance energy transfer between the donor and acceptor may give rise to a distinct fluorescence emission spectrum of the complex which can be compared to the fluorescence emission spectra of the separate reporter and target RNA molecules.

In some embodiments of the invention, FRET is detected by steady state measurements of the integrated emission intensity of the donor (ie. the fluorescent dye that is excited by the light source used in the spectral measurement) and/or the acceptor (ie. the fluorescent dye which has a absorption spectrum that overlaps the emission spectrum of the donor). In addition, FRET may be detected by time-resolved measurements in which the decay of donor fluorescence is measured after a short pulse of excitation. In certain embodiments of the invention the donor is excited at a wavelength that does not itself result in efficient excitation of the acceptor, and FRET is detected by measuring the excitation of the acceptor due to transfer of a photon from the donor.

Typically, it is preferable to look for a signal (a positive), rather than for the absence of a signal (a negative) in an assay of the invention, but it will be appreciated that either or both may be followed.

Test Compound

The present invention may be used to identify a compound capable of binding to any target RNA, preferably as part of a screening process.

As used herein, the term "test compound" refers to an agent comprising a compound, molecule, or complex, that is being tested for its ability to bind to a target RNA. Test compounds can be any agent, including, but not restricted to, peptides, peptoids, proteins, lipids, metals, nucleotides, nucleosides, small organic molecules, antibiotics, polyamines, and combinations and derivatives thereof. Small organic molecules have a molecular weight of more than 50 and less than about 2,500 daltons, and most preferably between about 300 and about 800 daltons. Complex mixtures of substances, such as extracts containing natural products, or the products of mixed combinatorial syntheses, can also be tested and the component that binds to the target RNA can be purified from the mixture in a subsequent step.

Test compounds may be derived from large libraries of synthetic or natural compounds. For instance, synthetic compound libraries are commercially available from Maybridge Chemical Co. (Trevillet, Cornwall, UK) or Aldrich (Milwaukee, Wis.). Alternatively, libraries of natural compounds in the form of bacterial, fungal, plant and animal extracts may be used. Additionally, test compounds may be synthetically produced using combinatorial chemistry either as individual compounds or as mixtures.

Order of Mixing

A significant advantage of the method of the invention is that it measures equilibrium binding, which is only approximated by the filter binding, gel mobility shift, scintillation proximity or mass spectrometry assays described above. The invention also exploits the principle that the most reliable type of assays for RNA-binding compounds are based on competition assays between the RNA-binding protein and the drug candidates.

In preferred embodiments of the invention, the target RNA, the reporter, and the test compound are mixed, and the fluorescence of the mixture is compared to standards. Competitive inhibitors of the binding of the reporter molecule prevent the formation of the reporter-target complex and therefore increase the amount of free target RNA and free reporter in the reaction. Since the fluorescence of the free RNA and reporter molecules is unquenched, the overall fluorescence in the reaction increases in direct relation to the amount of test compound in the binding reaction and its relative affinity for the target RNA compared to the reporter molecule.

In some embodiments of the invention, the test compound is first mixed with the labelled RNA in order to form a complex in the absence of the labelled reporter, and the reporter is then added. Since the reporter molecule will only be able to bind to the free RNA in the reaction, there will be a reduced amount of complex formed between the reporter and the target RNA compared to the amount of complex formed in the absence of test compound. As a result, the fluorescence of the mixture containing the test compound will be increased compared to a similar mixture prepared in the absence of the test compound.

In other embodiments, a complex is pre-formed between the labelled RNA and the labelled reporter molecule before addition of the test compound. If the test compound is able to disrupt the complex formed between the labelled-RNA and the labelled-reporter molecule, or alter the equilibrium binding state by binding to RNA that has dissociated from the reporter molecule, the amount of complex in the reaction will be reduced and the overall fluorescence of the mixture will increase.

In some circumstances, the test compound may itself be fluorescent and/or be capable of quenching the fluorescent group present on the target RNA and/or the reporter molecule. In preferred embodiments of the invention, the fluorescence of standards containing the test compound on its own, and in pairwise combinations with the target RNA or reporter molecules, are measured and these values are compared to the fluorescence of the complete test mixture containing the test compound, the fluorescent RNA and the reporter molecule.

Quenching of fluorescence arising from the RNA due to the binding of the test compound to the RNA will result in a decrease in the signal arising from the RNA that is not complexed to the reporter molecule, but will not affect the fluorescent signal arising from the group on the reporter molecule or the signal obtained from the RNA in a complex with the reporter molecule. In this circumstance it is preferable to configure the donor/acceptor pairs on the RNA and the reporter molecule such that an increase in the fluorescence of the reporter molecule is detectable when the formation of the complex between the reporter and the RNA is blocked by the test compound.

Quantitative Nature of the Assay

An important feature of the invention is that the test compound competes for RNA binding against a specific pre-defined reporter. This provides specificity in the assay and permits exclusion of compounds that bind to the target RNA but do not interfere with the binding of the reporter molecule. In preferred embodiments, the reporter molecules are designed to bind to discrete regions in the target RNA that are involved in biological activity or function, to permit identification of compounds that are likely to have biological or pharmaceutical activity.

The invention allows the measurement of the dissociation constant ($K_d$) between the reporter and the target RNA. $K_d$ is defined by equation [1]:

$$K_d = \frac{[R_f][P_f]}{[RP]}$$

Where $[R_f]$ is the concentration of free RNA, $[P_f]$ is the concentration of free reporter, and $[RP]$ is the concentration of the complex.

$K_d$ may be determined experimentally by incubating a pre-determined concentration of target RNA together with a series of concentrations of reporter molecule. An increase in the formation of complexes of the reporter molecule and the target RNA in solution results in a progressive increase in FRET and/or quenching. As the concentration of reporter increases the spectral values approach a maximal value asymptotically due to the formation in solution of the reporter-target RNA complex. In some embodiments of the invention the $K_d$ of a reporter molecule is determined by incubating a pre-determined concentration of reporter molecule together with a series of concentrations of target RNA.

The value for $K_d$ is preferably determined by fitting the experimental data to a binding curve derived from equation [1] by least-squares fit regression analysis. Alternatively, $K_d$ values can be approximated by graphical analysis of the data using double reciprocal (Scatchard) or similar plots. $K_d$ values are physical-chemical constants that define the affinity between the reporter molecule and the target RNA. The relative affinities of different reporter molecules for target RNAs may be determined by comparing measured $K_d$ values.

In preferred embodiments, the binding constant of a test compound relative to the reporter molecule ($K_i$), is measured by incubating a pre-determined concentration of target RNA and reporter molecules, together with a series of different compound concentrations. The concentrations of target RNA and reporter molecules are chosen to give a measurable amount of complex formation; preferably greater than 10% complex formation and most preferably greater than 50% complex formation. The most preferable starting conditions are obtained using equimolar concentrations of reporter and target RNA molecules at concentrations that are greater than $5 \times K_d$ of the reporter-target RNA. Under these circumstances essentially all of the reporter molecule and target RNA is found in the complex.

$K_i$ is then determined by measuring the inhibition of complex formation as a function of the amount of test compound added. A formal description of the binding equilibrium is as follows:

$$[R]+[P]=[RP]; [R]+[I]=[RI]$$

where $[R]$ is the target RNA concentration, $[P]$ is reporter concentration, $[I]$ is the inhibitor (i.e., test compound) concentration, $[RP]$ is the concentration of the complex formed between the reporter and the target RNA; and $[RI]$ is the concentration of the complex formed between the test compound and the target RNA. It follows that:

$$K_d = \frac{[R_f][P_f]}{[RP]}$$

and $$K_i = \frac{[R_f][I_f]}{[RI]}$$

where $K_d$ is the dissociation constant between the target RNA and the reporter, $K_i$ is the dissociation complex between the test compound and the target RNA, $[R_f]$ is the free RNA concentration; $[P_f]$ is the free reporter concentration; and $I_f$ is the free test compound (inhibitor) concentration.

Hence $[R_f]=[R]-[RP]-[RI]$;

$[P_f]=[P]-[RP]$; and $[I_f]=[I]-[RI]$.

Combining the equations yields the cubic equation [2] in which $K_d$ and $K_i$ are related to the experimentally determined values for [R], [P], [I] and [RP]:

$[RP]^3(K_d-K_i)$ $+[RP]^2\{K_d(K_i-K_d)+(K_i-K_d)[R]+(2K_i-K_d)[P]+K_d[I]\}$ $+[RP][P]\{(K_d-2K_i)[R]-K_i[P]-K_d[I]-K_dK_i\}$ $+K_i[R][P]^2=0$      equation [2]

Solutions of equation [2] by regressional analysis yield values for $k_i$. However, in practice, it is preferable to simplify equation [2] to a quadratic equation by approximating certain of the starting conditions. A typical simplification occurs when $K_i>>K_d$ and therefore the experimental inhibitor concentration is much greater than the total RNA, under conditions where the reporter is partially displaced from the RNA by inhibitor, hence, $[I_f]\approx\{I\}$. Reworking the above derivation, with this simplification, then yields the quadratic equation:

$$K_d\left(I+\frac{[I]}{K_i}\right)+[P]+[P][R]=0 \quad \text{equation [3]}$$

which has the solution $$[RP]=\frac{\left[K_d\left(I+\frac{[I]}{K_i}\right)+[P]+[R]\right]-\sqrt{\left[K_d\left(I+\frac{[I]}{K_i}\right)+[P]+[R]\right]^2-4[P][R]}}{2} \quad \text{equation [4]}$$

If a value of $K_d$ has already been determined for the reporter, values of $K_i$, for various inhibitors can be determined by non-linear regression analysis of data of [RP] against [I].

An alternative method to estimate $K_i$, which has been applied in the examples given below, is to fit the data to the equation:

$FI=[B_{max}][K_i]+[I]$ where: FI is the experimentally measured fluorescence intensity; $B_{max}$ is the maximal fluorescent signal (determined by measuring the fluorescence of the reporter molecule combined with inhibitor); and [I] is the inhibitor concentration. This simplified method ignores the effect of reporter binding on reducing the free RNA concentration, but is a useful simplification when $K_i>>K_d$.

Library Screening (Including High Throughput Screens)

The present invention also encompasses high-throughput screening methods for identifying compounds that bind to a target RNA. Preferably, all the biochemical steps for this assay are performed in a single solution in, for instance, a test tube or microtitre plate, and the test compounds are analyzed initially at a single compound concentration. For the purposes of high throughput screening, the experimental conditions are adjusted to achieve a proportion of test compounds identified as "positive" compounds from amongst the total compounds screened. The assay is preferably set to identify compounds with an appreciable affinity towards the target RNA e.g., when 0.1% to 1% of the total test compounds from a large compound library are shown to bind to a given target RNA with a $K_i$ of 10 μM or less (e.g. 1 μM, 100 nM, 10 nM, or less).

Kits Useful According to the Invention

The invention also provides a kit for determining whether a test compound binds to a target RNA, the kit comprising (a) a target RNA labelled with a donor group or an acceptor group and (b) a reporter labelled with a complementary acceptor or donor group, wherein the reporter and the target RNA are capable of binding to each other in an orientation that permits the donor group to come into sufficient proximity to the acceptor group to permit fluorescent resonance energy transfer and/or quenching. The kits will include the components useful in the inventive methods, as well as packaging materials therefor.

Methods of Identifying Reporter Molecules

Methods of the invention require a suitable reporter molecule. Where there is little or no information about natural ligands for a particular target RNA, it will therefore be necessary to identify a suitable reporter molecule. Another aspect of the invention is a method for identifying a reporter molecule from a mixture (eg. a combinatorial library) of labeled peptides, peptoids or other polymers carrying side chains. In one example of such a method, a series of peptides or peptoids between 3 and 100 residues in length are synthesized with a mixed collection of side chains (containing either natural amino acid side chains or sequence variants) at several positions within the sequence (eg. Felder et al., WO96/40759, and Hamy et al., 1997) and a fluorescent moiety (either a donor or acceptor) is placed at either the C-terminal or N-terminal end.

The individual compounds are then mixed in solution with the target RNA of interest that has been labelled with a complementary donor or acceptor. Complexes between the individual test compound and the target RNA are detected by measuring quenching and/or fluorescence resonance energy transfer. Preferably, the compounds are tested over a range of different concentrations (between 10 nM and 1 mM) and the RNA is at a fixed concentration (between 10 nM and 100 nM). The compounds are then ranked by calculating $K_d$ for each compound and the target RNA pair. The compound with the lowest $K_d$ is then selected for use as a reporter.

In a preferred embodiment of the invention the reporter molecule library comprises a series of linear peptides of 13 residues with the sequence:

DABCYL-Thr-Arg-Lys-X-X-X-X-X-Arg-Lys-Gly-Ser-Gly (SEQ ID NO: 10) where X is selected from the following amino acids: Arg, Lys, Gln.

This produces a total of 243 peptides from which a reporter molecule may be selected by measuring the degree of fluorescence quenching obtained when mixed with a target RNA sequence labelled with a fluorescent group such as FAM.

In other embodiments of this method the reporter molecules to be tested are cyclic peptides or peptoids of between 4 and 7 residues in length and carrying a fluorescent moiety placed on one of the side chains. In other embodiments of this method the reporter molecules to be tested are mixed polymers composed of 3 to 100 monomeric subunits and carrying a donor or acceptor group at a unique position.

In a preferred embodiment of the invention, the reporter molecule is selected from these libraries using a deconvolution scheme analogous to that described by Houghten et al. (1991) and Blake (U.S. Pat. No. 5,565,325, issued Oct. 15, 1996). In the first step, a series of sub-libraries, each of which contains a unique residue at the first position under investigation (residue A) and randomized sequences at the remaining positions (residues B, C, D, . . . etc.) are tested for binding to a target RNA carrying a fluorescent group by the method of the invention, and the sub-library showing the highest activity is identified. This defines the optimal side chain for the first residue (residue A). A new set of sub-libraries are synthesized, each of which contains the optimal residue A, a unique sequence at residue B, and randomized sequences at the remaining residues. Continuing with this approach it is possible to progressively limit the complexity of each sub-library and to identify optimal residues at each position. After a series of deconvolution cycles corresponding to each of the randomized residues, a single compound with optimal affinity for the target RNA can be identified.

In another aspect of the invention, cyclic peptides are used as reporter molecules. Unlike linear peptides, cyclic peptides are conformationally constrained. Fixing the active conformation in cyclic peptides can increase their affinity for RNA. Kessler et al. (1996) and von Roedern et al. 1996) have described the concepts for the design of libraries of conformationally constrained cyclic peptides. In brief, most cyclic tetrapeptides exhibit a cis-trans-cis-trans peptide bond configuration resulting in both chair and boat type configurations. Most cyclic pentapeptides prefer all-trans amide configurations producing five-membered rings that resemble cyclopentane. Cyclic hexapeptides normally adopt all trans configuration about the peptide bond and prefer a conformation with two β-turns. In general, the conformation of cyclic hexapeptides and pentapeptides is strongly influenced by the chirality of the amino acids. For example, a D-amino acid in a cyclic pentapeptide or hexapeptide strongly prefers the i+1 position of a βII' turn. This can be applied to force a sequence of amino acids into a specific position of the β-turn on the other side of the ring. If the optimal configuration of the cyclic peptides is not known, the spatial orientation of pharmacophoric groups on a distinct backbone conformation can be systematically screened by substituting one (or more) D-amino acid(s) at various positions in the sequence. The functional groups of the side-chains and their neighborhood are retained but their spatial arrangement can be adjusted by this procedure. If the conformation of the selected peptide matches the optimal bound conformation increased binding affinity can be expected. In addition, the constraints often prevent binding to related RNA sequences resulting in higher selectivity. For pharmacological applications, cyclic peptides have the advantage of increased resistance to proteases.

Another aspect of the invention is to address the interaction between a fluorescent reporter molecule and an RNA sequence obtained from an RNA diversity library. SELEX (Tuerk et al., 1992; Gold et al., 1995; Gold and Tuerk U.S. Pat. No. 5,270,163 issued Dec. 14, 1993 and U.S. Pat. No. 5,475,096 issued Dec. 12, 1995) is a technology for the generation and identification of high affinity oligonucleotide ligands from large libraries of random sequence single-stranded oligonucleotides. Selected RNA molecules can bind to a surprising variety of molecular targets, including nucleic acid binding proteins such as polymerases and transcription factors, non-nucleic acid binding proteins such as cytokines and growth factors, as well as small organic molecules such as ATP and theophylline (Jensen et al., 1994; Yang et al., 1996; Burke et al., 1997).

Measurements of RNA Binding Compound

The invention may be embodied as a clinical assay or method for determining the presence of an RNA-binding compound in a biological sample such as the serum or tissues of a subject. Many drugs, including RNA-binding compounds such as aminoglycoside antibiotics, are routinely assayed for their serum levels when administered to patients to prevent administration of toxic levels of compounds.

The invention thus provides a method for determining the amount of a predetermined RNA-binding compound in a subject or biological sample. In this method a complex consisting of a labelled target RNA specifically bound to a labelled reporter is mixed with a sample to be analysed (e.g., a serum sample or tissue extract from a subject). The level of RNA-binding compound in the sample is determined by comparing the level of fluorescence emitted by the labelled target RNA and/or labelled reporter in the presence of the sample with the level of fluorescence obtained using a known amount of the RNA-binding compound of interest. In some embodiments of this method, the reporter is unrelated to the RNA-binding compound of interest; in other embodiments it is a fluorescent version of the compound of interest.

The invention also provides a kit for determining the level of an RNA-binding compound of interest in a subject or sample, comprising (a) RNA labelled with a donor group or an acceptor group and which is specifically bound by the compound of interest (b) a reporter labelled with a complementary acceptor or donor group, wherein the reporter and the target RNA are capable of binding to each other in an orientation that permits the donor group to come into sufficient proximity to the acceptor group to permit fluorescent resonance energy transfer and/or quenching. The kit preferably further ;comprises a sample of the compound of interest in unlabelled and uncomplexed form, with which to prepare a standard fluorescence curve.

Typically, a serum or blood sample, or a tissue extract, is taken from a patient and contacted with the complex. The fluorescence of the complex is then measured and compared to a standard curve depicting the fluorescence of the complex in the presence of known concentrations of the RNA-binding compound of interest.

In this, and other, aspects of the invention, it may be desirable to add a ribonuclease inhibitor to the sample or to the mixture of the sample and complex to prevent degradation of the RNA. As an alternative, the fluorescently labelled target RNA could be protected by the inclusion of modified bases, sugars or backbone modifications as described above.

EXAMPLES

The following examples illustrate the preferred modes of making and practicing the present invention, but do not limit the scope of the invention.

The method of the invention is illustrated by a method for identifying compounds that bind to the TAR region of HIV RNA. It is known that the TAR region of HIV RNA is required for the binding of the Tat protein and its associated cellular co-factors. Binding of Tat to TAR is essential for viral replication, and a small molecule that is able to bind TAR RNA with high affinity and act as an effective competitor inhibitor will consequently inhibit HIV growth (Hamy et al., 1997). Inhibitors of this class have great potential for use in combination therapy since they inhibit both rapidly growing virus populations as well as attacking the pool of integrated proviruses that serve as the source of drug-resistant mutants.

In a representative method of the invention, a screen for compounds that inhibit HIV replication is described. In this method, fluorescently-labelled compounds (eg. peptides) that are capable of binding to fluorescently labelled RNA targets corresponding to the protein binding sites for Tat in the TAR, or the high affinity site for Rev in the RRE are used as reporters. Where a mixture containing the target RNA, the reporter, and a test compound shows altered fluorescence compared to a mixture containing the target RNA and the reporter molecules alone, an increase in fluorescence or a decrease in fluorescence resonance energy transfer is indicative of the reporter being prevented from binding to the RNA because of competition by the test compound.

An additional example of the application of the method for screening described below is the development of reporter-target RNA pairs suitable for the identification of compounds that bind to the RRE region of HIV RNA.

Example 1

1. Synthesis of FAM-labelled TAR RNA duplexes:
    5'-AGCCAGAUUUGAGCAGC-3' (SEQ ID No. 1)
    5'-FAM-GCUGCUCUCUGGCU-3' (SEQ ID No. 2)
    5'-AGCCAGAUUUGAGCAGCG-3' (SEQ ID No. 3)
    5'-FAM-CGCUGCUCUCUGGCU-3' (SEQ ID No. 4)

RNA duplexes mimicking the TAR RNA structure were prepared by annealing pairs of chemically synthesised oligonucleotides (Karn (WO92/02228 and U.S. Pat. No. 5,821, 046) and (Sumner-Smith et al., 1991; Hamy et al., 1993; Pritchard et al., 1994). Duplex-1 RNA was formed by annealing a 14-mer and a 17-mer (FIG. 2). Duplex-2 was formed by annealing a 15-mer and a 18-mer (FIG. 2).

Chain assembly was carried out on 1 μmol scale using an ABI 380B DNA/RNA synthesiser following the manufacturers protocols and essentially as previously described (Schmidt et al., 1996; Gait et al., 1998) using ribonucleoside phosphoramidates (uracil, N4-benzoyl-cytosine, N2-isopropylphenoxyacetyl-guanine and N6-phenoxyacetyl-adenine) obtained from Glen Research (via Cambio). The reporter dye 6-carboxyfluorescein (FAM) is attached to the 5' terminus using standard phosphoramidite chemistry during automated synthesis using 5'-fluorescein phosphoramidite (6-FAM) obtained from Glen Research. Assemblies were deprotected and cleaved from the support using methanolic ammonia at room temperature for 16 hr followed by triethylamine trihyrdofluoride/DMF (3:1) at 55° C. for 1.5 h as previously described (Schmidt et al., 1996; Gait et al., 1998). After dilution with water, the mixture was desalted by gel filtration on Sephadex NAP-10 columns equilibrated with water. Between 50 and 100 A260 units of crude oligoribonucleotide were obtained before purification. Oligoribonucleotides were purified by ion exchange chromatography on Nucleofac PA-100 (Dionex) (Schmidt et al., 1996; Gait et al., 1998).

The TAR RNA duplexes were obtained by mixing equimolar amounts of the two single stranded RNA molecules in 50 mM Tris-HCl pH 7.6, 20 mM KCl, denaturing at 90° C. for 2 minutes and annealing by gradually reducing the temperature to 37° C. over a period of approximately 1 hour and then incubation on ice for 15 minutes.

Unless otherwise indicated, the following experiments were performed using the TAR RNA Duplex 1.

2. Synthesis of fluorescently-labelled TAR RNA analogues:
    5'-Cy3-CCC AGA UCU GAG CCU GGG AGC UCU CUG GG-3'
    5'-FAM-CCC AGA UCU GAG CCU GGG AGC UCU CUG GG-3'
    5'-CCC AGA UCU GAG CCU GGG AGC UCU CUG GG-DABCYL -3'

These oligoribonucleotides (SEQ ID NO: 5) where synthesised using standard phosphoramidite chemistry by Cybersyn Inc. (USA). 5' dye modifications can be achieved either by a final coupling of the dye phosphoramidite, or by incorporation of a 5' amino group and subsequent reaction with the active ester of the dye. 3' modifications are introduced by synthesis of the oligoribonucleotide upon a dye-derivatised solid support or by synthesis on a 3' amino derivatised solid support with subsequent reaction with the active ester of the dye.

3. Synthesis of fluorescently-labelled RRE RNA analogues:
    5'-CGU GUG GGC GCA GCG UCA AUG ACG CUG CGG UAC ACA CG-DABCYL-3'
    5'-Cy3-CGU GUG GGC GCA GCG UCA AUG ACG CUG CGG UAC ACA CG-3'
    5'-FAM-CGU GUG GGC GCA GCG UCA AUG ACG CUG CGG UAC ACA CG-3'

These oligoribonucleotides (SEQ ID NO: 6) were synthesised as described above.

4. Synthesis of fluorescently-labelled ADP-1 peptides (SEQ ID NO: 7):
    TAMRA-Phe-Thr-Thr-Lys-Ala-Leu-Gly-Ile-Ser-Tyr-Gly-Arg-Lys-Lys-Arg-Arg-G ln-Arg-Arg-Arg-Pro-Pro-Gln-Gly-Ser-Gln-Thr-His-Gln-Val-Ser-Leu-Ser-Lys-Gln
    FAM-Phe-Thr-Thr-Lys-Ala-Leu-Gly-Ile-Ser-Tyr-Gly-Arg-Lys-Lys-Arg-Arg-Gln-Arg-Arg-Arg-Pro-Pro-Gln-Gly-Ser-Gln-Thr-His-Gln-Val-Ser-Leu-Ser-Lys-Gln
    DABCYL-Phe-Thr-Thr-Lys-Ala-Leu-Gly-Ile-Ser-Tyr-Gly-Arg-Lys-Lys-Arg-Arg-Gln-Arg-Arg-Arg-Pro-Pro-Gln-Gly-Ser-Gln-Thr-His-Gln-Val-Ser-Leu-Ser-Lys-Gln The synthesis was performed on a NovaSyn 'Crystal' peptide synthesiser using 100 μmol of Fmoc-Gln(Trt)-NovaSyn-KA resin. Side-chain protection was as follows: Arg(Pmc); Gln(Trt); His(Trt); Lys(Boc); Ser(tBu); Thr(tBu); Tyr(tBu).

All residues except Arg, His, Ser and Thr were coupled for 1 hour using a 5-fold excess of Fmoc-OPfp ester in the presence of 1 equivalent of HOBt in DMF. Acylation reactions were monitored using UV absorbance monitoring at 304 nm. Arg, His, Ser and Thr were coupled for 1 hour using a 5-fold excess of Fmoc-OBt ester generated in situ from the protected amino-acid, PyBOP, HOBt and Hünig's base in DMF. Acylation reactions were monitored using UV absorbance monitoring at 348 nm. Deprotection reactions were monitored using UV absorbance monitoring at 300 nm in 20% Piperidine/DMF. 500 mg of peptidyl-resin was cleaved using 91:3:3:3 (v/v/v/w) TFA/EDT/Et3SiH/PhOH for 3 hours.

The crude product was purified by reverse-phase preparative hplc performed on a Vydac 208TP1022 C8 200×20 mm column using gradients formed using Buffer A (0.1% TFA/

H20) and Buffer B (CH3CN containing 10% Buffer A). The column was eluted isocratically with 15% Buffer B for 2 minutes, then with a linear gradient of 15 to 50% over 25 minutes at a flow rate of 10 ml per min. Detection was at 215 nm. Pure fractions were combined and lyophilised.

For the fluorescent derivatives ca. 500 mg of des Ser-ADP1 was treated with a 5-fold excess of 5 and 6 TAMRA succininmidyl ester, or FAM succininmidyl ester, or DABCYL succininmidyl ester in 10% Hünig's base in DMF. The derivatised-peptidyl resin was cleaved using 91:3:3:3 (v/v/v/w) TFA/EDT/Et3SiH/PhOH for 3 hours. The crude product was purified by reverse-phase preparative hplc performed on a Vydac 208TP1022 C8 200×20 mm column. The column was eluted isocratically with 15% Buffer B for 2 minutes, then with a linear gradient of 20–50% over 25 minutes. Detection was at 215 nm, flow rate 10 ml/min. Pure fractions were combined and lyophilised.

The fluorescently—labelled ADP-1 peptides weredissolved in 50 mM Tris-HCl pH 7.6, 20 mM KCl at appropriate concentrations and stored frozen at −20° C.

5. Synthesis of fluorescently-labelled Rev Peptides

TAMRA-Asp-Thr-Arg-Gln-Ala-Arg-Arg-Asn-Arg-Arg-Arg-Arg-Trp-Arg-Glu Arg-Gln-Arg

FAM-Asp-Thr-Arg-Gln-Ala-Arg-Arg-Asn-Arg-Arg-Arg-Trp-Arg-Glu Arg-Gln-Arg

These compounds (SEQ ID NO: 8) were synthesised as described above.

Example 2

Demonstration of Quenching due to FRET Between FAM-labelled TAR RNA and TAMRA-labelled ADP-1

Figure 4:
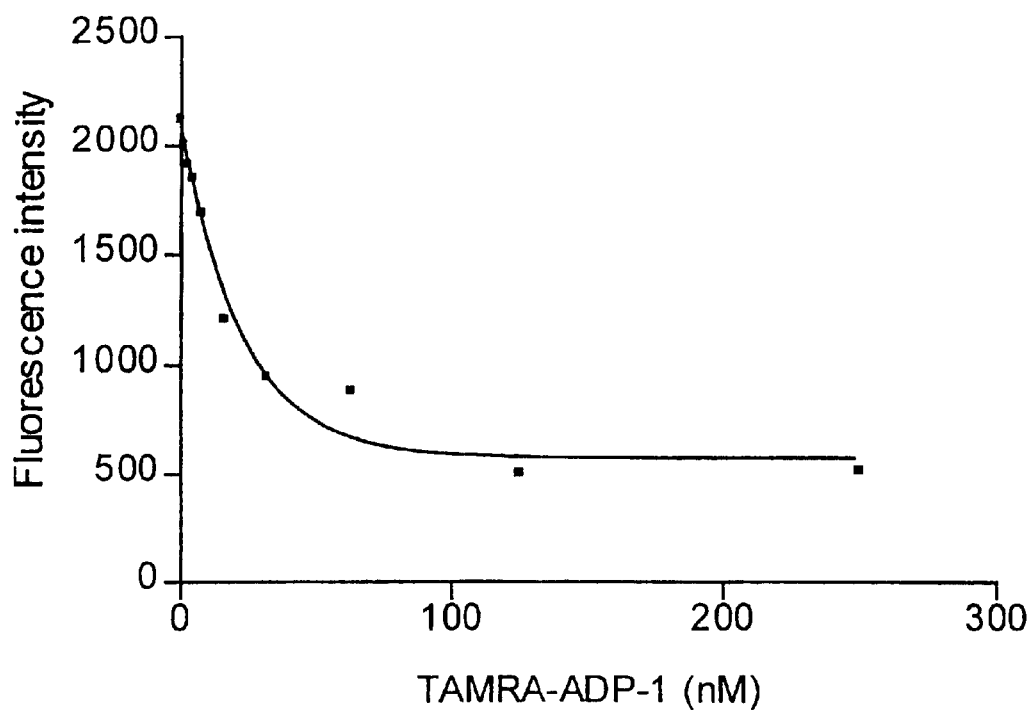
FIG. 4 shows quenching of the 20 nM FAM-labelled TAR RNA Duplex-1 by increasing concentrations of TAMRA-labelled ADP-1.

FIG. 4 shows an experiment demonstrating that it is possible to measure complex formation between a fluorescently labelled target RNA (FAM-labelled TAR RNA) and a fluorescently labelled reporter molecule (TAMRA-labelled ADP-1) by measuring quenching in the complex due to fluorescent resonance energy transfer.

In this experiment, 2 nM FAM-labelled TAR RNA was mixed with increasing concentrations of TAMRA-labelled ADP-1 peptide. The FAM-TAR was diluted from a 100 nM stock solution in TK buffer (50 mM Tris-HCl pH 7.6, 20 mM KCl) to obtain a final assay concentration of 2 nM in 200 μl reaction volume. The TAMRA-labelled ADP-1 peptide was prepared in TK buffer as a 2-fold dilution series at 10 times the assay concentration and diluted 10 fold in to the final assay volume (200 μl). Complex formation was performed for 20 minutes at room temperature and the fluorescence-emission spectra at 535 nm determined in a Wallac Victor™ 1420 following excitation at 485 nm.

The level of fluorescence obtained in the absence of TAMRA-labelled ADP-1 peptide gave a fluorescence intensity of 2100 units. As the ADP-1 concentration is increased there is a progressive loss of fluorescence intensity detected, until at concentrations of ADP-1 greater than 100 nM there is over 80% loss of fluorescence intensity and there is no further quenching detected. This fluorescence profile is consistent with a binding constant ($K_d$) of TAMRA-labelled ADP-1 for FAM-labelled TAR RNA duplex 1 of approximately 25 nM.

Example 3

Unlabelled ADP-1 Peptide does not Quench FAM-labelled TAR RNA Efficiently

Figure 5:
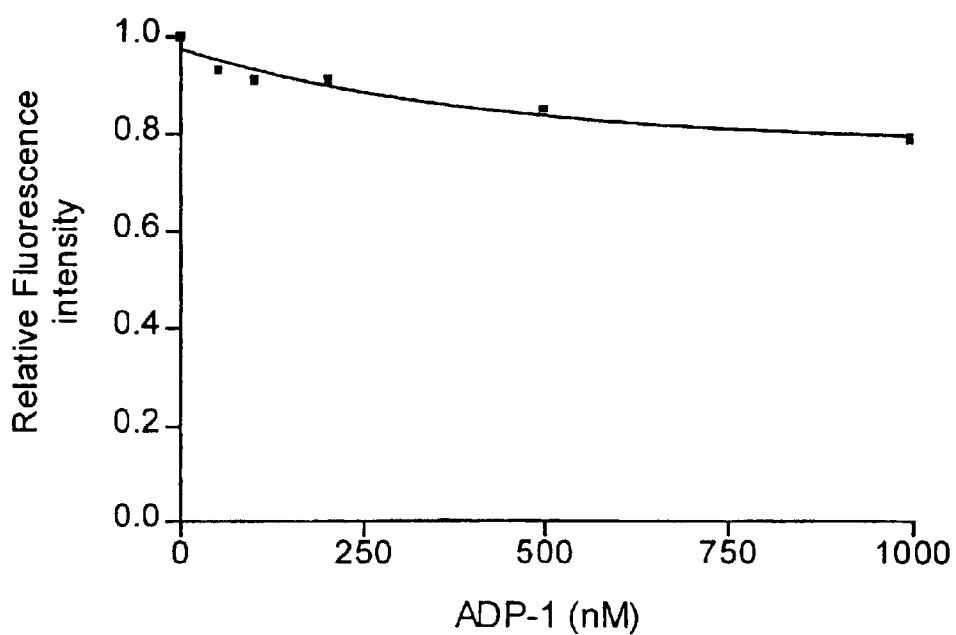
FIG. 5 shows the inability of unlabeled ADP-1 peptide to quench 2 nM FAM-labelled TAR RNA

FIG. 5 illustrates that the quenching observed in FIG. 4 requires the presence of a fluorescent group on the target RNA as well as on the reporter molecules. In this experiment complexes are formed between unlabelled ADP-1 peptide (an unlabelled reporter) and FAM-labelled TAR RNA.

The FAM-TAR was diluted from a 100 nM stock solution in TK buffer (50 mM Tris-HCl pH7.6, 20 mM KCl) to obtain a final assay concentration of 2 nM in 200 μl reaction volume. The unlabelled ADP-1 peptide was prepared in TK buffer as a 2 fold dilution series at 10 times the assay concentration and diluted 10 fold into the final assay volume (200 μl). After complex formation was performed for 20 minutes at room temperature the fluorescence-emission at 535 nm was determined in a Wallac Victor™ 1420 following excitation at 485 nm.

The level of fluorescence obtained in the absence of the unlabelled ADP-1 peptide is normalised to 100% and the levels of fluorescence obtained in the presence of the unlabelled ADP-1 peptide are expressed as a percentage of this value.

As shown in FIG. 5, in contrast to the results obtained using TAMRA-labelled ADP-1, the unmodified peptide is unable to quench the FAM group present on TAR RNA by more than 20%. The failure of the unlabelled reporter to quench the target RNA demonstrates that in the context of this invention, two fluorescent groups are required in order to detect complex formation by fluorescent resonance energy transfer and/or quenching.

The results also illustrate a signficant advantage of this embodiment of the invention, namely, that the use of a flourescent donor and a quenching acceptor dye pair to measure complex formation, results in a strongly enhanced signal in the assay (measured by quenching) compared to the quenching observed when only a single fluorescent dye is placed on either the reporter or the target RNA molecule.

Example 4

Competition Binding Assay Using Unlabelled ADP-1 Peptide Competitor

In the method of this invention, the ability of compounds to bind to RNA is measured by competition binding assays involving a reporter/target RNA pair and the compound to be tested. An important illustration of the method is to demonstrate that unlabelled reporter molecules can act as competitive inhibitors of the binding of the labelled reporter molecules.

Figure 6:
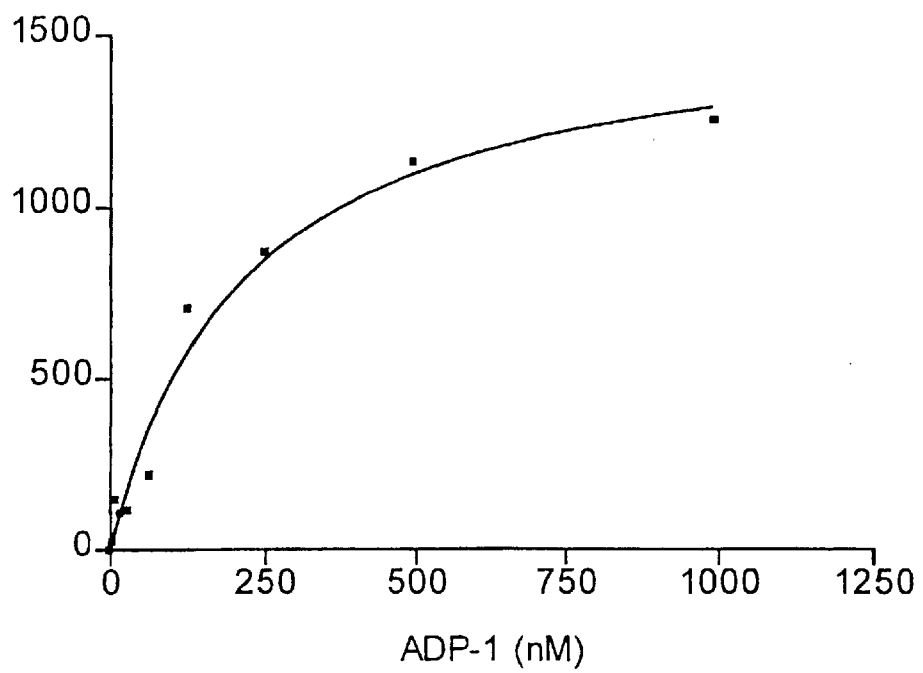
FIG. 6 shows an assay using unlabeled ADP-1 as competitor and 2 nM FAM-labelled TAR RNA Duplex-1, 18 nM unlabeled TAR RNA Duplex-1 and 20 nM TAMRA-labelled ADP-1 peptide.

A control experiment of this type which demonstrates the use of unlabelled ADP-1 as a competitor is shown in FIG. 6. This experiment was performed with a starting condition in which there is an equimolar ratio of TAMRA-labelled ADP-1 peptide and TAR RNA (both labelled and unlabelled). A pre-mix is prepared on ice containing 2 nM FAM-labelled TAR RNA, 18 nM unlabelled TAR RNA and 20 nM TAMRA-labelled ADP-1 peptide diluted in TK buffer to provide the final concentrations (as detailed above) in each 200 μl reaction volume. The ADP-1 peptide was prepared as a 2 fold dilution series in TK buffer at 10 times the assay concentration and diluted 10 fold into the final assay volume. The competition assays were equilibrated for 15 minutes at room temperature and the fluorescence-emission spectra at 535 nm determined in a Wallac Victor™ 1420 following excitation at 485 nm.

For the analysis of this data, the level of fluorescence obtained in the presence of 2 nM FAM-labelled TAR RNA and 100 nM TAMRA-labelled ADP-1 peptide was treated as zero and the levels of fluorescence obtained in the presence of the unlabelled competitor ADP-1 peptide were calculated by subtracting the zero value from the experimental measurement of fluorescent intensity. As shown in FIG. 6, there is a steady rise in fluorescence intensity above the starting value as competitor is added. Under these conditions, the $K_i$ for the unlabelled ADP-1 competitor was measured as 100 nM.

Example 5

Competition Binding Assay Using Unlabelled TAR RNA Competitor

In addition to using unlabelled reporter molecules as competitors it is possible to use unlabelled target RNA molecules as competitors. In the experiment shown in FIG. 7, competition assays were performed essentially as described above.

The binding reactions (200 µl) contained 2 nM FAM-labelled TAR RNA, 50 nM TAMRA-labelled ADP-1 peptide and increasing concentrations of unlabelled TAR RNA. The TAR RNA was prepared as a 2-fold dilution series in TK buffer at 10 times the assay concentration and diluted 10-fold in to the final assay volume. The level of fluorescence obtained in the presence of 2 nM FAM-labelled TAR RNA and 50 nM TAMRA-labelled ADP-1 peptide was treated as zero and the levels of fluorescence obtained in the presence of the unlabelled competitor TAR RNA were calculated by subtracting the zero value from the experimental measurements of fluorescent intensity.

Figure 7:
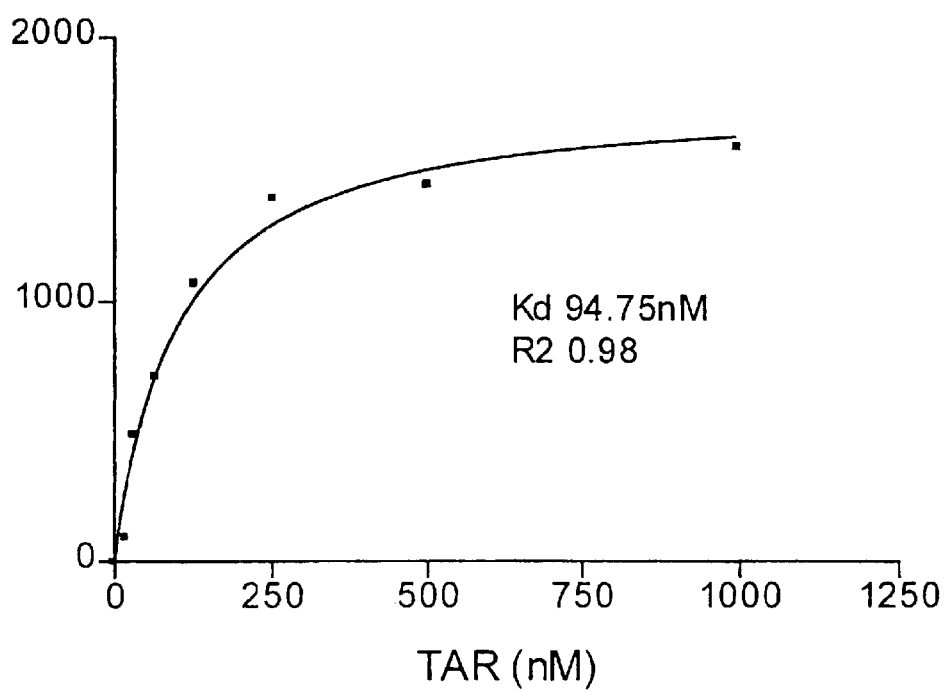
FIG. 7 shows a competition binding assay using unlabeled TAR RNA Duplex-1 as a competitor and 2 nM FAM-labelled TAR RNA Duplex-1 and 50 nM TAMRA-labelled ADP-1 peptide.

As shown in FIG. 7, there is a progressive increase in fluorescence intensity as the unlabelled TAR RNA is added to the reaction mixture. This demonstrates that the unlabelled TAR RNA can act as an effective competitive inhibitor of the binding of TAMRA-labelled ADP-1 to FAM-labelled TAR RNA. Under these conditions, the $K_i$ for the unlabelled TAR RNA competitor was measured as 100 nM.

Example 6

Competition Assay Measuring the Binding of Cyclic Peptides to TAR RNA

Figure 8:
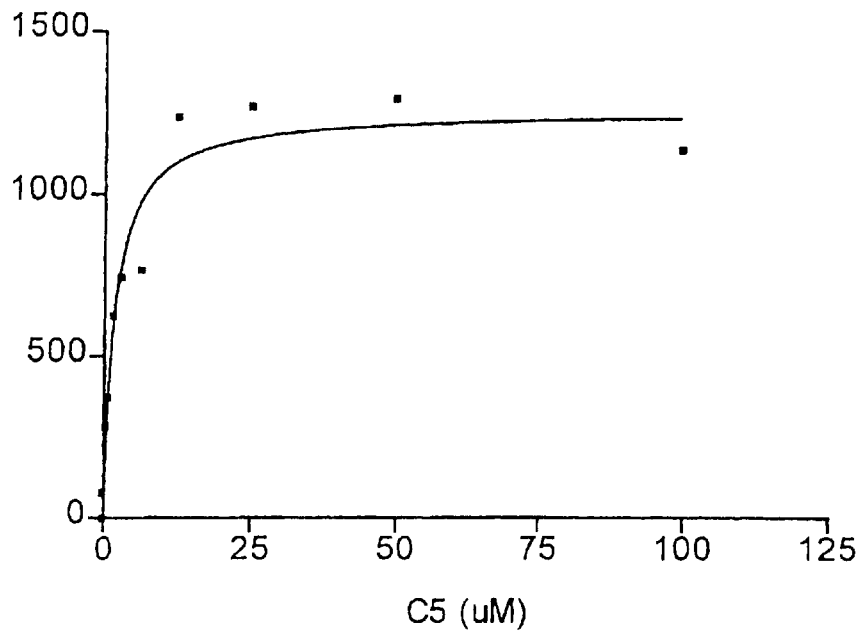
FIG. 8 shows a competition assay measuring the binding of C5 to TAR RNA.
Figure 9:
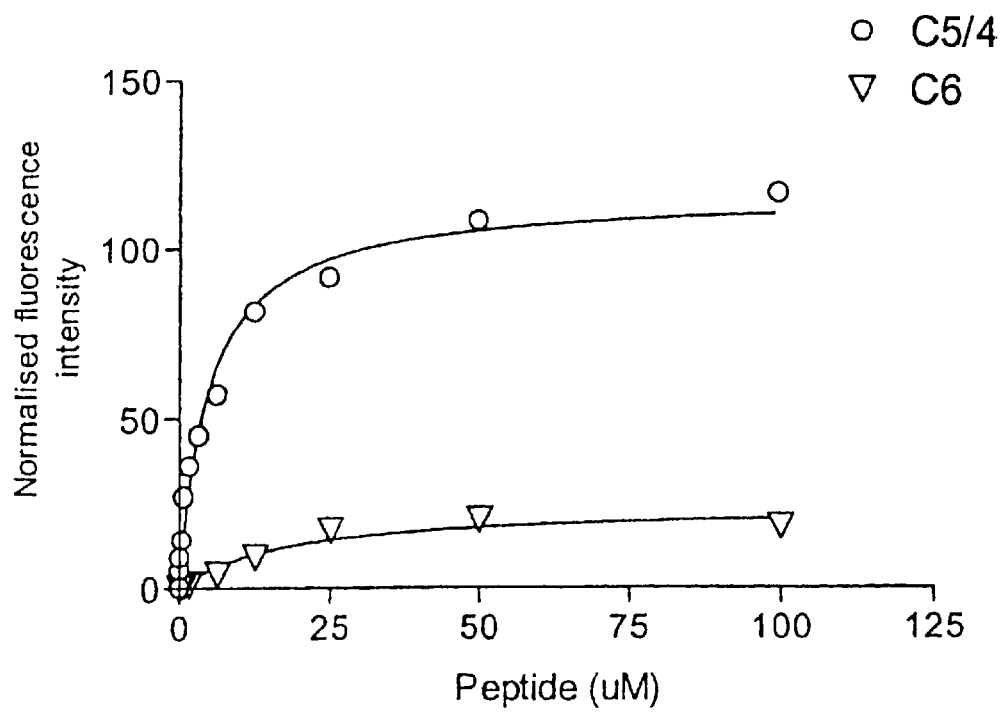
FIG. 9 shows a competition assay measuring the binding of C5/4 and C6 to TAR RNA.

The use of this competition binding assay to evaluate the relative binding of low molecular weight compounds to TAR RNA is further illustrated by the experiments shown in FIGS. 8 and 9. In these examples, the compounds evaluated are cyclic penta- and hexa-peptides. These peptides form a series of compounds in which the backbone geometry of the pentapeptide scaffold is altered by the introduction of a single D-amino acid.

FIG. 8 shows the results of a competition binding assay performed in the presence of 2 nM FAM-labelled TAR RNA, 18 nM unlabelled TAR RNA, 20 nM. TAMRA-labelled ADP-1 peptide and increasing concentrations of C5 cyclic peptide (SEQ ID 9). A pre-mix is prepared on ice containing the FAM-labelled TAR RNA, unlabelled TAR RNA and the TAMRA-labelled ADP-1 peptide diluted in TK buffer to provide the final concentrations (as detailed above) in each 200 µl reaction volume. The C5 cyclic peptide was prepared as a 2 fold dilution series in TK buffer at 10 times the assay concentration and diluted 10 fold in to the final assay volume. FIG. 9 shows a similar competition bindingassay measuring the binding of C5/4 and C6 to TAR RNA.

Addition of increasing concentrations of cyclic peptides that bind TAR RNA prevents the binding of the TAMRA-labelled ADP-1 to the FAM-labelled TAR RNA and consequently results in a progressive increase in fluorescence. The relative efficiency of the various cyclic peptides can be measured by comparing $k_i$ values obtained from this type of assay. The most efficient competitors in a series of pentapeptides in which amino acids at each position of the sequence were substituted by D-amino acids were C5 and C5/4 (FIG. 8 and FIG. 9).

In contrast to the pentapeptides, the cyclic hexapeptides C6 does not show any significant binding to TAR RNA (FIG. 9).

The results obtained from an evaluation of the complete series of cyclic pentapeptides using another version of the competition assay (DABCYL-labelled TAR RNA and FAM-labelled ADP-1 peptide) are summarized in Table 3.

Example 7

Figure 10:
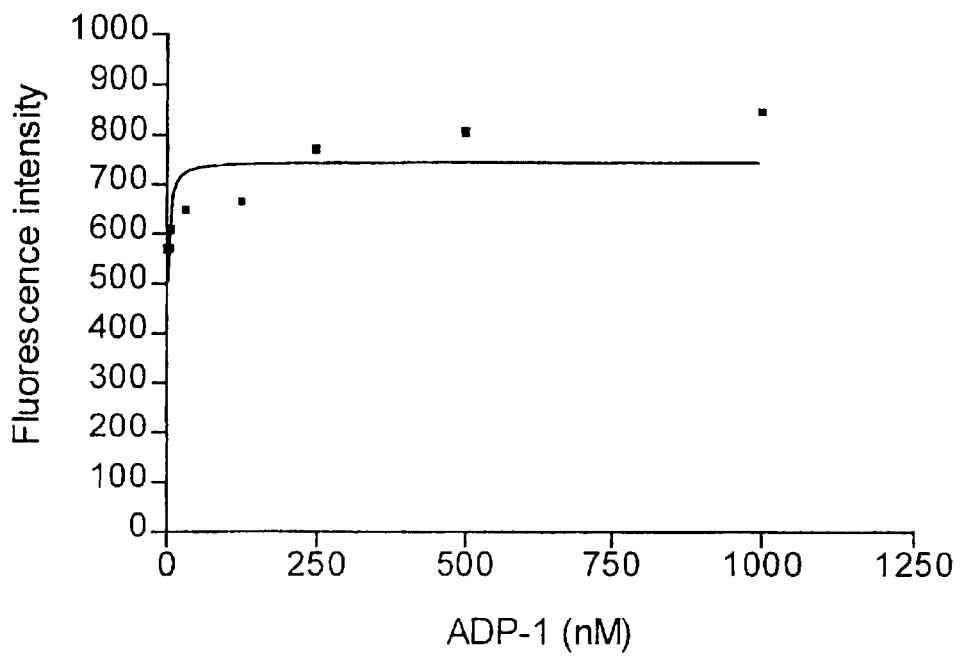
FIG. 10 shows a competition assay using 2 nM FAM-labelled TAR RNA Duplex-2, 18 nM unlabeled TAR RNA Duplex-2, 20 nM TAMRA-labelled ADP-1 peptide and unlabeled ADP-1 peptide as a competitor.

FAM-labelled TAR RNA Duplex-2 Shows Reduced FRET with TAMRA-labelled ADP-1 Peptide In order to obtain efficient fluorescent resonance energy transfer and/or quenching it is important that the fluorescent groups are placed on the reporter and the target RNA to permit close contact between the donor and acceptors after complex formation. An example of a sub-optimal configuration of fluorescent groups is shown in FIG. 10. In this experiment the FAM group on the TAR RNA target (Duplex 2) has been displaced by the addition of a base pair. This alteration to the target RNA structure has the effect of increasing the distance of the FAM group from the binding site on the TAR RNA duplex by 2 Å more than the equivalent group on the TAR RNA Duplex 1 target. In addition, insertion of the base pair rotates the FAM group by 18° compared to the equivalent group in the Duplex-1 TAR RNA target. As a result of these changes in the position of the FAM group, the Duplex-2 TAR RNA shows significantly lower quenching due to FRET when bound to TAMRA-labelled ADP-1 peptide than does Duplex 1 TAR RNA.

The experiment in FIG. 10 shows a competition binding assay in the presence of 2 nM FAM-labelled TAR RNA Duplex-2, 18 nM unlabelled TAR RNA Duplex-2, 20 nM TAMRA-labelled ADP-1 peptide and increasing concentrations of ADP-1 peptide. Because Duplex-2 has a sub-optimal spacing of the FAM-label on TAR RNA it gives rise to a poor signal in the assay compared to Duplex-1, with a less than 50% rise in fluorescence in the presence of saturating concentrations of ADP-1 competitor.

Example 8

Spectral Analysis of FRET Between Cy3-TAR RNA and FAM-labelled ADP-1

In the preceding experiments quenching of the fluorescence of a donor due to fluorescence resonance energy transfer was used as a measurement of complex formation between the reporter molecule and the target RNA. In addition to quenching of the donor signal, FRET produces a transfer of energy to the acceptor dye which results in a fluorescent emission. In order to provide a direct and formal demonstration of FRET, complete spectral measurements were obtained in order to simultaneously measure donor quenching and acceptor enhancement after the formation of complexes between the ADP-1 reporter and the TAR RNA target molecules. For these experiments a new combination of donor acceptor pairs was used: the donor group, in this example FAM, was placed on the ADP-1 reporter and the acceptor group, in this example Cy-3, was placed on the TAR RNA target.

Fluorescence measurements were carried out on a Perkin-Elmer LS50-B luminometer. The emission spectra were corrected for lamp fluctuations and instrumental variations. Polarisation artifacts were circumvented by setting the excitation and emission polarisers at 54.7° (the 'magic angle').

Figure 11:
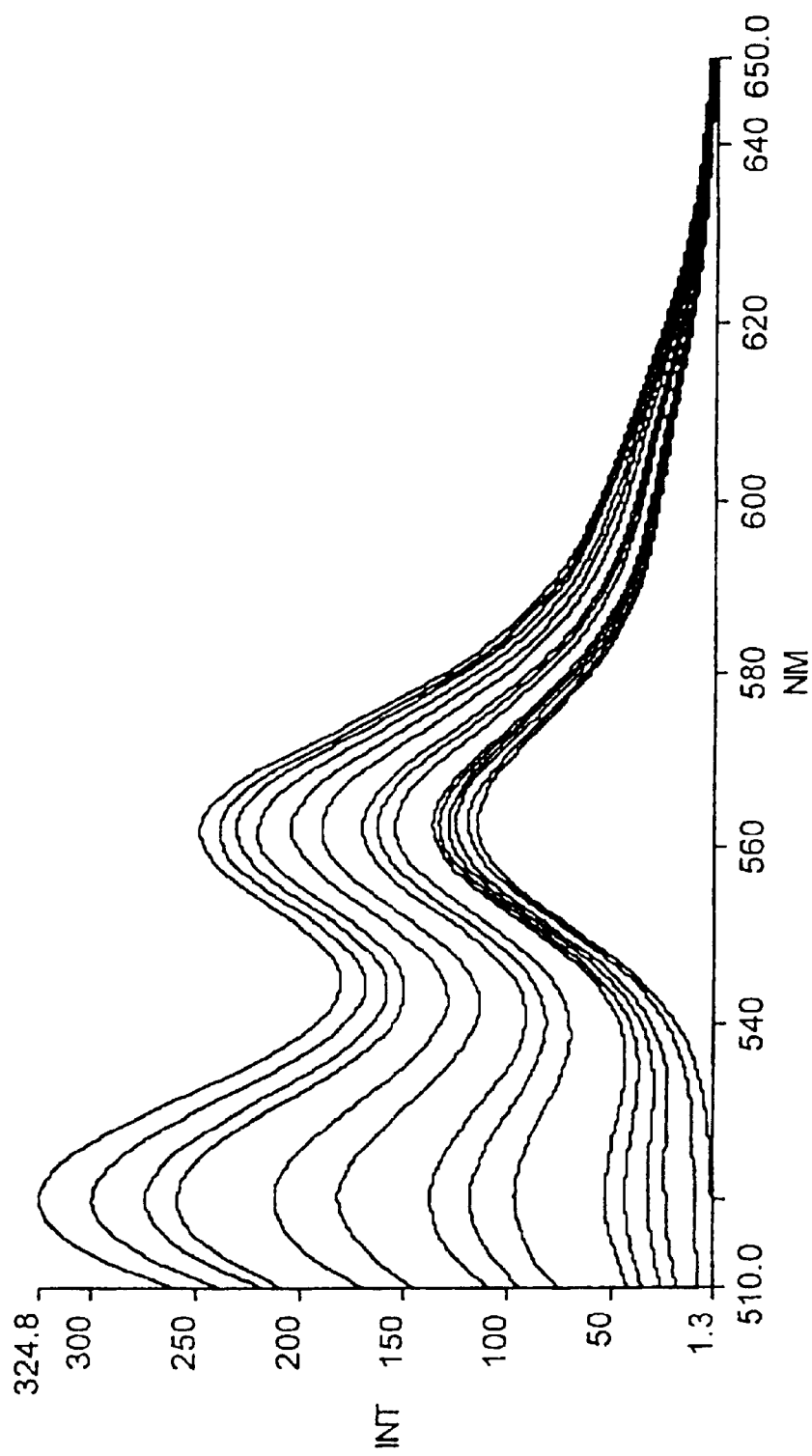
FIG. 11 shows a spectral analysis of the activation of the fluorescence of 20 nM Cy3-TAR RNA by FRET when it is complexed with increasing concentrations of FAM-labelled ADP-1

For the experiment shown in FIG. 11, measurements were made in a 2 ml cuvette and increasing amounts of FAM-labelled ADP-1 were added to a solution of 20 nM Cy-3 TAR RNA in the presence of 50 mM Tris-HCl pH 7.5, 20 mM KCl and 1% DMSO. For each titration point emission spectra were acquired utilising a fixed wavelength of 480 nm with the excitation slits set to 5 nm and the emission slits set to 10 nm. Emission spectra were aquired over the range of 510 nm to 650 nm (FIG. 11). This range encompasses the emission spectrum of the donor (FAM) (510 nm to 530 nm) and also the emission spectrum of the acceptor (Cy-3) (540 nm to 580 nm). Analysis of the complete spectra permits any spectral shifts to either the donor or the acceptor to be detected.

A second emission spectrum was acquired at a fixed excitation wavelength of 547 nm over the range of 558 nm to 650 nm. In this range the acceptor (Cy-3) is uniquely excited. In addition a third emission spectrum of the donor (FAM) alone was acquired at a fixed excitation wavelength of 480 nm over the range of 510 nm to 650 nm this provides a standard donor spectrum.

In the emission spectrum, the donor (FAM) has some spectral overlap with the acceptor (Cy-3) this contribution has to be removed in order to determine whether there has been fluorescence resonance energy transfer. For each dataset a buffer spectrum was subtracted. The emission spectrum of the donor alone was then fitted to that of the donor and acceptor spectra. This provides the contribution of the donor in the acceptor region of the spectrum which can be subtracted. The spectrum of the acceptor alone is also subtracted to account for the direct excitation of the acceptor, this gives the extracted emission signal due to energy transfer. The extracted emission signal due to energy transfer is then divided by the emission signal for the acceptor alone to give the ratio A' (Clegg 1992) and is linearly dependant on the efficiency of energy transfer E.

Figure 12:
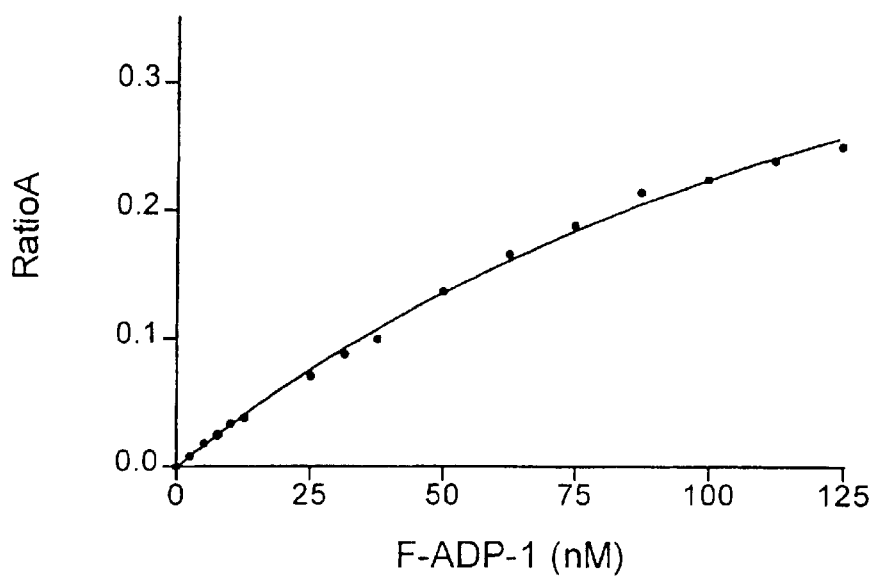
FIG. 12 shows a binding curve based on the data shown in FIG. 9.

As shown in FIG. 12, which provides an analysis of the experimental data shown in FIG. 11, increasing concentrations of FAM ADP-1 in the presence of Cy-3 TAR RNA results in an increase in A' value. This was demonstrates that fluorescence resonance energy transfer is able to take place between the two dyes upon the peptide binding to the TAR RNA.

Example 9

Disruption of Cy-3 TAR-FAM-ADP-1 Complex by KCl

Figure 13A:
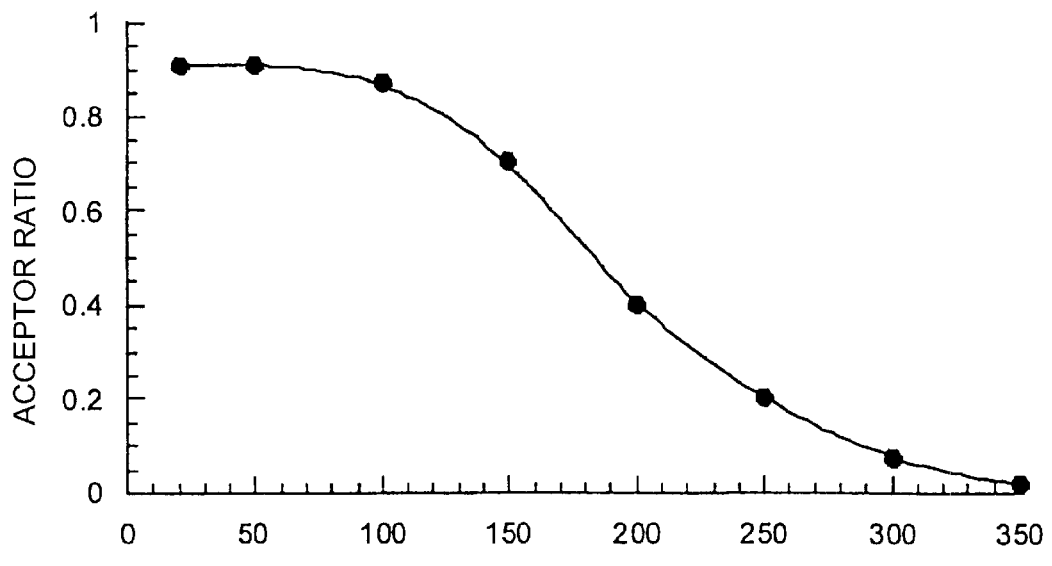
FIG. 13 shows the effect of disruption of the complex formed between 50 mM FAM-labelled ADP-1 and 20 nM Cy3-TAR RNA by increasing concentrations of KCl (mM) on the acceptor and donor signals.
Figure 13B:
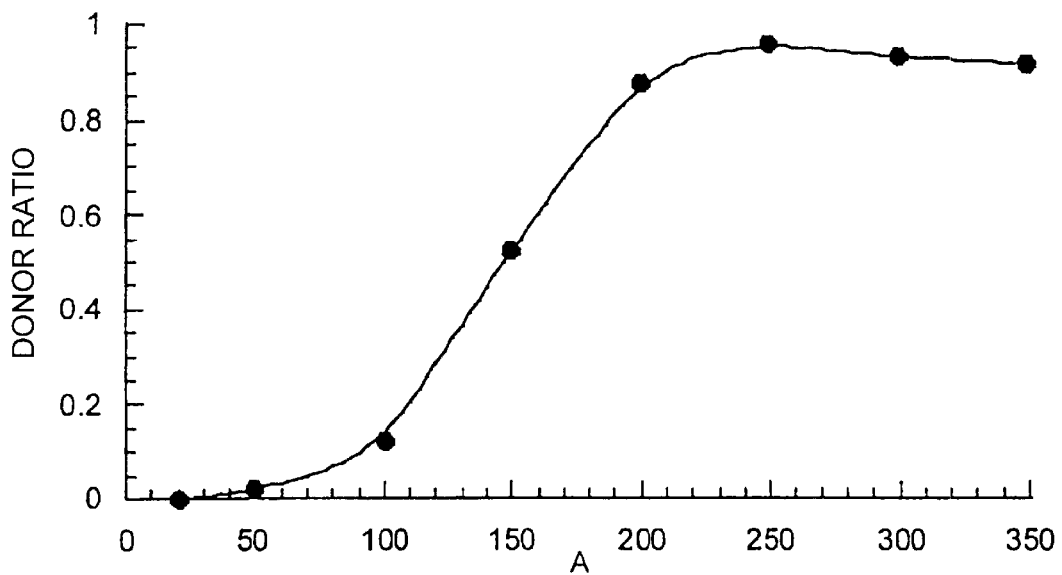

As described above, formation of a complex between FAM-labelled ADP-1 reporter and Cy-3 labelled TAR RNA results in quenching of the FAM group present on the reporter and enhancement of the fluorescence of the Cy3 group on the labelled TAR RNA target. It follows that disruption of peptide RNA binding should bring about a-decrease in energy transfer which will be observed as an decrease in acceptor fluorescence intensity and a corresponding increase in donor fluorescence intensity. In the experiment shown in FIG. 13, the chaotropic reagent KCl, is used to progressively disrupt the complex. In this figure, the ratio A' is presented as a function of KCl concentration in the top panel, and the donor ratio as a proportion of the total donor intensity in the absence of acceptor is also shown in the bottom panel.

Example 10

Spectral Analysis of FRET Between DABCYL-TAR RNA and FAM-labelled ADP-1

As illustrated above, complex formation between labelled reporters and target RNA molecules positions donor and acceptor groups so that fluorescence resonance energy transfer can take place. This results in an increase inacceptor emission intensity and a corresponding decrease of the donor emission intensity. The donor emission intensity will also decrease in the presence of a non-fluorescent acceptor such as the DABCYL group. The use of single fluorescent group and a quenching group simplifies the detection of the fluorescent signal since there is no need to correct for overlapping signals coming from the acceptor group.

This configuration of the assay is useful when screening unknown compounds for RNA binding activity, since the use of a single fluorescent group in the assay simplifies the analysis of possible quenching effects by the compound under evaluation. In addition, the assay may be performed using instruments, such as the Wallac Victor, that detect signals at fixed wavelengths.

Figure 14:
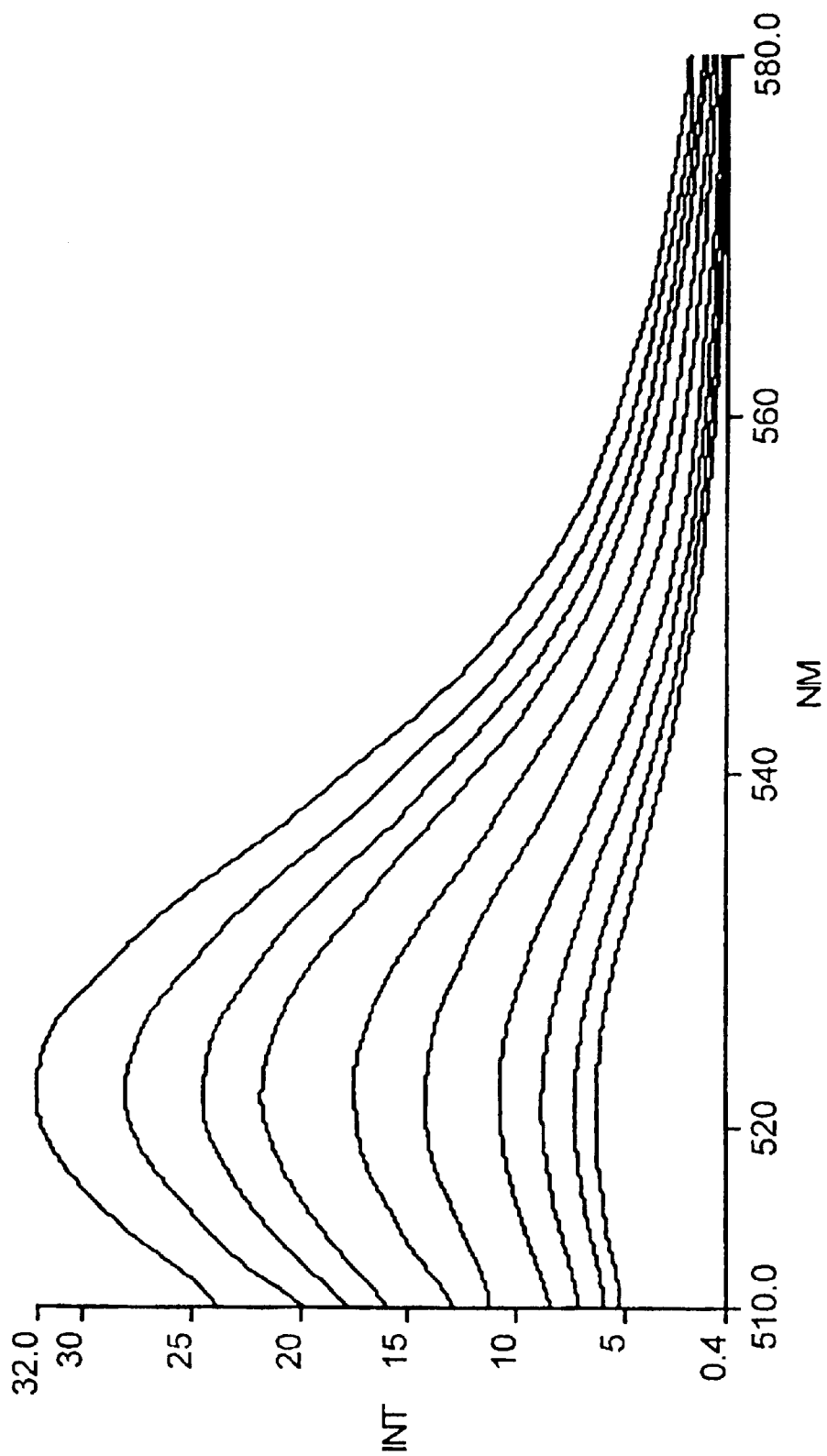
FIG. 14 shows a spectral analysis of the quenching of 10 nM FAM-ADP by increasing concentrations of DABCYL-TAR RNA.

An example of a quenching assay is illustrated in FIG. 14, which measures the binding of FAM-labelled ADP-1 reporter to DABCYL-labelled TAR RNA. In this example, the FAM group acts as a fluorescent donor, while the DABCYL group acts as a non-fluorescent acceptor.

In the experiment shown in FIG. 14, emission spectra were acquired utilising a fixed wavelength of 490 nm with the excitation slits set to 5 nm and the emission slits set to 10 nm for each titration point. Measurements were made in a 2 ml cuvette, and increasing amounts of DABCYL-TAR RNA were added to a solution of 10 nM fluoresein-ADP-1 in the presence of 50 mM Tris-HCl pH 7.5, 20 mM KCl, 1% DMSO, 0.01% Triton X-100 and 5 µg/ml BSA.

Figure 15A:
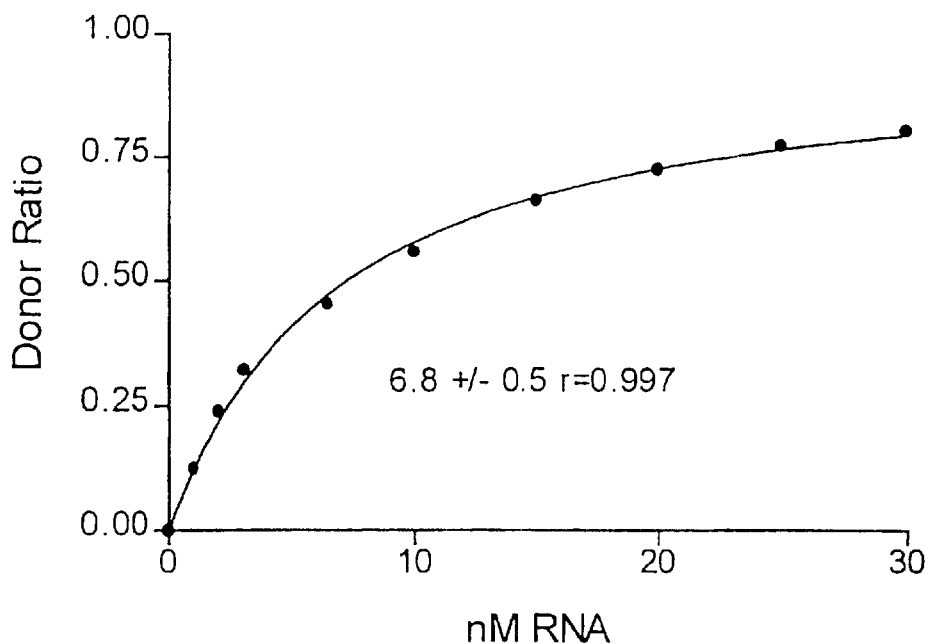
FIG. 15A shows a binding curve based on the data shown in FIG. 14.
Figure 15B:
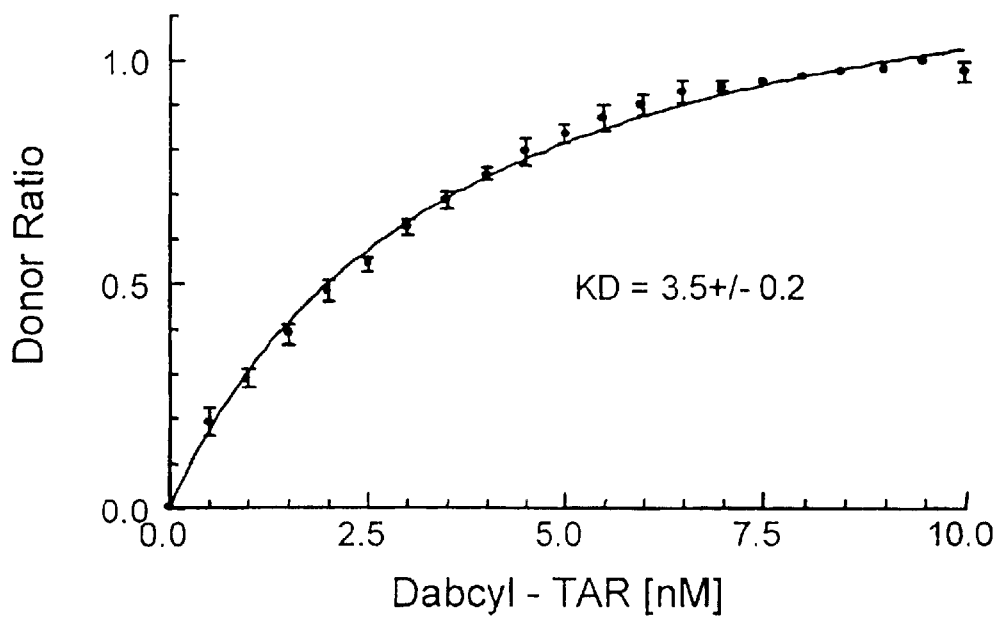
FIG. 15B shows a similar experiment over a narrower range.

Emission spectra were acquired over the range of 510 nm to 580 nm. This range encompasses the emission spectrum of the donor (fluorescein). The donor ratio is simply the difference in donor intensity on addition of DABCYL TAR as a proportion of the total donor intensity in the absence of acceptor. A progressive reduction in donor intensity is observed, due to fluorescence resonance energy transfer taking place between the two dyes upon the peptide binding to the TAR RNA. This is shown in FIG. 15A, which presents a plot of the donor ratio for the experiment shown in FIG. 14. FIG. 15B shows the results of a quantitative analysis of the ADP-1/TAR interaction, performed in the same way as described above but over a narrower range of TAR concentrations. The error bars show the standard deviation over five replicate experiments.

Example 11

Competition Assays Using DABCYL-TAR RNA and FAM-labelled ADP-1

Figure 16:
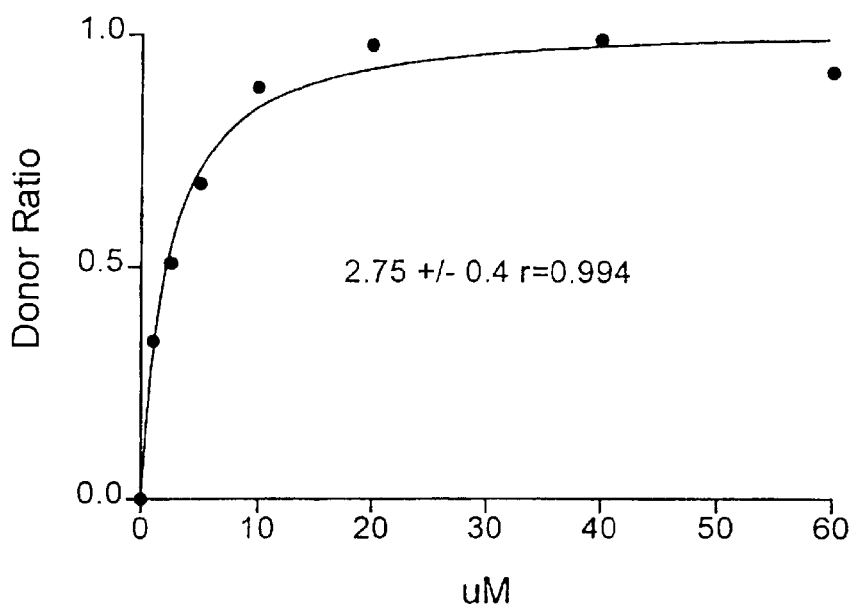
FIG. 16 shows a competition assay using 10 nM DABCYL-TAR RNA and 10 nM TAMRA-labelled-ADP-1, and increasing concentrations of the RNA-binding compound RBT171.

Disruption of peptide RNA binding by a compound that binds the target RNA should bring about a decrease in energy transfer which will be observed as an increase in donor fluorescence intensity. For the DABCYL-TAR RNA and FAM- ADP-1 pair described above, a competition binding assay was implemented on the LS50-B luminometer in 96-well plates utilising the fluorescent plate reading accessory. Measurements were made in a 200 ml volume, and increasing amounts of the RNA binding compound RBT171 were added to a solution of 10 nM DABCYL-TAR RNA in the presence of 50 mM Tris-HCl pH 7.5, 20 mM KCl, 1% DMSO 0.01% Triton X-100 and 5 µg/ml BSA. Following addition of the compound, 10 nM fluorescein-ADP-1 was added. Emission spectra were aquired in the range of 517–532 nm utilising a fixed wavelength of 490 nm with the excitation slits set to 5 nm and the emission slits set to 10 nm. FIG. 16 shows a plot of the donor ratio obtained in this experiment. The use of 96 wells plates is advantageous for high throughput screening of compounds since addition of the assay components to the plates can be performed by readily available liquid handling robots.

The difference in donor intensity on addition of compound as a proportion of total available donor intensity is indicative of compound binding and the data may used to calculate a $K_i$ value of the compound. For the data shown in FIG. 16, the Ki of RBT171 is 2.75±0.4 M.

Figure 17:
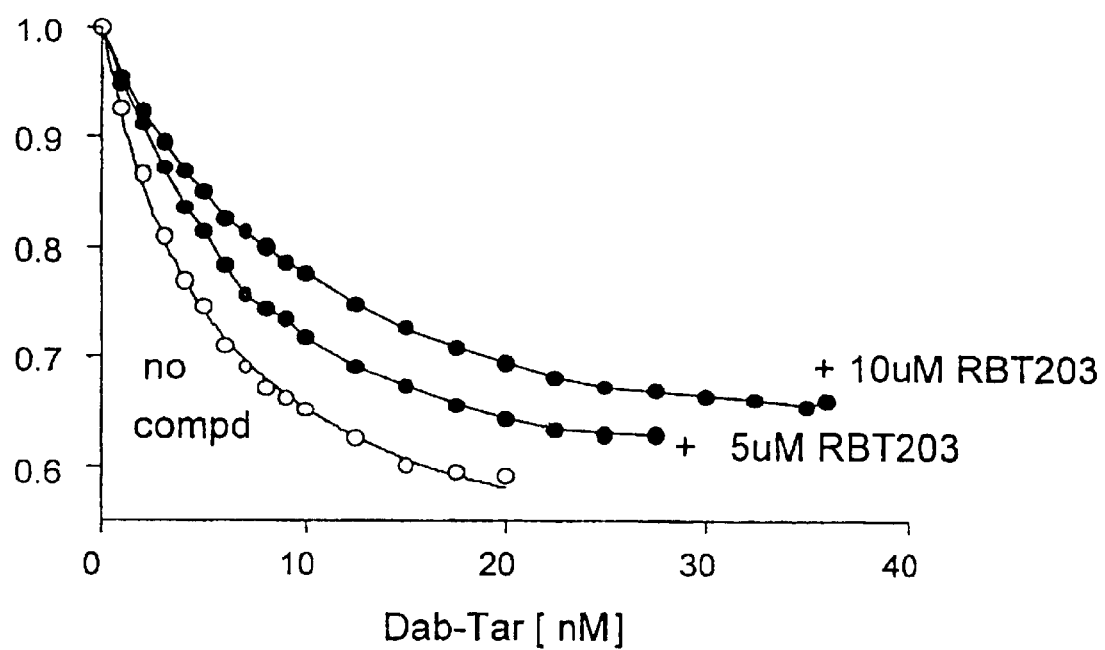
FIG. 17 shows a titration of DABCYL-TAR RNA in the presence and absence of the RNA-binding compound RBT171

Another useful assay configuration for measuring the competitive inhibition of DABCYL-TAR RNA binding to fluorescein-ADP-1 by an RNA-binding compound is to perform a titration of the DABCYL-TAR RNA in the presence of a fixed concentration of the compound to be analysed. An example of this type of assay is shown in FIG. 17. In this experiment, measurements were made in a 2 ml cuvette, and increasing amounts of DABCYL-TAR RNA (corresponding to the amounts shown in FIG. 17) were added to a solution of 10 nM Fluoresein-ADP-1 in the presence of 50 mM Tris-HCl pH7.5, 80 mM KCl, 1% DMSO 0.01% Triton X-100, 5 µg/ml BSA, 20 nM competitor RNA in the presence of 0, 5 or 10 µM of the compound RBT203. For each titration point emission spectra were acquired using a fixed wavelength of 490 nm with the excitation slits set to 5 nm and the emission slits set to 10 nm. Emission spectra were acquired over the range 51014 580 nm.

Fluorescein fluorescence was plotted as a fraction of the original signal in the absence of DABCYL RNA ($I/I_0$). Comparison with the titration in the absence of compound shows an increase in fluorescence in the presence of compound, corresponding to a reduction in energy transfer, clearly demonstrating inhibition of complex formation by the compound RBT203.

Measurements of this kind, in which the acceptor is added in the presence of a constant amount of donor and compound, show clear advantages over methods where the compound concentration is varied.

i) The effects of compound quenching on donor fluorescence are constant throughout the experiment, and are taken into account in the measurement (the $I_0$ measurement is made in the presence of compound).

ii) Differences in compound solubility are circumvented (compound concentration is constant throughout the experiment).

iii) The methodology can be readily transferred to a fluorescent microplate reader.

iv) In a mircoplate reader $I_0$ can be determined by a measurement prior to addition of the acceptor.

Example 12

Competition Assays Using DABCYL-TAR RNA and TAMRA-labelled ADP-1

Because of the broad adsorption spectrum of DABCYL it is possible to use this quenching group in conjunction with fluorescent dyes other than fluorescein. This is advantageous when working with inhibitors that have adsorption spectra that overlap with fluorescein.

Figure 18:
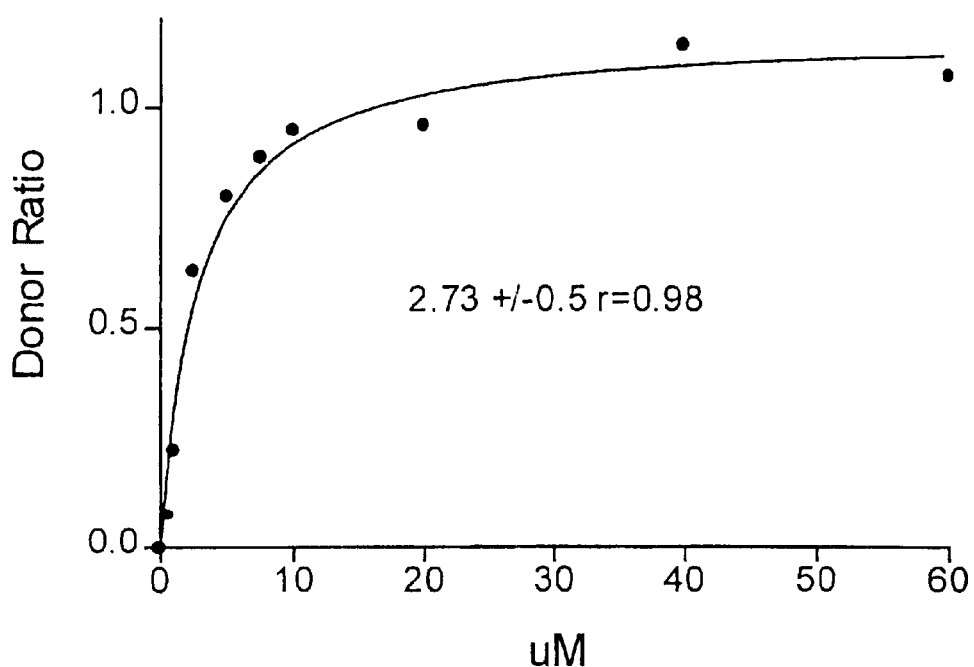
FIG. 18 shows a competition assay using 10 nM DABCYL-TAR RNA and 10 nM FAM-labelled ADP-1 and increasing concentrations of the RNA-binding compound RBT171

An example of an experiment using the DABCYL-TAR RNA and TAMRA-labelled ADP-1 pair is shown in FIG. 18. The experiment was performed on the LS50-B luminometer utilising the fluorescent plate reading accessory. Measurements were made in a 200 ml volume. Increasing amounts of the RNA binding compound RBT171 were added to a solution of 10 nM DABCYL-TAR RNA in the presence of 50 mM Tris.HCl pH7.5, 20 mM KCl, 1% DMSO 0.01% Triton X-100 and 5 µg/ml BSA. Following addition of the compound, 10 nM TAMRA-ADP-1 was added. Emission spectra were aquired in the range 578–584 nm utilising a fixed wavelength of 554 nm, with the excitation slits set to 5 nm and the emission slits set to 10 nm. The donor ratio presented is the difference in donor intensity on addition of compound as a proportion of total available donor intensity. For the data shown in FIG. 18, the $K_i$ of RBT171 is 2.73±0.5 µM, in excellent agreement with the results shown in FIG. 16 using the alternative dye pairs.

Example 13

Assays Using FAM-TAR RNA and DABCYL-labelled ADP-1

It is also possible to place a fluorescent group on the RNA target and a quenching group on the reporter molecule. To confirm that DABCYL-ADP-1 could bind FAM-TAR and that the complex would result in the proximal location of the two fluorophores such that the DABCYL could significantly quench the fluorescein fluorophore, 20 nM FAM-TAR was incubated with increasing concentrations of DABCYL-ADP-1. The DABCYL-ADP-1 was pre-treated in the presence of 1% TFA at room temperature for 5 minutes prior to dilution into binding buffer (0.01% Triton X-100, 5 µg/ml BSA, 1% DMSO, 50 mM Tris-HCl pH 7.6, 20 mM KCl) and incubated on ice prior to complex formation.

Figure 19:
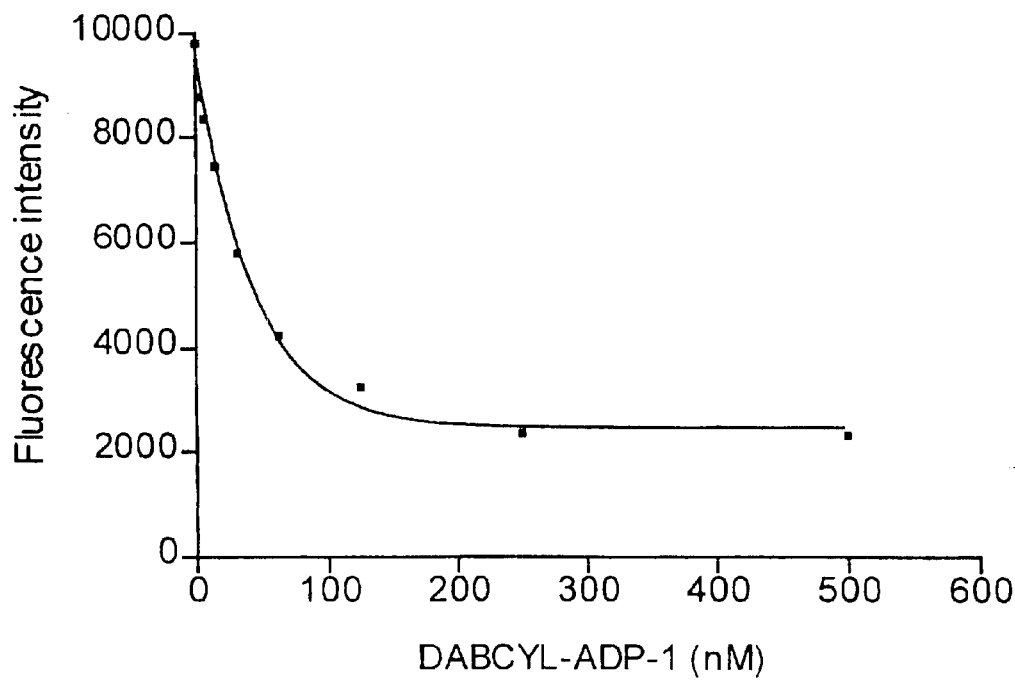
FIG. 19 shows a binding curve based on the quenching of 20 nM FAM-TAR RNA by increasing concentrations of DABCYL-labelled ADP-1 peptide.

Reactions were equilibrated at room temperature for 15 minutes prior to analysis in the Wallac Victor2 plate reader. The reactions were excited at 485 nm and fluorescence emission recorded at 535 nm. The fluorescence emission signal of the 20 nM FAM-TAR is progressively quenched after addition of increasing amounts of DABCYL-ADP-1 peptide. The experimental data shown in FIG. 19 was analysed in GraphPad PRISMTM using a non linear regression fit for single site binding. The results showed that Kd=33 (2.4 nM with an R2 value of 0.99).

Example 14

Competition Binding Assays Using FAM-TAR RNA and DABCYL-labelled ADP-1

Having demonstrated that the DABCYL-ADP-1 could bind FAM-TAR and quench its fluorescence, we next used this reporter:target RNA combination in competition assays.

DABCYL-ADP-1 was pre-treated with 1% TFA as described above and stored on ice until required. The FAM-TAR was pipetted into a reaction mixture containing the RNA binding compound RBT171 (at the desired concentration) in the presence of Triton X-100, BSA, Tris-HCl, KCl and DMSO. Following the addition of DABCYL-ADP-1 the final concentration for each component was 20 nM FAM-TAR, 50 nM DABCYL-ADP-1, 1% DMSO, 0.01% Triton X100, 5 µg/ml BSA, 50 mM Tris-HCl pH 7.6, 20 mM KCl, and various concentration of RBT171 between 0 and 100 µM. Reactions were equilibrated at room temperature for 15 minutes prior to analysis in the Victor plate reader. The reactions were excited at 485 nm and fluorescence emission recorded at 535 nm.

Figure 20:
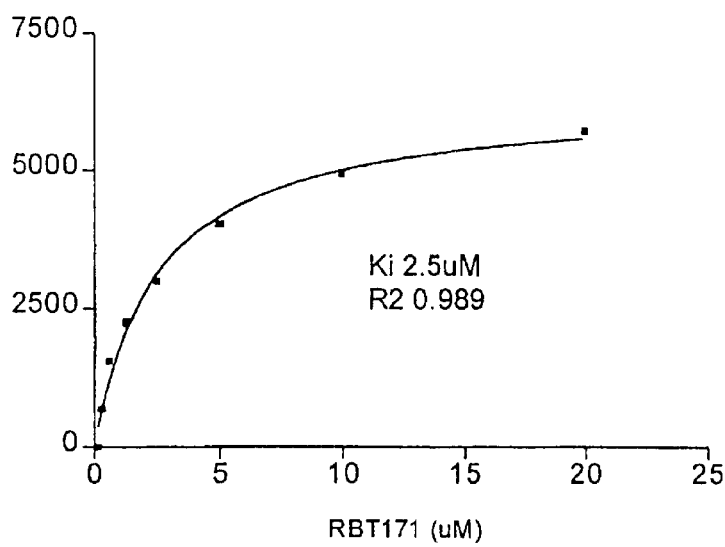
FIG. 20 shows an assay using 20 nM FAM-TAR RNA, 50 nM DABCYL-ADP-1 and increasing concentrations of the RNA-binding compound RBT171.

Mixing increasing concentrations of RBT171 with FAM-TAR RNA resulted in an enhancement of the fluorescein emission. Therefore, for each concentration of RBT171, a correction factor was determined by comparing the signal obtained from 20 nM FAM-TAR in the absence of RBT171 to the signal obtained in the presence of the compound. The signal obtained in the presence of RBT171, FAM-TAR and DABCYL-ADP-1 was then multiplied by the correction factor for the appropriate drug concentration. The fluorescence emission signal of the 20 nM FAM-TAR alone was subtracted from each corrected-signal obtained in the presence of increasing amounts of RBT171 and plotted as a function of RBT171 concentration (FIG. 20) in GraphPad PRISM™. The results showed $K_i=2.5\pm0.3$ μM with an R2 value of 0.989. This is within the error of the previously described determinations using the alternative reporter-RNA combinations.

Example 15

Assays Using DABCYL-RRE RNA and TAMRA-labelled Rev Peptide

To demonstrate that the method is applicable to target RNA/reporter peptide complexes, other than TAR RNA and ADP-1 and that alternate dye pairs can be exploited, complex formation by DABCYL-RRE RNA and TAMRA-Rev peptide was analysed. The complex resulted in the proximal location of the two fluorophores such that the DABCYL significantly quenched the rhodamine fluorophore.

Figure 21:
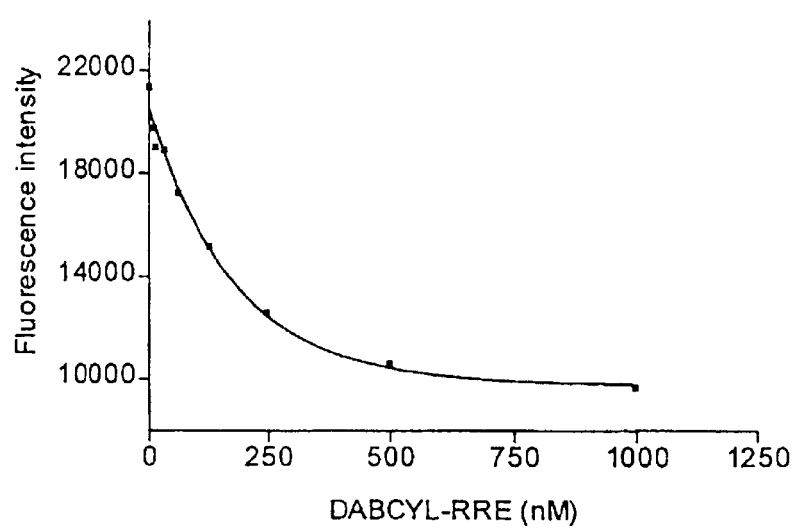
FIG. 21 shows a binding curve based on the quenching of 20 nM TAMRA-labelled Rev peptide and increasing concentrations of DABCYL-RRE RNA.

In the experiment shown in FIG. 21, 20 nM TAMRA-Rev was incubated with increasing concentrations of DABCYL-RRE. The TAMRA-Rev was pre-treated in the presence of 1% TFA at room temperature for 5 minutes prior to dilution in to storage buffer (0.01% Triton X-100, 5 μg/ml BSA, 1% DMSO, 50 mM Tris-HCl pH 8, 50 mM KCl) and incubated on ice prior to complex formation. Reactions were equilibrated at room temperature for 15 minutes prior to analysis in the Wallac Victor2 plate reader. The reactions were excited at 544 nm and fluorescence emission recorded at 570 nm. The fluorescence emission signal of the 20 nM TAMRA-Rev alone was subtracted from each signal obtained in the presence of increasing amounts of DABCYL-RRE and plotted as a function of DABCYL-RRE concentration (FIG. 21) in GraphPad PRISM™ using a non linear regression fit for single site binding. The results showed $K_d=137\pm23$ nM with an R2 value of 0.98.

Example 16

Assays Using DABCYL-TAR RNA and TAMRA-labelled Rev Peptide

Peptides derived from Rev are known to also be able to bind to TAR RNA. We therefore evaluated whether a complex could also be formed between DABCYL-TAR RNA and TAMRA-Rev peptide.

Figure 22:
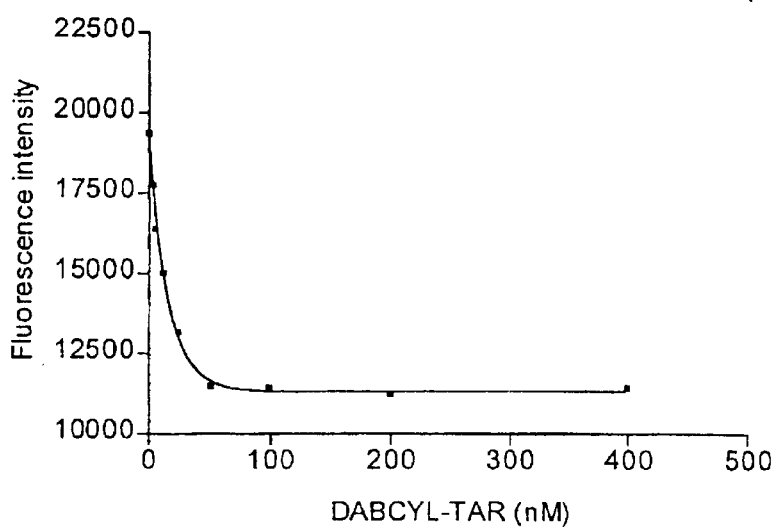
FIG. 22 shows a binding curve based on the quenching of 20 nM TAMRA-labelled Rev peptide and increasing concentrations of DABCYL-TAR RNA.

As shown in FIG. 22, the complex formed between DABCYL-TAR RNA and TAMRA-Rev peptide resulted in the proximal location of the two fluorophores such that the DABCYL significantly quenched the rhodamine fluorophore. 20 nM TAMRA-Rev was incubated with increasing concentrations of DABCYL-TAR. The TAMRA-Rev was pre-treated in the presence of 1% TFA at room temperature for 5 minutes prior to dilution into storage buffer (0.01% Triton X-100, 5 μg/ml BSA, 1% DMSO, 50 mM Tris-HCl pH 8, 50 mM KCl) and incubated on ice prior to complex formation. Reactions were equilibrated at room temperature for 15 minutes prior to analysis in the Wallac Victor2 plate reader. The reactions were excited at 544 nm and fluorescence emission recorded at 570 nm. The fluorescence emission signal of the 20 nM TAMRA-Rev alone was subtracted from each signal obtained in the presence of increasing amounts of DABCYL-TAR and plotted as a function of DABCYL-TAR concentration (FIG. 22) in GraphPad PRISM™ using a non linear regression fit for single site binding. The resulting $K_d=11$ μM with an R2 value of 0.98.

Example 17

High Throughput Screening Method

In order to handle the large numbers of samples required for high throughput screening it is useful to perform the competition binding assays in 96 well plates. This permits the use of manual multichannel pipettes and robotics to perform the liquid transfer steps.

Table 4 illustrates the format for a typical high throughput assay plate. The reaction conditions and volumes were as described in Example 11. The unprocessed/raw data is obtained from the LS50B fluorimeter measured at 532 nm in the presence of 10 nM DABCYL-TAR, 10 nM FAM-ADP-1 and increasing concentrations of RBT compounds (from 0.078 μM to 20 μM). The control samples contain 10 nM FAM-ADP-1 and 10 μM RBT compound and provide the maximum signal obtained in the absence of bound DABCYL-TAR RNA.

FIG. 23. is a graphical representation of the competition binding data obtained from the plate shown in Table 4. The eight compounds show unique $K_i$ values ranging from 1.57 to 0.42 μM.

A further microplate experiment is shown in Table 5 in which the binding of DABCYL-TAR to fluorescein ADP-1 is measured in the presence of a series of RBT compounds that exhibit a range of inhibitory activities.

The plates were assembled with 95 μl of a solution containing 10 nM Fluoresein-ADP-1 in the presence of 50 mM Tris-HCl pH7.5, 80 mM KCl, 1% DMSO 0.01% Triton X-100, 5 μg/mL BSA , 20 nM competitor RNA and 10 μM RBT compound in each well. Each column of the plate contained a series of eight wells with a specific RBT compound in each well of the column. Flourescence intensity in the absence of DABCYL-RNA ($I_0$) was determined by an initial measurement of the fluorescence using a 96-well plate reader (Wallac victor) with a fixed wavelength of 490 nm and emission at 535 nm. Flourescence intensity in the presence of DABCYL-RNA (I) was then measured following the addition of 5 μl of a 10 times concentration DABCYL-TAR RNA stock solution (corresponding to the amounts shown in Table 5). A fixed concentration of RNA was added to each row of the plate. Two sequential readings were taken in the presence and absence of added DABCYL-TAR RNA and then averaged for data processing.

Figure 24:
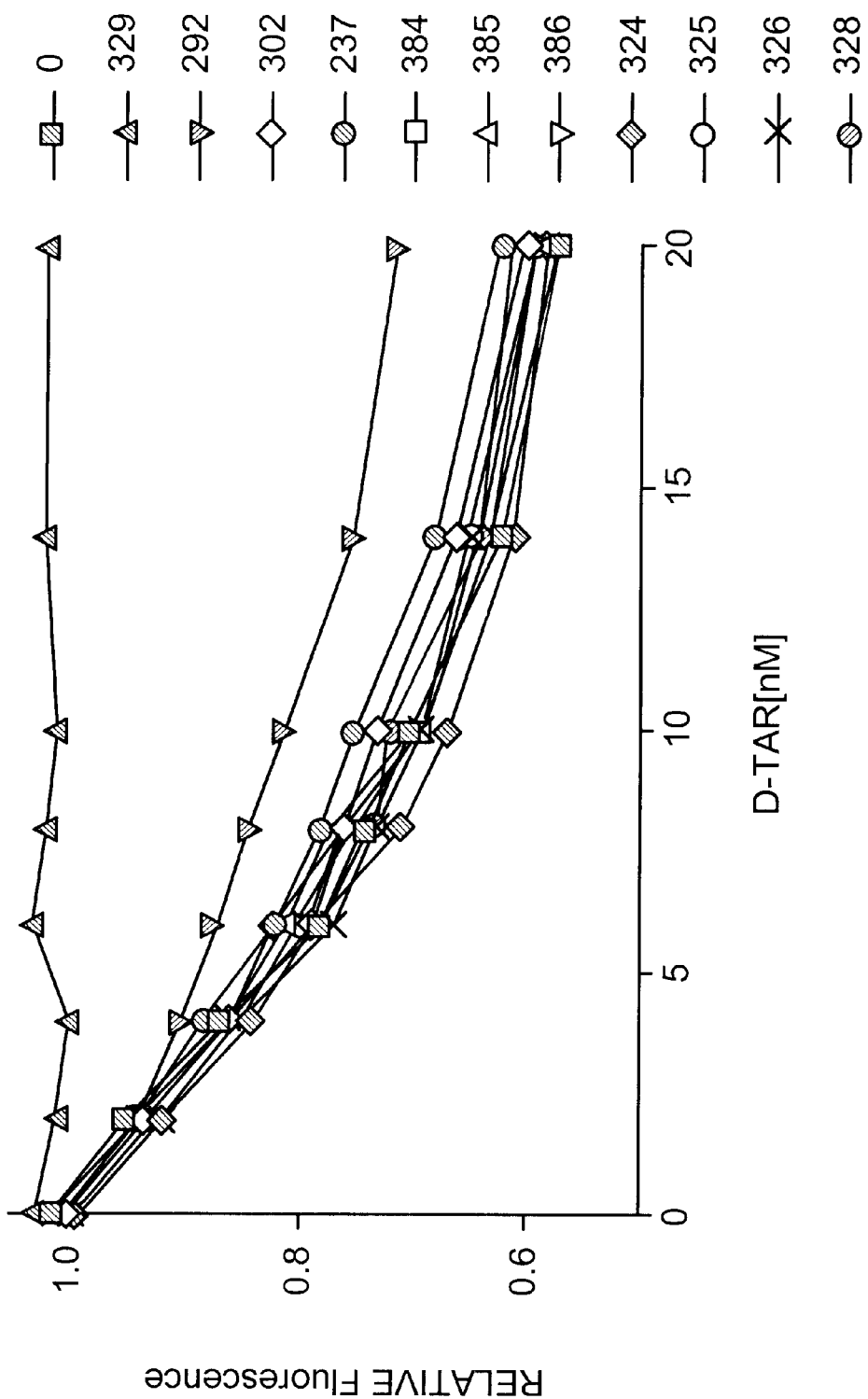
FIG. 24 shows the results from a high-throughput microplate assay testing a series of RBT compounds for their ability to inhibit the formation of an ADP-1/TAR complex.

FIG. 24. shows a plot of fluorescein fluorescence as a fraction of the original signal in the absence of DABCYL-RNA ($I/I_0$). The presence of certain compounds (RBT329, 292 and 237) causes a significant reduction in fluorescence quenching in comparison with the titration in the absence of compound, which is consistent with an inhibition of peptide-RNA complex formation.

Example 18

Selection of Reporter Molecules from a Combinatorial Library

Peptides carrying basic residues are able to bind RNA molecules and to discriminate between different RNA sequences. To determine whether short peptides carrying up to 9 basic residues are able to function as reporter molecules in the invention, a combinatorial library was designed comprising a series of linear peptides of 13 residues with the sequence:

Dabcyl-Thr-Arg-Lys-X-X-X-X-X-Arg-Lys-Ser-Gly (SEQ ID NO: 10)

where X is selected from the following amino acids: Arg, Lys, Gln.

Figure 25:
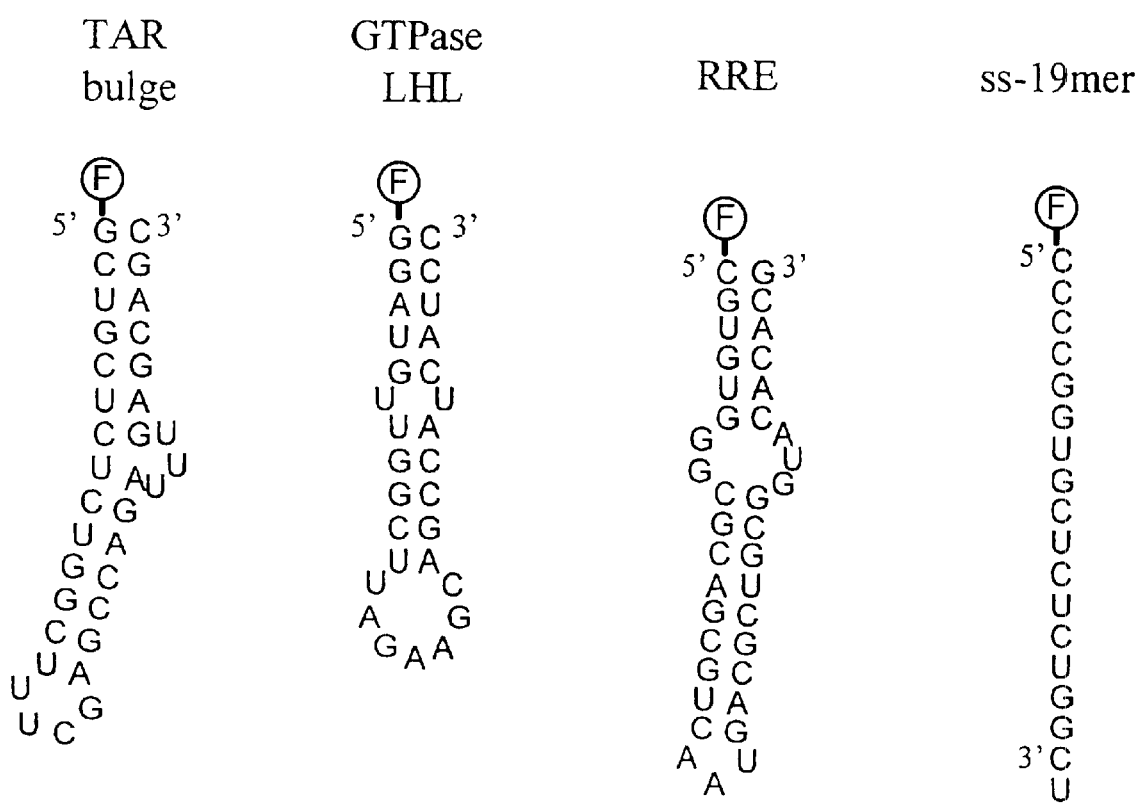
FIG. 25 shows the four RNA sequences tested using the K,Q,R-pentapeptide library. The RNAs are: TAR bulge (SEQ ID NO:51); GTPase LHL (SEQ ID NO:52), RRE (SEQ ID NO:6); ss-19mer (SEQ ID NO:53).

A representative subset comprising 40 peptide sequences from the total of 243 possible sequences was synthesised and is shown in Table 6. The peptides from the library are: No. 3 (SEQ ID NO:11), 4 (SEQ ID NO:12), 5 (SEQ ID NO:13), 6 (SEQ ID NO:14), 7 (SEQ ID NO:15), 8 (SEQ ID NO:16), 9 (SEQ ID NO:17), 10 (SEQ ID NO:18), 11 (SEQ ID NO:19), 12 (SEQ ID NO:20), 13 (SEQ ID NO:21), 14 (SEQ ID NO:22), 15 (SEQ ID NO:23), 16 (SEQ ID NO:24), 17 (SEQ ID NO:25), 18 (SEQ ID NO:26), 19 (SEQ ID NO:27), 20 (SEQ ID NO:28), 21 (SEQ ID NO:29), 22 (SEQ ID NO:30), 23 (SEQ ID NO:31), 24 (SEQ ID NO:32), 25 (SEQ ID NO:33), 26 (SEQ ID NO:34), 27 (SEQ ID NO:35), 28 (SEQ ID NO:36), 29 (SEQ ID NO:37), 30 (SEQ ID NO:38), 31 (SEQ ID NO:39), 32 (SEQ ID NO:40), 33 (SEQ ID NO:41), 34 (SEQ ID NO:42), 35 (SEQ ID NO:43), 36 (SEQ ID NO:44), 37 (SEQ ID NO:45), 38 (SEQ ID NO:46), 39 (SEQ ID NO:47), 40 (SEQ ID NO:48), 41 (SEQ ID NO:49), 42 (SEQ ID NO:50). These peptides were assayed for their ability to bind to range of RNA sequences carrying fluorescein attached to the 5' end, as shown in FIG. 25.

Figure 26:
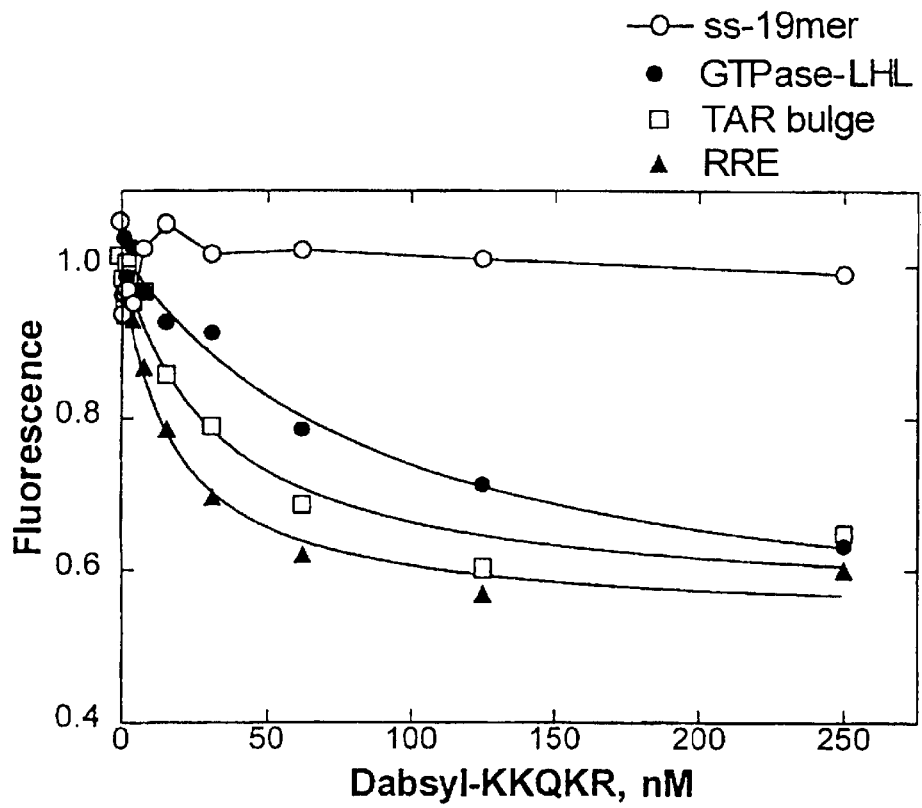
FIG. 26 shows binding data for the KKQKR sequence (SEQ ID NO:13) and the four RNA sequences of FIG. 25.

FIG. 26. presents binding data for the peptide sequence 5 (KKQKR) (SEQ ID NO: 13) and the 4 RNA sequences. Reactions (100 μl) containing Fam-labelled RNA (10 nM) were mixed with increasing concentrations of Dabcyl-labelled ADP-1 peptide (up to 250 nM) in 50 mM Tris/Cl, pH7.4, 20 mM or 110 mM KCl (as indicated), 5 μg/ml BSA, 0.01% Triton X-100, 1% DMSO. Fluorescence (excitation 490 nm/emission at 535 nm) was determined using a Victor plate reader.

There was no significant binding of the peptide, as measured by the quenching of the fluorescence on the fluorescenated RNA when single stranded RNA was used. The peptide was able to bind to each of the three remaining sequences with a characteristic affinity, with the highest affinity binding observed for the RRE sequence. Representative Kd values obtained using a range of peptide and RNA sequences are given in Table 7. Dissociation constants were determined by fitting a binding isotherm (1-site-binding) to the data using the equation:

$$Y=((Fmax-Fmin)-((Fmax-Fmin)*X/(Kd+X)))+Fmin$$

where Fmax is fluorescence in the absence of quencher, Fmin is fluorescence at saturation, and X is peptide concentration.

Figure 27:
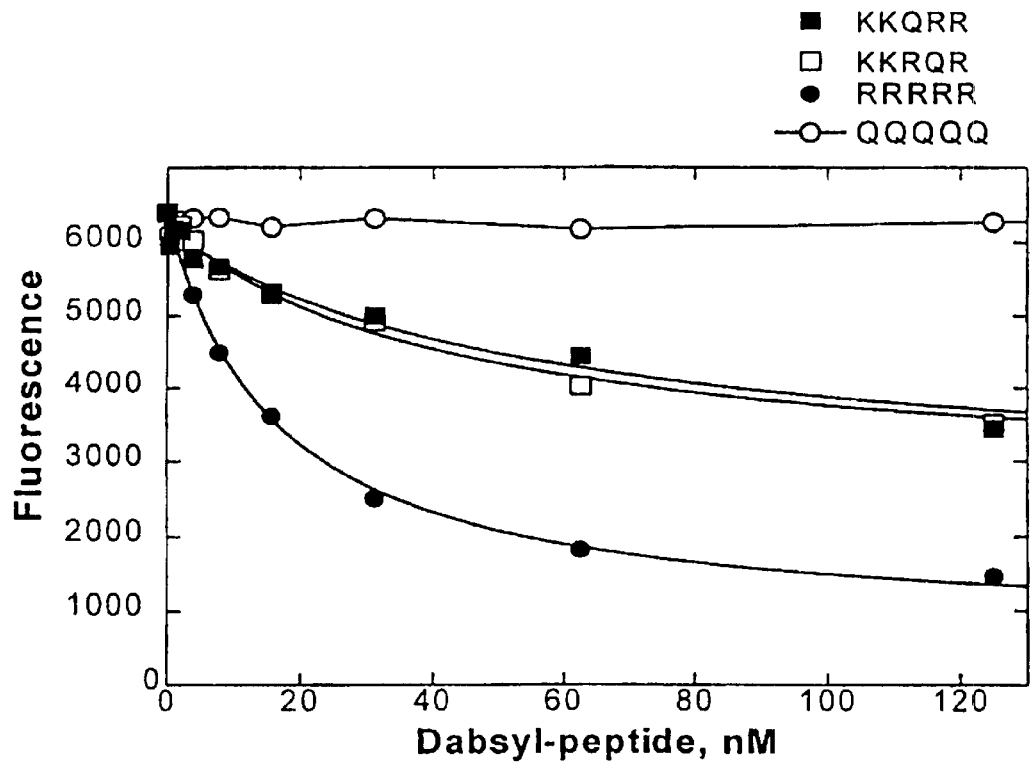
FIG. 27 shows binding data for 4 sequences from the library (KKQRR (SEQ ID NO:14), KKRQR (SEQ ID NO:15), RRRRR (SEQ ID NO:50), QQQQQ (SEQ ID NO:32)) and the GTPase RNA of FIG. 25.

FIG. 27 presents binding data for 4 different peptide sequences binding to the GTPase RNA. Efficient binding was obtained using the RRRRR sequence (SEQ ID NO: 50), but no significant binding was observed using the QQQQQ sequence (SEQ ID NO: 32),

TABLE 1

Typical values of $R_o$

| Donor | Acceptor | Ro (Å)* |
|---|---|---|
| Fluorescein | Tetramethylrhodamine | 55 |
| IAEDANS | Fluorescein | 46 |
| EDANS | DABCYL | 33 |

TABLE 1-continued

Typical values of $R_o$

| Donor | Acceptor | Ro (Å)* |
|---|---|---|
| Fluorescein | Fluorescein | 44 |
| BODIPY FL | BODIPY FL | 57 |

*$R_o$ is the distance at which 50% of excited donors are deactivated by FRET. Data from Haugland, RP. 1996. Handbook of Fluorescent Probes and Research Chemicals, 6th edition. Molecular Probes, Inc. Eugene OR, USA.

TABLE 2

FRET-pairs suitable for use in the method of this invention.

| Donor | Acceptor |
|---|---|
| (a) Fluorescent donors | |
| Fluorescein | Tetramethylrhodamine |
| Fluorescein | Cy-3 |
| EDANS | DABCYL |
| Dansyl | Fluorescein |
| Cy3 | Cy-5 |
| Tryptophan | AEDANS |
| Fluorescein | Tetramethyl rhodamine |
| Tetramethyl rhodamine | DABCYL |
| Fluorescein | DABCYL |
| DABCYL | Cy-3 |
| Fluorescein | Hexachlorofluorescein |
| Tetrachlorofluorescein | Cy-5 |
| (b) Luminescent donors | |
| Europium | Cy-5 |
| Terbium | Tetramethyl rhodamine |
| Terbium | Cy-3 |

TABLE 3

Evaluation of cyclic pentapeptides.

| Name | Sequence* | $K_i.(\mu M)$† |
|---|---|---|
| C5 (SEQ ID NO 9) | c(KRRFR) | 1.87 ± 0.42 |
| C5/1 | c(KRRFR) | 15.27 ± 2.5 |
| C5/2 | c(KRRFR) | 12.73 ± 6.58 |
| C5/3 | c(KRRFR) | 15.24 ± 3.79 |
| C5/4 | c(KRRFR) | 8.28 ± 3.01 |
| C5/5 | c(KRRFR) | 17.07 ± 13.00 |

*Underlined residues are D-amino acids
†Competition binding assays were performed in the presence of 2 nM FAM-labelled TAR RNA, 18 nM unlabelled TAR RNA, 20 nM TAMRA-labelled ADP-1 peptide and between 0 and 100 μM competitor cyclic peptide and the data was used to calculate $K_i$. Data is the average ± standard deviation for three determinations of $K_i$ using 12 concentrations of cyclic peptide in each experiment.

TABLE 4

Microplate data

| (μM)> | 0.078125 | 0.16025 | 0.3125 | 0.625 | 1.25 | 2.5 | 5 | 10 | 20 | Control 10 |
|---|---|---|---|---|---|---|---|---|---|---|
| RBT201 | 98.644 | 131.627 | 131.408 | 150.28 | 181.763 | 177.262 | 178.546 | 172.78 | 176.254 | 232.342 |
| RBT202 | 168.332 | 184.965 | 173.376 | 200.089 | 222.085 | 214.304 | 233.984 | 223.186 | 242.587 | 294.269 |
| RBT203 | 219.028 | 228.041 | 235.272 | 252.677 | 273.579 | 284.819 | 300.471 | 293.629 | 307.034 | 350.679 |
| RBT162 | 232.79 | 248.223 | 250.704 | 260.404 | 281.462 | 312.023 | 312.409 | 295.04 | 311.637 | 373.155 |
| RBT153 | 259.694 | 293.418 | 285.496 | 311.323 | 323.406 | 323.134 | 342.394 | 330.975 | 333.663 | 405.817 |
| RBT155 | 297.153 | 322.633 | 339.86 | 344.56 | 350.116 | 377.422 | 383.208 | 367.464 | 369.067 | 440.275 |
| RBT156 | 326.957 | 331.694 | 354.548 | 361.264 | 376.523 | 381.287 | 394.15 | 384.535 | 370.729 | 449.024 |
| RBT171 | 318.138 | 325.602 | 360.109 | 380.29 | 403.747 | 460.688 | 481.117 | 497.754 | 495.448 | 481.227 |

TABLE 5

Microplate data

| RNA (nM) | Control | RBT329 | RBT292 | RBT302 | RBT237 | RBT384 | RBT385 | RBT386 | RBT324 | RBT325 | RBT326 | RBT328 |
|---|---|---|---|---|---|---|---|---|---|---|---|---|
| | | | | | Flourescence Minus Dabeyl TAR RNA | | | | | | | |
| 0 | 14990 | 10492 | 14572 | 14839 | 14218 | 15812 | 15148 | 15078 | 15370 | 14597 | 15148 | 14985 |
| 0 | 15430 | 10608 | 14443 | 14447 | 13892 | 15315 | 14952 | 14869 | 15280 | 14857 | 14549 | 14927 |
| 0 | 14762 | 10540 | 14272 | 14273 | 13733 | 15323 | 15081 | 14567 | 15089 | 14832 | 14557 | 14766 |
| 0 | 15082 | 10336 | 14150 | 14641 | 14036 | 15468 | 15088 | 14829 | 15342 | 14419 | 14718 | 15840 |
| 0 | 15218 | 10454 | 14382 | 14338 | 14138 | 15634 | 15530 | 15425 | 15109 | 14811 | 14624 | 16261 |
| 0 | 14962 | 10425 | 14003 | 14423 | 14101 | 15769 | 15841 | 15376 | 15440 | 14860 | 15015 | 16163 |
| 0 | 15378 | 10464 | 14737 | 14588 | 14010 | 15765 | 15283 | 14982 | 15236 | 14830 | 15121 | 15055 |
| 0 | 15328 | 10796 | 14556 | 14786 | 14246 | 15892 | 15153 | 15289 | 15243 | 16154 | 15356 | 15418 |
| 0 | 14567 | 10223 | 14031 | 14070 | 13746 | 15402 | 14894 | 15031 | 15086 | 14862 | 14636 | 14270 |
| 0 | 15842 | 10360 | 13928 | 14270 | 13422 | 14946 | 14545 | 14510 | 14154 | 14281 | 14233 | 14554 |
| 0 | 14863 | 10303 | 13885 | 13888 | 13361 | 15185 | 15207 | 14702 | 14714 | 13971 | 14110 | 14253 |
| 0 | 14852 | 10278 | 14284 | 13814 | 13478 | 15121 | 14854 | 14867 | 14994 | 14408 | 14373 | 15477 |
| 0 | 14835 | 10295 | 13969 | 14210 | 13682 | 16322 | 15048 | 15098 | 15150 | 14462 | 14339 | 14589 |
| 0 | 14981 | 10644 | 14013 | 14226 | 13670 | 15864 | 15614 | 15022 | 15012 | 14423 | 14511 | 14848 |
| 0 | 15131 | 10396 | 14574 | 14261 | 13904 | 15628 | 14952 | 14658 | 15185 | 14524 | 14836 | 14489 |
| 0 | 15058 | 10750 | 14237 | 14588 | 13851 | 15581 | 15115 | 15021 | 15467 | 14790 | 14903 | 15130 |
| | | | | | Flourescence Plus Dabeyl TAR RNA | | | | | | | |
| 0 | 14906 | 10584 | 14563 | 14818 | 14222 | 15837 | 15294 | 16080 | 16588 | 15030 | 15041 | 14912 |
| 2 | 15002 | 10508 | 13532 | 13761 | 13080 | 14295 | 13806 | 13705 | 13852 | 13643 | 13316 | 13158 |
| 4 | 12779 | 10437 | 12755 | 12335 | 12135 | 13136 | 13068 | 12581 | 12880 | 12248 | 12184 | 12485 |
| 6 | 11755 | 10570 | 12400 | 11728 | 11399 | 12203 | 12093 | 11671 | 11901 | 11300 | 11398 | 12154 |
| 8 | 10918 | 10646 | 12025 | 10344 | 10637 | 11642 | 11575 | 11283 | 11206 | 10846 | 10743 | 10860 |
| 10 | 10279 | 10620 | 11455 | 10471 | 10443 | 10885 | 10915 | 10605 | 10058 | 10216 | 10129 | 11010 |
| 14 | 9621 | 10750 | 11139 | 9428 | 9411 | 9974 | 9496 | 9637 | 9214 | 9503 | 9555 | 9309 |
| 20 | 8682 | 10928 | 10308 | 8634 | 8675 | 9163 | 9119 | 9008 | 8900 | 8841 | 9120 | 9056 |
| 0 | 14979 | 10728 | 13871 | 14448 | 13871 | 15432 | 15321 | 16123 | 15381 | 14615 | 14476 | 14510 |
| 2 | 14774 | 10571 | 13261 | 13154 | 12701 | 14025 | 13611 | 13408 | 13863 | 12912 | 13270 | 13452 |
| 4 | 12731 | 10470 | 13679 | 11932 | 11664 | 13045 | 13078 | 12557 | 12418 | 11954 | 12084 | 12420 |
| 6 | 11470 | 10673 | 12291 | 11704 | 11051 | 12244 | 12138 | 11888 | 11658 | 11206 | 11140 | 12619 |
| 8 | 11172 | 10623 | 11831 | 10681 | 10871 | 11840 | 11831 | 11624 | 10937 | 10824 | 10492 | 10641 |
| 10 | 10548 | 10580 | 11213 | 10346 | 10407 | 10845 | 10957 | 10488 | 10202 | 10087 | 10354 | 10504 |
| 14 | 9365 | 10581 | 10932 | 9471 | 9581 | 9707 | 9448 | 9767 | 9237 | 9473 | 9509 | 9582 |
| 20 | 8716 | 10554 | 10187 | 8548 | 8187 | 8862 | 8831 | 8786 | 8931 | 8804 | 9248 | 8838 |

TABLE 6

A Library of RNA-binding peptides K, Q, R-pentapeptide sequences with constant flanking basic and neutral residues and the acceptor dye Dabsyl at the N-terminus Subset of 40 (Out of 243 = 3⁵) peptides chosen for custom synthesis

| No. | | | | | | | | | | | | | | | | |
|---|---|---|---|---|---|---|---|---|---|---|---|---|---|---|---|---|
| 3  | N-Dabsy | T | R | K | K | K | K | K | R | K | G | S | G | -Amid |
| 4  | N-Dabsy | T | R | K | K | K | K | Q | R | R | K | G | S | G | -Amid |
| 5  | N-Dabsy | T | R | K | K | K | Q | K | R | R | K | G | S | G | -Amid |
| 6  | N-Dabsy | T | R | K | K | K | Q | R | R | R | K | G | S | G | -Amid |
| 7  | N-Dabsy | T | R | K | K | K | R | Q | R | R | K | G | S | G | -Amid |
| 8  | N-Dabsy | T | R | K | K | Q | K | K | R | R | K | G | S | G | -Amid |
| 9  | N-Dabsy | T | R | K | K | Q | K | R | R | R | K | G | S | G | -Amid |
| 10 | N-Dabsy | T | R | K | K | Q | Q | Q | R | R | K | G | S | G | -Amid |
| 11 | N-Dabsy | T | R | K | K | Q | R | K | R | R | K | G | S | G | -Amid |
| 12 | N-Dabsy | T | R | K | K | Q | R | R | R | R | K | G | S | G | -Amid |
| 13 | N-Dabsy | T | R | K | K | R | K | Q | R | R | K | G | S | G | -Amid |
| 14 | N-Dabsy | T | R | K | K | R | Q | K | R | R | K | G | S | G | -Amid |
| 15 | N-Dabsy | T | R | K | K | R | Q | R | R | R | K | G | S | G | -Amid |
| 16 | N-Dabsy | T | R | K | K | R | R | Q | R | R | K | G | S | G | -Amid |
| 17 | N-Dabsy | T | R | K | Q | K | K | K | R | R | K | G | S | G | -Amid |
| 18 | N-Dabsy | T | R | K | Q | K | K | R | R | R | K | G | S | G | -Amid |
| 19 | N-Dabsy | T | R | K | Q | K | Q | Q | R | R | K | G | S | G | -Amid |
| 20 | N-Dabsy | T | R | K | Q | K | R | K | R | R | K | G | S | G | -Amid |
| 21 | N-Dabsy | T | R | K | Q | K | R | R | R | R | K | G | S | G | -Amid |
| 22 | N-Dabsy | T | R | K | Q | Q | K | Q | R | R | K | G | S | G | -Amid |
| 23 | N-Dabsy | T | R | K | Q | Q | Q | Q | R | R | K | G | S | G | -Amid |
| 24 | N-Dabsy | T | R | K | Q | Q | Q | Q | Q | R | K | G | S | G | -Amid |
| 25 | N-Dabsy | T | R | K | Q | Q | Q | R | R | R | K | G | S | G | -Amid |
| 26 | N-Dabsy | T | R | K | Q | Q | R | Q | R | R | K | G | S | G | -Amid |
| 27 | N-Dabsy | T | R | K | Q | R | K | Q | Q | Q | K | G | S | G | -Amid |
| 28 | N-Dabsy | T | R | K | Q | R | K | K | R | R | K | G | S | G | -Amid |
| 29 | N-Dabsy | T | R | K | Q | R | K | R | R | R | K | G | S | G | -Amid |
| 30 | N-Dabsy | T | R | K | Q | R | R | Q | Q | Q | K | G | S | G | -Amid |
| 31 | N-Dabsy | T | R | K | Q | R | R | K | R | R | K | G | S | G | -Amid |
| 32 | N-Dabsy | T | R | K | Q | R | R | R | R | R | K | G | S | G | -Amid |
| 33 | N-Dabsy | T | R | K | R | Q | K | K | R | R | K | G | S | G | -Amid |
| 34 | N-Dabsy | T | R | K | R | Q | K | R | R | R | K | G | S | G | -Amid |
| 35 | N-Dabsy | T | R | K | R | Q | Q | Q | Q | R | K | G | S | G | -Amid |
| 36 | N-Dabsy | T | R | K | R | Q | R | K | R | R | K | G | S | G | -Amid |
| 37 | N-Dabsy | T | R | K | R | Q | R | R | R | R | K | G | S | G | -Amid |
| 38 | N-Dabsy | T | R | K | R | R | K | Q | Q | R | K | G | S | G | -Amid |
| 39 | N-Dabsy | T | R | K | R | R | Q | K | R | R | K | G | S | G | -Amid |
| 40 | N-Dabsy | T | R | K | R | R | Q | R | R | R | K | G | S | G | -Amid |
| 41 | N-Dabsy | T | R | K | R | R | R | Q | R | R | K | G | S | G | -Amid |
| 42 | N-Dabsy | T | R | K | R | R | R | R | R | R | K | G | S | G | -Amid |

TABLE 7

Binding data for various RNA/peptide combinations (at 110 mM KCl)

| RNA | peptide | Kd | R2 |
|---|---|---|---|
| TAR | KQRQR | 9 | 0.92 |
| TAR | KQKRR | 11 | 0.96 |
| RRE | KKKKK | 12 | 0.98 |
| RRE | KKQKR | 15 | 0.97 |
| GTPase-LHL | RRRRR | 16 | 1.00 |
| TAR | KQKKR | 16 | 1.00 |
| RRE | KKQRR | 20 | 0.98 |
| RRE | KKRQR | 24 | 0.99 |
| TAR | KKKKK | 24 | 0.98 |
| GTPase-LHL | KKKKK | 26 | 0.99 |
| TAR | KKKQR | 27 | 0.99 |
| RRE | KKKQR | 30 | 1.00 |
| RRE | RRRRR | 30 | 0.98 |
| TAR | ADP1 | 35 | 0.92 |
| RRE | ADP1 | 39 | 0.99 |
| TAR | ADP1 | 41 | 0.99 |
| GTPase-LHL | KKRQR | 43 | 0.99 |
| GTPase-LHL | KKQRR | 55 | 0.98 |
| TAR | KKQKR | 56 | 0.98 |
| GTPase-LHL | KKQKR | 74 | 0.98 |
| GTPase-LHL | KKKQR | 76 | 0.99 |
| GTPase-LHL | ADP1 | 131 | 0.99 |
| ss-19mer | RRRRR | 194 | 0.97 |
| ss-19mer | ADP1 | 511 | 0.99 |
| TAR | QQQRR | >500 | N/A |
| TAR | QQQKR | >500 | N/A |
| TAR | RQQQR | >500 | N/A |
| TAR | KQQQR | >500 | N/A |
| ss-19mer | KKRQR | >500 | N/A |
| ss-19mer | KKQKR | >500 | N/A |
| ss-19mer | KKKKK | >500 | N/A |
| ss-19mer | KKQRR | >500 | N/A |
| ss-19mer | KKKQR | >500 | N/A |
| GTPase-LHL | QQQQQ | >500 | N/A |
| ss-19mer | QQQQQ | >500 | N/A |

REFERENCES

The patent and scientific literature referred to herein establishes the knowledge that is available to those with skill in the art. The contents of all references mentioned herein are incorporated by reference in their entirety.

Aboul-ela, F., Karn, J. & Varani, G. (1995). The structure of the human immunodeficiency virus type 1 TAR RNA reveals principles of RNA recognition by Tat protein. J. Mol. Biol., 253, 313–332.

Aboul-ela, F., Karn, J. & Varani, G. (1996). Structure of HIV-1 TAR RNA in the absence of ligands reveals a novel configuration of the trinucleotide bulge. Nucl. Acids Res., 24, 3974–3981.

Agrawal, S., Goodchild, J., Civiera, M. P., Thornton, A. H., Sarin, P. S. & Zamecnik, P. C. (1988). Oligodeoxynucleoside phosphoramidates and phosphorothioates as inhibitors of human immunodeficiency virus. Proc. Natl. Acad. Sci. USA, 85, 7079–7083.

Bartel, D. P., Zapp, M. L., Green, M. R. & Szostak, J. W. (1991). HIV-1 Rev regulation involves recognition of non-Watson-Crick base pairs in viral RNA. Cell, 67, 529–536.

Bassi, G. S., Murchie, A. I. H., Walter, F., Clegg, R. M. & Lilley, D. M. J. (1997). Ion-induced folding of the hammerhead ribozyme: a fluorescence resonance energy transfer study. EMBO J., 16, 7481–7489.

Battiste, J. L., Mao, H., Rao, N. S., Tan, R., Muhandiram, D. R., Kay, L. E., Frankel, A. D. & Williamson, J. R. (1996). α-helix-RNA major groove recognition in an HIV-1 Rev peptide-RRE RNA complex. 273, 1547–1551.

Battiste, J. L., Tan, R., Frankel, A. D. & Williamson, J. R. (1994). Binding of an HIV Rev peptide to Rev responsive element RNA induces formation of purine-purine base pairs. Biochemistry, 33, 2741–2747.

Bazemore, L. R, Takahashi, M. & Radding, C. M. (1997). Kinetic analysis of pairing and strand exchange catalysed by RecA. J. Biol. Chem., 272, 14672–14682.

Brodsky, A. S. & Williamson, J. R. (1997). Solution structure of the HIV-2 TAR-argininamide complex. J. Mol. Biol., 267, 624–639.

Burke, D. H., Hoffman, D. C., Brown, A., Hansen, M., Pardi, A. & Gold, L. (1997). RNA aptamers to the peptidyl transferase inhibitor chloramphenicol. Chem. Biol., 4, 833–843.

Cai, Z., Gorin, A., Frederick, R., Ye, X., Hu, W., Majumdar, A., Kettani, A. & Patel, D. J. (1998). Solution structure of P22 transcriptional antitermination N peptide-box B RNA complex. Nature Struct. Biol., 5, 203–212.

Calnan, B. J., Biancalana, S., Hudson, D. & Frankel, A. D. (1991a). Analysis of arginine-rich peptides from the HIV Tat protein reveals unusual features of RNA-protein recognition. Genes Develop., 5, 201–210.

Calnan, B. J., Tidor, B., Biancalana, S., Hudson, D. & Frankel, A. D. (1991b). Arginine-mediated RNA recognition: The arginine fork. Science, 252, 1107–1171.

Cardullo R. A., Agrawal, S., Flores, C., Zamecnik, P. C., Wolf, D. E. (1998). Detection of nucleic acid hybridization by nonradiative fluorescence resonance energy transfer. Proc. Natl. Acad. Sci. USA, 85, 8790–8794.

Chen, X. & Kwok, P.-Y. (1997). Template-directed dye-terminator incorporation (TDI) assay: a homogeneous DNA diagnostic method based on fluorescence resonance energy transfer. Nucl. Acids Res., 25, 347–353.

Chen, X., Zelmbauer, B., Qnirke, A. & Kwok, P.-Y. (1997). Fluorescence energy transfer detection as a homogenous DNA diagnostic method. Proc. Natl. Acad. Sci. USA, 94, 10756–10761.

Churcher, M., Lamont, C., Hamy, F., Dingwall, C., Green, S. M., Lowe, A. D., Butler, P. J. G., Gait, M. J. & Karn, J. (1993). High affinity binding of TAR RNA by the human immunodeficiency virus Tat protein requires amino acid residues flanking the basic domain and base pairs in the RNA stem. J. Mol. Biol., 230, 90–110.

Clegg, R. M. (1992). Fluorescence resonance energy transfer and nucleic acids. Methods Enzymol., 211, 353–388.

Connolly, B. A. & Newman, P. C. (1989). Synthesis and properties of oligonucleotides containing 4-thiothymidine, 5-methyl-2-pyrimidinone-1-beta-D(2'-deoxyriboside) and 2-thiothymidine. Nucl. Acids Res., 17,4957–4974.

Cordingley, M. G., LaFemina, R. L., Callahan, P. L., Condra, J. H., Sardana, V. V., Graham, D. J., Nguyen, T. M., LeGrow, K., Gotlib, L., Schlabach, A. J. & Colonno, R. J. (1990). Sequence specific interaction of Tat and Tat peptides with the TAR sequence of HIV-1 in vitro. Proc. Natl. Acad. Sci. USA, 87, 8985–8989.

Cullen, B. R. (1990). The HIV Tat protein: An RNA sequence-specific processivity factor? Cell, 63, 655–657.

De Guzman, R. N., Wu, Z. R., Stalling, C. C., Pappalardo, L., Borer, P. N. & Summers, M. F. (1998). Structure of the HIV-1 nucleocapsid protein bound to the SL3 ?-RNA recognition element. Science, 279, 384–388.

Delling, U., Reid, L. S., Barnett, R. W., Ma, M. Y.-X., Climie, S., Sumner-Smith, M. & Sonenberg, N. (1992). Conserved nucleotides in the TAR RNA stem of human immunodeficiency virus type 1 are critical for Tat binding and trans-activation: Model for TAR RNA tertiary structure. J. Virol., 66, 3018–3025.

Dingwall, C., Ernberg, I., Gait, M. J., Green, S. M., Heaphy, S., Karn, J., Lowe, A. D., Singh, M., Skinner, M. A. & Valerio, R. (1989). Human immunodeficiency virus 1 Tat protein binds trans-activation-responsive region (TAR) RNA in vitro. Proc. Natl. Acad. Sci. USA, 86, 6925–6929.

Drees, B. L., Rye, H. S., Glazer, A. N. & Nelson, H. C. M. (1996). Environment-sensitive labels in multiplex fluorescence analyses of protein-DNA complexes. J. Biol. Chem., 271, 32168–32173.

Duckett, D. R., Murchie, A. I. & Lilley, D. M. J. (1995). The global folding of four-way helical junctions in RNA, including that in U1 snRNA. Cell, 83, 1027–1036.

Gait, M. J., Earnshaw, D. J., Farrow, M. A., Fogg, J. H., Grenfell, R. L., Naryshkin, N. A. & Smith, T. V. (1998). Applications of chemically synthesised RNA. In RNA-Protein Interactions: A Practical Approach, ed. C. Smith, pp 1–36. Oxford: Oxford University Press.

Gait, M. J., Jones, A. S. & Walker, R. T. (1974). Synthetic-analogues of polynucleotides XII. Synthesis of thymidine derivatives containing an oxyacetamido- or an oxyformamido-linkage instead of a phosphodiester group. J. Chem. Soc. Perkin I, 14, 1684–1686.

Gohlke, C., Murchie, A. I. H., Lilley, D. M. J. & Clegg, R. M. (1994). Kinking of DNA and RNA helices by bulged nucleotides observed by fluorescence resonance energy transfer. Proc. Natl. Acad. Sci. USA, 91, 11660–11664.

Gold, L., Polisky, B., Uhlenbeck, O. & Yarus, M. (1995). Diversity of oligonucleotide functions. Annu. Rev. Biochem., 64, 763–797.

Grasby, J. A., Butler, P. J. G. & Gait, M. J. (1993). The synthesis of oligoribonucleotides containing 06-methylguanosine: the role of conserved guanosine residues in hammerhead ribozyme cleavage. Nucl. Acids Res., 21, 4444–4450.

Hamy, F., Asseline, U., Grasby, J., Iwai, S., Pritchard, C., Slim, G., Butler, P. J. G., Karn, J. & Gait, M. J. (1993). Hydrogen-bonding contacts in the major groove are required for human immunodeficiency virus type-1 Tat protein recognition of TAR RNA. J. Mol. Biol., 230, 111–123.

Hamy, F., Felder, E., Heizmann, G., Lazdins, J., Aboulela, F., Varani, G., Karn, J. & Klimkait, T. (1997). Identification of an inhibitor of the Tat/TAR RNA interaction that effectively suppresses HIV-1 replication. Proc. Natl. Acad. Sci. USA, 94, 3548–3553.

Heaphy, S., Dingwall, C., Emberg, I., Gait, M. J., Green, S. M., Karn, J., Lowe, A. D., Singh, M. & Skinner, M. A. (1990). HIV-1 regulator of virion expression (Rev) protein binds to an RNA stem-loop structure located within the Rev-response element region. Cell, 60, 685–693.

Heaphy, S., Finch, J. T., Gait, M. J., Karn, J. & Singh, M. (1991). Human immunodeficiency virus type 1 regulator of virion expression, Rev, forms nucleoprotein filaments after binding to a purine-rich "bubble" located within the Rev-responsive region of viral RNA. Proc. Natl Acad. Sci. USA, 88, 7366–7370.

Hélene, C., Montenay-Garestier, T., Saison, T., Takasugi, M., Toulmé, J. J., Asseline, U., Lancelot, G., Maurizot, J. C, Toulmé, F. & Thuong, N. T. (1985). Oligodeoxynucleotides covalently linked to intercalating agents: a new class of gene regulatory substances. Biochimie, 67, 777–783.

Heyduk, E. & Heyduk, T. (1997). Thiol-reactive, luminescent europium chelates: luminescence probes for resonance energy transfer distance measurements in biomolecules. Anal. Biochem., 248, 216–227.

Houghten, R. A., Pinilla, C., Blondelle, S. E., Appel, J. R., Dooley, C. T. & Cuervo, J. H. (1991). Generation and use of synthetic peptide combinatorial libraries for basic research and drug discovery. Nature, 354, 84–86.

Iwai, S., Pritchard, C., Mann, D. A, Karn, J. & Gait, M. J. (1992). Recognition of the high affinity binding site in Rev-response element RNA by the human immunodeficiency virus type-1 Rev protein Nucl. Acids Res., 20, 6465–6472.

Jain, C. & Belasco, J. G. (1996). A structural model for the HIV-1 Rev-RRE complex deduced from altered specificity Rev variants isolated by a rapid genetic strategy. Cell, 87, 115–125.

Jensen, K. B., Green, L., MacDougal-Waugh, S. & Tuerk, C. (1994). Characterisation of an in vitro-selected RNA ligand to the HIV-1 Rev protein. J. Mol. Biol., 234, 235–247.

Karn, J., Gait, M. J., Churcher, M. J., Mann, D. A., Mikaélian, I. & Pritchard, C. (1995). Control of human immunodeficiency virus gene expression by the RNA-binding proteins Tat and Rev. In RNA-protein Interactions, ed. A. Nagai and I. Mattaj, pp 192–220. Oxford: Oxford University Press.

Kessler, H., Gratias, R., Hessler, G., Gurrath, M. & Müller, G. (1996). Conformation of cyclic peptides. Principle concepts and the design of selectivity and superactivity in bioactive sequences by 'spatial screening'. Pure Appl. Chem., 68, 1201–1205.

Kjems, J., Brown, M., Chang, D. D. & Sharp, P. A. (1991). Structural analysis of the interaction between the human immunodeficiency virus Rev protein and the Rev-response element, Proc. Natl. Acad. Sci. USA, 88, 683–687.

Kjems, J., Calnan, B. J., Frankel, A. D. & Sharp, P. A. (1992). Specific binding of a basic peptide from HIV-1 Rev. EMBO J., 11, 1119–1129.

Lamm, G. M., Blencowe, B. J., Sproat, B. S., Iribarren, A. M., Ryder, U. & Lamond, A. I. (1991). Antisense probes containing 2-aminoadenosine allow efficient depletion of U5 snRNP from HeLa splicing extracts. Nucl. Acids Res., 19, 3193–3198.

Lee, B. L., Murakami, A., Blake, K. R., Lin, S. B. & Miller, P. S. (1988). Interaction of psoralen-derivatized oligodeoxyribonucleoside methylphosphonates with single-stranded DNA. Biochemistry, 27, 3197–3203.

Mag, M. & Engels, J. W. (1988). Synthesis and structure assignments of amide protected nucleosides and their use as phosphoramidites in deoxyoligonucleotide synthesis. Nucl. Acids Res., 16, 3525–3543.

Malim, M. H., Böhnlein, S., Hauber, J. & Cullen, B. R. (1989a). Functional dissection of the HIV-1 Rev trans-activator: Derivation of a trans-dominant repressor of Rev function. Cell, 58, 205–214.

Malim, M. H. & Cullen, B. R. (1991). HIV-1 structural gene expression requires the binding of multiple Rev monomers to the viral RRE: Implications for HV-1 latency. Cell, 65, 241–248.

Malim, M. H., Hauber, J., Le, S.-Y., Maizel, J. V. & Cullen, B. R. (1989b). The HIV-1 Rev trans-activator acts through a structured target sequence to activate nuclear export of unspliced viral mRNA. Nature, 338, 254–257.

Mann, D. A., Mikaélian, I., Zemmel, R. W., Green, S. M., Lowe, A. D., Kimura, T., Singh, M., Butler, P. J. G., Gait, M. J. & Karn, J. (1994). A molecular rheostat: Co-operative Rev binding to Stem I of the Rev-response element modulates human immunodeficiency virus type-1 late gene expression. J. Mol. Biol., 241, 193–207.

Mei, H.-Y., Mack, D. P., Galan, A. D., Halim, N. S., Heldsinger, A., Loo, J. A., Moreland, D. W., Sannes-Lowery, K. A., Sharmeen, L., Truong, H. N. & Czarnik, A. W. (1997). Discovery of selective, small-molecule inhibitors of RNA complexes-I. The Tat protein/TAR RNA complexes required for HIV-1 transcription. Bioorganic & Med. Chem., 5, 1173–1184.

Metzger, A. U., Bayer, P., Willbold, D., Hoffmann, S., Frank, R. W., Goody, R. S. & Rösch, P. (1997). The interaction of HIV-1 Tat (32–72) with its target RNA: a fluorescence and nuclear magnetic resonance study. Biochem. Biophys. Res. Comm., 241, 31–36.

Miller, P. S., Chandrasegaran, S., Dow, D. L., Pulford, S. M. & Kim, L. S. (1982). Synthesis and template properties of an ethyl phosphotriester modified decadeoxyribonucleotide. Biochemistry, 21, 5468–5474.

Miller, P. S., Dreon, N., Pulford, S. M. & McParland, K. B. (1980). Oligothymidylate analogues having stereoregular, alternating methylphosphonate/phosphodiester backbones. Synthesis and physical studies. J. Biol. Chem., 255, 9569–9665.

Perrouault, L., Asseline, U., Rivalle, C., Thuong, N. T., Bisagni, E., Giovannangeli, C., Le Doan, T. & Hélene, C. (1990). Sequence-specific artificial photo-induced endonucleases based on triple helix-forming oligonucleotides. Nature, 344, 358–360.

Peterson, R. D. & Feigon, J. (1996). Structural change in Rev responsive element RNA of HIV-1 on binding of Rev peptides. J. Mol. Biol., 264, 863–877.

Piccirilli, J. A., Krauch, T., Moroney, S. E. & Benner, S. A. (1990). Enzymatic incorporation of a new base pair into DNA and RNA extends the genetic alphabet. Nature, 343, 33–37.

Pritchard, C. E., Grasby, J. A., Hamy, F., Zachareck, A. M., Singh, M., Karn, J. & Gait, M. J. (1994). Methylphosphonate mapping of phosphate contacts critical for RNA recognition by the human immunodeficiency virus Tat and Rev proteins. Nucl. Acids Res., 22, 2592–2600.

Puglisi, J. D., Tan, R., Calnan, B. J., Frankel, A. D. & Williamson, J. R. (1992). Conformation of the TAR RNA-arginine complex by NMR spectroscopy. Science, 257, 76–80.

Purohit, P. & Stern, S. (1994). Interactions of a small RNA with antibiotic and RNA ligands of the 30S subunit. Nature, 370, 659–662.

Rogers, J., Chang, A. H., von Ahsen, U., Schroeder, R. & Davies, J. (1996). inhibition of the self-cleavage reaction of the human Hepatitis delta virus ribozyme by antibiotics. J. Mol. Biol., 259, 916–925.

Sannes-Lowery, K. A., Hu, P., Mack, D. P., Mei, H.-Y. & Loo, J. A. (1997). HIV-1 Tat peptide binding to TAR RNA by electrospray ionization mass spectroscopy. Anal. Chem., 69, 5130–5135.

Schmidt, S., Grenfell, R. L., Smith, T. V., Grasb, J. A., Mersmann, K. & Gait, M. J. (1996). Solid phase synthesis of oligoribonucleotides containing site-specific modifications. In Innovation and Perspectives in Solid Phase Synthesis and Combinatorial Libraries, ed. R. Epton, pp 11–18. Birmingham: Mayflower Scientific Ltd.

Schmidt, S., Niemann, A., Krynetskaya, N. F., Oretskaya, T. S., Metelev, V. G., Suchomlinov, V. V., Shabarova, Z. A. & Cech, D. (1992). The use of oligonucleotide probes containing 2'-deoxy-2'-fluoronucleosides for regiospecific cleavage of RNA by RNase H from *Escherichia coli*. Biochim Biophys Acta, 1130, 41–46.

Selvin, P. R. (1995). Fluorescence resonance energy transfer. Methods Enzymol. 246, 300–335.

Simon, R. J., Kania, R. S., Zuckerman, R. N., Huebner, V. D., Jewell, D. A., Banville, S., Ng, S., Wang, L., Rosenberg, S., Marlowe, C. K., Spellmeyer, D. C., Tan, R., Frankel, A. D., Santi, D. V., Cohen, F. E. & Bartlett, P. A. (1992). Peptoids: a modular approach to drug discovery. Proc. Natl. Acad. Sci. USA, 89, 9367–9371.

Slim, G., Pritchard, C., Biala, E., Asseline, U. & Gait, M. J. (1991). Synthesis of site-specifically modified oligoribonucleotides for studies of the recognition of TAR RNA by HIV-1 Tat protein and studies of hammerhead ribozymes. Nucl. Acids Res. Symp. Series, 24, 55–58.

Sproat, B. S., Iribarren, A. M., Garcia, R. G. & Beijer, B. (1991). New synthetic routes to synthons for 2'-O-allyloligoribonucleotide assembly. Nucl. Acids Res., 19, 733–738.

Sproat, B. S., Lamond; A. L, Beijer, B., Neuner, P. & Ryder, U. (1989). Highly efficient chemical synthesis of 2'-O-methyloligoribonucleotides and tetrabiotinylated derivatives; novel probes that are resistant to degradation by RNA or DNA specific nucleases. Nucl. Acids Res., 17, 3373–3386.

Stein, C. A., Subasinghe, C., Shinozuka, K. & Cohen, J. S. (1988). Physicochemical properties of phosphorothioate oligodeoxynucleotides. Nucl. Acids Res., 16, 3209–3221.

Stryer, L. (1978). Fluorescence energy transfer as a spectroscopic ruler. Ann. Rev. Biochem. 47, 819–846.

Sumner-Smith, M., Roy, S., Barnett R., Reid, L. S., Kuperman, R., Delling, U. & Sonenberg, N. (1991). Critical chemical features in trans-acting-responsive RNA are required for interaction of human immunodeficiency virus type 1 Tat protein. J. Virol., 65, 5196–5202.

Sun, J.-S., Francois, J.-C., Lavery, R., Saison-Behmoaras, T., Montenay-Garestier, T., Thuong, N. T. & Hélene, C. (1988). Sequence-targeted cleavage of nucleic acids by oligo-alpha-thymidylate-phenanthroline conjugates: parallel and antiparallel double helices are formed with DNA and RNA, respectively. Biochemistry, 27, 6039–6045.

Tan, R., Chen, L., Buettner, J. A., Hudson, D. & Frankel, A. D. (1993). RNA recognition by an isolated ?-helix. Cell, 73, 1031–1040.

Tuerk, C., MacDougal, S. & Gold, L. (1992). RNA pseudoknots that inhibit human inununodeficiency virus type 1 reverse transcriptase. Proc. Natl. Acad. Sci. USA, 89, 6988–6992.

Tuschl, T., Gohlke, C., Jovin, T. M., Westhof, E. & Eckstein, F. (1994). A three-dimensional model of the hammerhead ribozyme based on fluorescence measurements. Science, 266, 785–789.

Tyagi, S. & Kramer, F. R. (1996). Molecular beacons: probes that fluoresce upon hybridization. Nature Biotech. 14, 303–308.

Vlassov, V. V., Gaidamakov, S. A., Zarytova, V. F., Knorre, D. G., Levina, A. S., Nikonova, A. A., Podust, L. M. & Fedorova, O. S. (1988). Sequence-specific chemical modification of double-stranded DNA with alkylating oligodeoxyribonucteotide derivatives. Gene, 72, 313–322.

von Ahsen, U. & Schroeder, R. (1991). Streptomycin inhibits splicing of group I introns by competition with the guanosine substrate. Nucl. Acids Res., 19, 2261–2265.

von Roedern, E. G., Lohof, B., Hessler, U., Hoffmann, M. & Kessler, H. (1996). Synthesis and conformational analysis of linear and cyclic peptides containing sugar amino acids. J. Am. Chem. Soc., 118, 10156–10167.

Wang, Y., Hamasaki, K. & Rando, R. R. (1997). Specificity of aminoglycoside binding to RNA constructs derived from the 16S rRNA decoding region and the HIV-RRE activator Region. Biochemistry, 36, 768–779.

Wank, H., Rogers, J., Davies, J. & Schroeder, R. (1994). Peptide antibiotics of the tuberactinomycin family as inhibitors of group I intron RNA splicing. J. Mol. Biol., 236, 1001–1010.

Weeks, K. M., Ampe, C., Schultz, S. C., Steitz, T. A. & Crothers, D. M. (1990). Fragments of the HIV-1 Tat protein specifically bind TAR RNA. Science, 249, 1281–1285.

Weeks, K. M. & Crothers, D. M. (1991). RNA recognition by Tat-derived peptides: Interaction in the major groove? Cell, 66, 577–588.

Werstuck, G., Zapp, M. L. & Green, M. R. (1996). A noncanonical base pair within the human immunodeficiency virus Rev-responsive element is involved in both Rev and small molecule recognition. Chem. Biol., 3, 129–137.

Yang, M. & Millar, D. P. (1997). Fluorescence resonance energy transfer as a probe of DNA structure and function. Methods Enzymol., 278, 417–445.

Yang, Y., Kochoyan, M., Burgstaller, P., Westhof, E. & Famulok, M. (1996). Structural basis of ligand discrimination by two related RNA aptamers resolved by NMR spectroscopy. Science, 1343–1347.

Ye, X., Gorin, A., Ellington, A. D. & Patel, D. J. (1996). Deep penetration of an a-helix into a widened RNA major groove in the HIV-1 Rev peptide-RNA aptamer complex. Nature Struct. Biol., 3, 1026–1033.

Zapp, M. L., Stern, S. & Green, M. R. (1993). Small molecules that selectively block RNA binding of HIV-1 Rev protein inhibit Rev function and viral production. Cell, 74, 969–978.

Zemmel, R. W., Kelley, A. C., Karn, J. & Butler, P. J. G. (1996). Flexible regions of RNA structure facilitate co-operative Rev assembly on the Rev-response element. J. Mol. Biol., 258, 763–777.

What is claimed is:

1. A method for determining whether a test compound binds to a target RNA, the Sethod comprising the steps of:
   (a) contacting the test compound with a pair of indicator molecules comprising a reporter labelled with a donor group or an acceptor group and the target RNA labelled with a complementary acceptor or donor group, wherein said reporter is not an oligonucleotide that has a sequence which is able to hybridize via Watson-Crick base-pairing under stringent conditions to an unfolded target RNA, the pair being capable of binding to each other in an orientation that pennits the donor group to come into sufficient proximity to the acceptor group to permit fluorescent resonance energy transfer and/or quenching to take place; and
   (b) measuring the fluorescence of the target RNA and the reporter molecule in the presence of the test compound and comparing this value to the fluorescence of a standard; thereby determining whether said test compound binds said target RNA.

2. A method according to claim 1, in which the standard comprises the indicator pair in the presence or absence of test compound, the fluorescently-labelled target RNA, in the presence or absence of test compound, fluorescently-labelled reporter molecule in the presence or absence of test compound.

3. A method for the identification of a compound that binds to a target RNA from within a plurality of test compounds, comprising the steps of the method according to claim 1 preceded by the initial step of providing a plurality of test compounds.

4. A method according to any of claims 1 or 3, comprising the steps of
   (a) contacting a test compound with an indicator complex, the indicator complex comprising a fluorescently-labelled reporter molecule bound to a fluorescently labelled target RNA in an orientation that permits the fluorescent groups present on each molecule to come into sufficient proximity to permit fluorescent resonance energy transfer to take place; and
   (b) measuring the fluorescence of the target RNA and the reporter molecule in the presence of the test compound and comparing this value to the fluorescence of a standard.

5. A method according to any one of claims 1 or 3, wherein the reporter comprises a peptide, a basic peptide, a protein, a lipid, a polysaccharide, an oligonucleotide, an oligonucleotide derivative, or a small organic molecule.

6. A method according to claim 5, in which the reporter comprises a linear peptide or derivative thereof, a cyclic peptide or derivative thereof, a linear or cyclic peptoid or derivative thereof, or a peptidomimetic analogue.

7. A method according to any one of claims 1 or 3, in which the reporter binds the target RNA with a Kd of between $1 \times 10^{-12}$ and $1 \times 10^{-4}$ M.

8. A method according to any one of claims 1 or 3, in which the target RNA is between 5 and about 500 nucleotides in length.

9. A method according to any one of claims 1 or 3, in which the target RNA is chemically modified.

10. A method according to any one of claims 1 or 3, in which the target RNA is derived from fungal, viral, bacterial, or eukaryotic RNA.

11. A method according to claim 10, in which the target RNA is a viral RNA from a region of the TAR of HIV.

12. A method for determining whether a test compound binds to a target RNA that is a viral RNA from a region of the TAR of HIV, the method comprising the steps of:
   (a) contacting the test compound with a pair of indicator molecules comprising a reporter labelled with a donor group or an-acceptor group and the target RNA labelled with a complementary acceptor or donor group, wherein said target RNA is selected from the group consisting of: (a) SEQ ID NO: 1 and FAM-labelled SEQ ID NO: 2; (b) SEQ ID NO: 3 and FAM-labelled SEQ ID NO: 4; (c) SEQ ID NO: 5, labelled with Cy3, FAM or DABCYL; and the reporter is SEQ ID NO: 7, labelled with FAM, DABCYL or TAMRA, the pair being capable of binding to each other in an orientation that permits the donor group to come into sufficient proximity to the acceptor group to permit fluorescent resonance energy transfer and/or quenching to take place; and
   (b) measuring the fluorescence of the target RNA and the reporter molecule in the presence of the test compound and comparing this value to the fluorescence of a standard; thereby determining whether said test compound binds said target RNA.

13. A method according to claim 10, in which the target RNA is a viral RNA from a region of the RRE of HIV.

14. A method according to claim 13, wherein the target RNA and reporter are selected from:

| Target RNA | Reporter |
|---|---|
| SEQ ID DABCYL-6 | SEQ ID TAMRA-8; |
| SEQ ID DABCYL-6 | SEQ ID FAM-8; |
| SEQ ID Cy3-6 | SEQ ID FAM-8; and |
| SEQ ID FAM-6 | SEQ ID TAMRA 8. |

15. A method according to any one of claims 1 or 3, in which the target RNA and the reporter molecule are fluorescently labelled by covalent attachment of a fluorescent group.

16. A method according to claim 15, in which the target RNA is fluorescently labelled at the 3' or 5' end of a strand within the target RNA, or within the chain of the target RNA.

17. A method according to any one of claims 1 or 3, in which the the reporter molecule or the target RNA molecule is adhered to a solid support.

18. A method according to any one of claims 1 or 3, in which either (i) the donor is attached to the target RNA, and the acceptor is attached to the reporter molecule, or (ii) the donor is attached to the reporter molecule, and the acceptor is attached to the target RNA.

19. A method according to any one of claims 1 or 3, in which the acceptor is able to quench the fluorescence of the donor after binding of the target RNA and the reporter.

20. A method according to any one of claims 1 or 3, in which the target RNA, the reporter, and the test compound are mixed, and the fluorescence of the mixture is compared to standards.

21. A method according to any one of claims 1 or 3, in which the test compound is first mixed with the labelled RNA in order to form a complex in the absence of the labelled reporter, and the reporter is then added.

22. A method according to any one of claims 1 to 19, in which a complex is pre-formed between the labelled RNA and the labelled reporter molecule before addition of the test compound.

23. A kit for determining whether a test compound binds to a target RNA, the kit comprising (a) a target RNA labelled with a donor group or an acceptor group and (b) a reporter labelled with a complementary acceptor or donor group, wherein said reporter is not an oligonucleotide that has a sequence which is able to hybridize via Watson-Crick base-pairing under stringent conditions to an unfolded target RNA, and wherein the reporter and the target RNA are capable of binding to each other in an orientation that permits the donor group to come into sufficient proximity to the acceptor group to permit fluorescent resonance energy transfer and/or quenching.

24. A method for determining the presence in a biological sample of a compound that binds to a target RNA molecule, comprising
   (a) contacting the sample with a pair of indicator molecules comprising a reporter labelled with a donor group or an acceptor group and the target RNA labelled with a complementary acceptor or donor group, wherein said reporter is not an oligonucleotide that has a sequence which is able to hybridize via Watson-Crick base-pairing under stringent conditions to an unfolded target RNA, the pair being capable of binding to each other in an orientation that permits the donor group to come into sufficient proximity to the acceptor group to permit fluorescent resonance energy transfer and/or quenching to take place; and (b) measuring the fluorescence of the target RNA and the reporter molecule in said step (a) to obtain a fluorescence value and comparing this value to the fluorescence of a standard wherein a difference in said value and the fluorescence of said standard is an indication of the presence in a biological sample of a compound that binds to said target RNA.

25. The method of claim 24, said biological sample comprising a tissue or fluid from a mammal.

* * * * *

SEQUENCE LISTING

```
<160> NUMBER OF SEQ ID NOS: 53

<210> SEQ ID NO 1
<211> LENGTH: 17
<212> TYPE: RNA
<213> ORGANISM: Human immunodeficiency virus

<400> SEQUENCE: 1
agccagauuu gagcagc                                                    17

<210> SEQ ID NO 2
<211> LENGTH: 14
<212> TYPE: RNA
<213> ORGANISM: Human immunodeficiency virus

<400> SEQUENCE: 2
gcugcucucu ggcu                                                       14
```

```
<210> SEQ ID NO 3
<211> LENGTH: 18
<212> TYPE: RNA
<213> ORGANISM: Human immunodeficiency virus

<400> SEQUENCE: 3
agccagauuu gagcagcg                                                      18

<210> SEQ ID NO 4
<211> LENGTH: 15
<212> TYPE: RNA
<213> ORGANISM: Human immunodeficiency virus

<400> SEQUENCE: 4
cgcugcucuc uggcu                                                         15

<210> SEQ ID NO 5
<211> LENGTH: 29
<212> TYPE: RNA
<213> ORGANISM: Human immunodeficiency virus

<400> SEQUENCE: 5
cccagaucug agccugggag cucucuggg                                          29

<210> SEQ ID NO 6
<211> LENGTH: 38
<212> TYPE: RNA
<213> ORGANISM: Human immunodeficiency virus

<400> SEQUENCE: 6 cguguggggcg cagcgucaau gacgcugcgg uacacacg                               38

<210> SEQ ID NO 7
<211> LENGTH: 35
<212> TYPE: PRT
<213> ORGANISM: Human immunodeficiency virus

<400> SEQUENCE: 7

Phe Thr Thr Lys Ala Leu Gly Ile Ser Tyr Gly Arg Lys Lys Arg Arg
 1               5                  10                  15

Gln Arg Arg Arg Pro Pro Gln Gly Ser Gly Thr His Gln Val Ser Leu
             20                  25                  30

Ser Lys Gln
         35

<210> SEQ ID NO 8
<211> LENGTH: 18
<212> TYPE: PRT
<213> ORGANISM: Human immunodeficiency virus

<400> SEQUENCE: 8

Asp Thr Arg Gln Ala Arg Arg Asn Arg Arg Arg Arg Trp Arg Glu Arg
 1               5                  10                  15

Gln Arg

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:C5 cyclic
      peptide
```

```
<400> SEQUENCE: 9

Lys Arg Arg Phe Arg
1               5

<210> SEQ ID NO 11
<211> LENGTH: 13
<212> TYPE: PRT
<213> ORGANISM: Artificial Sequence
<220> FEATURE:
<221> NAME/KEY: SITE
<222> LOCATION: (4)..(8)
<223> OTHER INFORMATION: Xaa represents lys, gln, or arg
<220> FEATURE:
<223> OTHER INFORMATION: Description of Artificial Sequence:K, Q,
      R-pentapeptide library

<400> SEQUENCE: 10

Thr Arg Lys Xaa Xaa Xaa Xaa Xaa Arg Lys Gly Ser Gly
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence:Peptide
      from K, Q, R-pentapeptide library

<400> SEQUENCE: 11

Thr Arg Lys Lys Lys Lys Lys Lys Arg Lys Gly Ser Gly
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 12

Thr Arg Lys Lys Lys Lys Gln Arg Arg Lys Gly Ser Gly
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 13

Thr Arg Lys Lys Lys Gln Lys Arg Arg Lys Gly Ser Gly
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 14

Thr Arg Lys Lys Lys Gln Arg Arg Arg Lys Gly Ser Gly
1               5                   10
```

```
<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 15

Thr Arg Lys Lys Lys Arg Gln Arg Arg Lys Gly Ser Gly
 1               5                  10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 16

Thr Arg Lys Lys Gln Lys Lys Arg Arg Lys Gly Ser Gly
 1               5                  10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 17

Thr Arg Lys Lys Gln Lys Arg Arg Arg Lys Gly Ser Gly
 1               5                  10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 18

Thr Arg Lys Lys Gln Gln Gln Arg Arg Lys Gly Ser Gly
 1               5                  10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 19

Thr Arg Lys Lys Gln Arg Lys Arg Arg Lys Gly Ser Gly
 1               5                  10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library
```

```
<400> SEQUENCE: 20

Thr Arg Lys Lys Gln Arg Arg Arg Lys Gly Ser Gly
  1               5                  10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 21

Thr Arg Lys Lys Arg Lys Gln Arg Arg Lys Gly Ser Gly
  1               5                  10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 22

Thr Arg Lys Lys Arg Gln Lys Arg Arg Lys Gly Ser Gly
  1               5                  10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 23

Thr Arg Lys Lys Arg Gln Arg Arg Lys Gly Ser Gly
  1               5                  10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 24

Thr Arg Lys Lys Arg Arg Gln Arg Arg Lys Gly Ser Gly
  1               5                  10

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 25

Thr Arg Lys Gln Lys Lys Lys Arg Arg Lys Gly Ser Gly
  1               5                  10

<210> SEQ ID NO 26
<211> LENGTH: 13
<212> TYPE: PRT
```

```
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 26

Thr Arg Lys Gln Lys Lys Arg Arg Lys Gly Ser Gly
  1               5                  10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 27

Thr Arg Lys Gln Lys Gln Gln Arg Arg Lys Gly Ser Gly
  1               5                  10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 28

Thr Arg Lys Gln Lys Arg Lys Arg Arg Lys Gly Ser Gly
  1               5                  10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 29

Thr Arg Lys Gln Lys Arg Arg Arg Arg Lys Gly Ser Gly
  1               5                  10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 30

Thr Arg Lys Gln Gln Lys Gln Arg Arg Lys Gly Ser Gly
  1               5                  10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 31

Thr Arg Lys Gln Gln Gln Lys Arg Arg Lys Gly Ser Gly
  1               5                  10
```

```
<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 32

Thr Arg Lys Gln Gln Gln Gln Gln Arg Lys Gly Ser Gly
 1               5                  10

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 33

Thr Arg Lys Gln Gln Gln Arg Arg Arg Lys Gly Ser Gly
 1               5                  10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 34

Thr Arg Lys Gln Gln Arg Gln Arg Arg Lys Gly Ser Gly
 1               5                  10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 35

Thr Arg Lys Gln Arg Lys Gln Gln Arg Lys Gly Ser Gly
 1               5                  10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 36

Thr Arg Lys Gln Arg Lys Lys Arg Arg Lys Gly Ser Gly
 1               5                  10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library
```

```
<400> SEQUENCE: 37

Thr Arg Lys Gln Arg Lys Arg Arg Lys Gly Ser Gly
 1               5                  10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 38

Thr Arg Lys Gln Arg Gln Gln Arg Arg Lys Gly Ser Gly
 1               5                  10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 39

Thr Arg Lys Gln Arg Arg Lys Arg Arg Lys Gly Ser Gly
 1               5                  10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 40

Thr Arg Lys Gln Arg Arg Arg Arg Arg Lys Gly Ser Gly
 1               5                  10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 41

Thr Arg Lys Arg Gln Lys Lys Arg Arg Lys Gly Ser Gly
 1               5                  10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 42

Thr Arg Lys Arg Gln Lys Arg Arg Arg Lys Gly Ser Gly
 1               5                  10

<210> SEQ ID NO 43
<211> LENGTH: 13
<212> TYPE: PRT
```

```
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 43

Thr Arg Lys Arg Gln Gln Gln Arg Arg Lys Gly Ser Gly
  1               5                  10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 44

Thr Arg Lys Arg Gln Arg Lys Arg Arg Lys Gly Ser Gly
  1               5                  10

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 45

Thr Arg Lys Arg Gln Arg Arg Arg Arg Lys Gly Ser Gly
  1               5                  10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 46

Thr Arg Lys Arg Arg Lys Gln Arg Arg Lys Gly Ser Gly
  1               5                  10

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 47

Thr Arg Lys Arg Arg Gln Lys Arg Arg Lys Gly Ser Gly
  1               5                  10

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 48

Thr Arg Lys Arg Arg Gln Arg Arg Arg Lys Gly Ser Gly
  1               5                  10
```

```
<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 49

Thr Arg Lys Arg Arg Arg Gln Arg Arg Lys Gly Ser Gly
 1               5                  10

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence:Peptide from
      K, Q, R-pentapeptide library

<400> SEQUENCE: 50

Thr Arg Lys Arg Arg Arg Arg Arg Arg Lys Gly Ser Gly
 1               5                  10

<210> SEQ ID NO 51
<211> LENGTH: 35
<212> TYPE: RNA
<213> ORGANISM: Human immunodeficiency virus

<400> SEQUENCE: 51
gcugcucucu ggcuuucgag ccagauuuga gcagc                              35

<210> SEQ ID NO 52
<211> LENGTH: 29
<212> TYPE: RNA
<213> ORGANISM: Artificial Sequence
<220> FEATURE:
<223> OTHER INFORMATION: Description of Artificial Sequence:Small RNA
      mimic of bacterial ribosomal RNA GTPase center

<400> SEQUENCE: 52
ggauguuggc uuagaagcag ccaucaucc                                     29

<210> SEQ ID NO 53
<211> LENGTH: 18
<212> TYPE: RNA
<213> ORGANISM: Artificial Sequence
<220> FEATURE:
<223> OTHER INFORMATION: Description of Artificial Sequence:single
      stranded RNA for testing binding of peptides

<400> SEQUENCE: 53
ccccggugcu cucuggcu                                                 18
```